US00RE41286E

(19) United States
(12) Reissued Patent
Atkinson et al.

(10) Patent Number: US RE41,286 E
(45) Date of Reissued Patent: Apr. 27, 2010

(54) COMPOSITIONS FOR REGENERATION AND REPAIR OF CARTILAGE LESIONS

(75) Inventors: Brent Atkinson, Lakewood, CO (US); James J. Benedict, Arvada, CO (US)

(73) Assignee: Zimmer Orthobiologics, Inc., Austin, TX (US)

(21) Appl. No.: 11/046,674

(22) Filed: Jan. 28, 2005

Related U.S. Patent Documents

Reissue of:
(64) Patent No.: 6,511,958
Issued: Jan. 28, 2003
Appl. No.: 09/505,209
Filed: Feb. 16, 2000

U.S. Applications:
(63) Continuation-in-part of application No. 09/250,370, filed on Feb. 16, 1999, now Pat. No. 6,514,514, which is a continuation-in-part of application No. PCT/EP98/05100, filed on Aug. 12, 1998.

(30) Foreign Application Priority Data

Aug. 14, 1997 (EP) ..... 97810567

(51) Int. Cl.

| | |
|---|---|
| ***A01N 37/18*** | (2006.01) |
| ***A61K 38/00*** | (2006.01) |
| ***A61K 9/14*** | (2006.01) |
| ***A61K 35/32*** | (2006.01) |
| ***A61F 13/00*** | (2006.01) |
| ***A61F 2/00*** | (2006.01) |
| ***C07K 1/00*** | (2006.01) |
| ***C07K 14/00*** | (2006.01) |
| ***C07K 17/00*** | (2006.01) |

(52) U.S. Cl. ..... 514/2; 424/422; 424/423; 424/484; 424/549; 514/21; 530/350

(58) Field of Classification Search ..... 424/85.1, 424/198.1, 422, 423, 484, 549; 514/2, 21; 530/350, 351

See application file for complete search history.

(56) References Cited

U.S. PATENT DOCUMENTS

| | | | | |
|---|---|---|---|---|
| 3,318,774 | A | 5/1967 | Dingwall et al. | 167/74 |
| 3,458,397 | A | 7/1969 | Myers et al. | 195/2 |
| 3,867,728 | A | 2/1975 | Stubstad et al. | 3/1 |
| 3,927,205 | A | 12/1975 | Ohno et al. | 424/80 |
| 4,002,602 | A | 1/1977 | Goldstein | 260/112.5 |
| 4,172,128 | A | 10/1979 | Thiele et al. | 424/95 |
| 4,294,753 | A | 10/1981 | Urist | 260/112 |
| 4,394,370 | A | 7/1983 | Jefferies | 424/15 |
| 4,413,359 | A | 11/1983 | Akiyama et al. | 3/1 |
| 4,434,094 | A | 2/1984 | Seyedin et al. | 260/112 |
| 4,440,750 | A | 4/1984 | Glowacki et al. | 424/95 |
| 4,455,256 | A | 6/1984 | Urist | 260/112 R |
| 4,529,590 | A | 7/1985 | LeVeen et al. | 424/95 |
| 4,559,299 | A | 12/1985 | Rotman | 435/29 |
| 4,563,350 | A | 1/1986 | Nathan et al. | 424/95 |
| 4,596,574 | A | 6/1986 | Urist | 424/22 |
| 4,608,199 | A | 8/1986 | Caplan et al. | 530/414 |
| 4,619,989 | A | 10/1986 | Urist | 530/417 |
| 4,620,327 | A | 11/1986 | Caplan et al. | 632/10 |
| 4,627,853 | A | 12/1986 | Campbell et al. | 623/16 |
| 4,627,982 | A | 12/1986 | Seyedin et al. | 514/21 |
| 4,637,931 | A | 1/1987 | Schmitz | 424/78 |
| 4,663,358 | A | 5/1987 | Hyon et al. | 521/64 |
| 4,678,470 | A | 7/1987 | Nashef et al. | 623/23.63 |
| 4,681,763 | A | 7/1987 | Nathanson et al. | 424/95 |
| 4,743,259 | A | 5/1988 | Bolander et al. | 623/16 |
| 4,761,471 | A | 8/1988 | Urist | 530/350 |
| 4,772,287 | A | 9/1988 | Ray et al. | 623/17 |
| 4,774,227 | A | 9/1988 | Piez et al. | 514/21 |
| 4,774,228 | A | 9/1988 | Seyedin et al. | 514/21 |
| 4,774,322 | A | 9/1988 | Seyedin et al. | 514/21 |
| 4,789,663 | A | 12/1988 | Wallace et al. | 514/21 |
| 4,789,732 | A | 12/1988 | Urist | 514/21 |
| 4,795,467 | A | 1/1989 | Piez et al. | 623/16 |
| 4,795,804 | A | 1/1989 | Urist | 530/350 |
| 4,801,299 | A | 1/1989 | Brendel et al. | 623/1 |
| 4,804,744 | A | 2/1989 | Sen | 530/350 |
| 4,810,691 | A | 3/1989 | Seyedin et al. | 514/2 |
| 4,834,757 | A | 5/1989 | Brantigan | 623/17 |
| 4,843,063 | A | 6/1989 | Seyedin et al. | 514/2 |
| 4,863,732 | A | 9/1989 | Nathan et al. | 424/95 |
| 4,877,864 | A | 10/1989 | Wang et al. | 530/324 |
| 4,888,366 | A | 12/1989 | Chu et al. | 523/115 |
| 4,902,296 | A | 2/1990 | Bolander et al. | 623/16 |
| 4,904,260 | A | 2/1990 | Ray et al. | 623/17 |
| 4,950,483 | A | 8/1990 | Ksander et al. | 424/422 |
| 4,952,404 | A | 8/1990 | Vallee et al. | 424/422 |
| 4,968,590 | A | 11/1990 | Kuberasampath et al. | 530/326 |
| 4,975,526 | A | 12/1990 | Kuberasampath et al. | 530/350 |
| 4,975,527 | A | 12/1990 | Koezuka et al. | 530/356 |
| 4,992,226 | A | 2/1991 | Piez et al. | 264/109 |
| 5,001,169 | A | 3/1991 | Nathan et al. | 523/115 |
| 5,002,583 | A | 3/1991 | Pitaru et al. | 623/66 |

(Continued)

FOREIGN PATENT DOCUMENTS

| | | | |
|---|---|---|---|
| CN | 1163780 | A | 11/1997 |
| DE | 29 33 174 | | 4/1980 |

(Continued)

OTHER PUBLICATIONS

Bentz et al. (1991) Transforming growth factor–beta2 enhances the osteoinductive activity of a bovine bone–derived fraction containing bone morphogenetic protein–2 and 3. Matrix 11: 269–275.*

(Continued)

*Primary Examiner*—Anne-Marie Falk
(74) *Attorney, Agent, or Firm*—Howrey LLP

(57) ABSTRACT

Disclosed is a cartilage repair product that induces both cell ingrowth into a bioresorbable material and cell differentiation into cartilage tissue. Such a product is useful for regenerating and/or repairing both vascular and avascular cartilage lesions, particularly articular cartilage lesions, and even more particularly mensical tissue lesions, including tears as well as segmental defects. Also disclosed is a method of regenerating and repairing cartilage lesions using such a product.

80 Claims, 8 Drawing Sheets

U.S. PATENT DOCUMENTS

| | | | | |
|---|---|---|---|---|
| 5,015,255 | A | 5/1991 | Kuslich | 623/17 |
| 5,047,055 | A | 9/1991 | Bao et al. | 623/17 |
| 5,053,050 | A | 10/1991 | Itay | 623/16 |
| 5,100,422 | A | 3/1992 | Berguer et al. | 606/151 |
| 5,108,438 | A | 4/1992 | Stone | 623/17 |
| 5,116,738 | A | 5/1992 | Wang et al. | 435/69.1 |
| 5,118,667 | A | 6/1992 | Adams et al. | 514/12 |
| 5,141,905 | A | 8/1992 | Rosen et al. | 435/69.1 |
| 5,147,374 | A | 9/1992 | Fernandez | 606/151 |
| 5,152,791 | A | 10/1992 | Hakamatsuka et al. | 623/16 |
| 5,171,278 | A | 12/1992 | Pisharodi | 623/17 |
| 5,187,076 | A | 2/1993 | Wozney et al. | 435/69.1 |
| 5,192,326 | A | 3/1993 | Bao et al. | 623/17 |
| 5,206,023 | A | 4/1993 | Hunziker | 424/423 |
| 5,208,219 | A | 5/1993 | Ogawa et al. | 514/12 |
| 5,219,576 | A | 6/1993 | Chu et al. | 424/484 |
| 5,258,043 | A | 11/1993 | Stone | 623/66 |
| 5,260,763 | A | 11/1993 | Yamashita | 356/30 |
| 5,270,300 | A | 12/1993 | Hunziker | 514/12 |
| 5,290,763 | A | 3/1994 | Poser et al. | 514/21 |
| 5,306,311 | A | 4/1994 | Stone et al. | 623/18 |
| 5,314,477 | A | 5/1994 | Marnay | 623/17 |
| 5,322,933 | A | 6/1994 | Davies et al. | 530/399 |
| 5,356,630 | A | 10/1994 | Laurencin et al. | 424/426 |
| 5,368,858 | A | 11/1994 | Hunziker | 424/423 |
| 5,371,191 | A | 12/1994 | Poser et al. | 530/350 |
| 5,387,213 | A | 2/1995 | Breard et al. | 606/61 |
| 5,390,683 | A | 2/1995 | Pisharodi | 128/898 |
| 5,393,739 | A | 2/1995 | Bentz et al. | 514/12 |
| 5,425,772 | A | 6/1995 | Brantigan | 623/17 |
| 5,464,439 | A | 11/1995 | Gendler | 623/16 |
| 5,478,739 | A | 12/1995 | Slivka et al. | 435/240.23 |
| 5,510,121 | A | 4/1996 | Rhee et al. | 424/520 |
| 5,514,180 | A | 5/1996 | Heggeness et al. | 623/17 |
| 5,543,392 | A | 8/1996 | Tomita et al. | 514/8 |
| 5,545,229 | A | 8/1996 | Parsons et al. | 623/17 |
| 5,562,736 | A | 10/1996 | Ray et al. | 623/17 |
| 5,563,124 | A | 10/1996 | Damien et al. | 514/21 |
| 5,591,234 | A | 1/1997 | Kirsch | 623/16 |
| 5,595,722 | A | 1/1997 | Grainger et al. | 424/9.2 |
| 5,616,490 | A | 4/1997 | Sullivan et al. | 435/366 |
| 5,629,009 | A | 5/1997 | Laurencin et al. | 424/426 |
| 5,632,747 | A | 5/1997 | Scarborough et al. | 606/79 |
| 5,645,597 | A | 7/1997 | Krapiva | 623/17 |
| 5,656,492 | A | 8/1997 | Glowacki et al. | 435/284.1 |
| 5,656,587 | A | 8/1997 | Sporn et al. | 514/2 |
| 5,658,343 | A | 8/1997 | Hauselmann et al. | 623/20 |
| 5,658,882 | A | 8/1997 | Celeste et al. | 514/12 |
| 5,681,310 | A | 10/1997 | Yuan et al. | 606/61 |
| 5,681,353 | A | 10/1997 | Li et al. | 623/18 |
| 5,705,477 | A | 1/1998 | Sporn et al. | 514/2 |
| 5,707,962 | A | 1/1998 | Chen et al. | 514/12 |
| 5,716,416 | A | 2/1998 | Lin | 623/17 |
| 5,718,707 | A | 2/1998 | Mikhail | 606/94 |
| 5,723,331 | A | 3/1998 | Tubo et al. | 435/366 |
| 5,741,685 | A | 4/1998 | Vacanti | 435/182 |
| 5,786,217 | A | 7/1998 | Tubo et al. | 435/402 |
| 5,800,537 | A | 9/1998 | Bell | 623/11 |
| 5,817,153 | A | 10/1998 | Pendl et al. | 8/94.11 |
| 5,821,333 | A | 10/1998 | Carter et al. | 530/350 |
| 5,824,093 | A | 10/1998 | Ray et al. | 623/17 |
| 5,827,328 | A | 10/1998 | Buttermann | 623/17 |
| 5,842,477 | A | 12/1998 | Naughton et al. | 128/898 |
| 5,854,397 | A | 12/1998 | Mechanic | 520/356 |
| 5,865,846 | A | 2/1999 | Bryan et al. | 623/17 |
| 5,902,785 | A | 5/1999 | Hattersley et al. | 514/2 |
| 5,904,716 | A | 5/1999 | Gendler | 623/11 |
| 5,908,784 | A | 6/1999 | Johnstone et al. | 435/372 |
| 5,919,235 | A | 7/1999 | Husson et al. | 623/17 |
| 5,928,940 | A | 7/1999 | Sampath et al. | 435/325 |
| 5,944,754 | A | 8/1999 | Vacanti | 623/11 |
| 5,962,325 | A | 10/1999 | Naughton et al. | 435/395 |
| 5,964,807 | A | 10/1999 | Gan et al. | 623/17 |
| 5,972,884 | A | 10/1999 | Cohen et al. | 514/12 |
| 5,976,186 | A | 11/1999 | Bao et al. | 623/17 |
| 6,010,698 | A | 1/2000 | Kussendrager et al. | 424/94.1 |
| 6,013,853 | A | 1/2000 | Athanasiou et al. | 623/11 |
| 6,042,610 | A | 3/2000 | Li et al. | 623/20 |
| 6,054,122 | A | 4/2000 | MacPhee et al. | 424/94.4 |
| 6,080,579 | A | 6/2000 | Hanley, Jr. et al. | 435/366 |
| 6,123,731 | A | 9/2000 | Boyce et al. | 623/23.63 |
| 6,143,501 | A | 11/2000 | Sittinger et al. | 435/6 |
| 6,150,163 | A | 11/2000 | McPherson et al. | 435/384 |
| 6,150,328 | A | 11/2000 | Wang et al. | 514/12 |
| 6,177,406 | B1 | 1/2001 | Wang et al. | 514/12 |
| 6,179,871 | B1 | 1/2001 | Halpern | 623/11.11 |
| 6,187,742 | B1 | 2/2001 | Wozney et al. | 514/2 |
| 6,206,923 | B1 | 3/2001 | Boyd et al. | 623/17.11 |
| 6,211,157 | B1 | 4/2001 | Benedict et al. | 514/21 |
| 6,242,247 | B1 | 6/2001 | Rieser et al. | 435/297.1 |
| 6,245,107 | B1 | 6/2001 | Ferree | 623/17 |
| 6,251,143 | B1 | 6/2001 | Schwartz et al. | 623/23.72 |
| 6,299,650 | B1 | 10/2001 | Van Blitterswijk et al. | 623/23.63 |
| 6,315,992 | B1 | 11/2001 | Noh et al. | 424/93.21 |
| 6,340,369 | B1 | 1/2002 | Ferree | 623/17.11 |
| 6,344,058 | B1 | 2/2002 | Ferree | 623/17.11 |
| 6,352,557 | B1 | 3/2002 | Ferree | 623/17.11 |
| 6,372,257 | B1 | 4/2002 | Marchosky | 424/488 |
| 6,413,511 | B1 | 7/2002 | Glorioso et al. | 424/93.21 |
| 6,419,702 | B1 | 7/2002 | Ferree | 623/17.11 |
| 6,429,013 | B1 | 8/2002 | Halvorsen et al. | 435/377 |
| 6,451,060 | B2 | 9/2002 | Masuda et al. | 623/23.72 |
| 6,468,960 | B1 | 10/2002 | Lukanidin et al. | 514/2 |
| 6,492,327 | B2 | 12/2002 | Junker et al. | 514/2 |
| 6,498,142 | B1 | 12/2002 | Sampath et al. | 514/12 |
| 6,511,958 | B1 | 1/2003 | Atkinson et al. | 514/2 |
| 6,514,514 | B1 | 2/2003 | Atkinson et al. | 424/423 |
| 6,558,949 | B2 | 5/2003 | Min et al. | 435/366 |
| 6,582,471 | B1 | 6/2003 | Bittmann et al. | 623/23.63 |
| 6,626,945 | B2 | 9/2003 | Simon et al. | 623/17.19 |
| 6,626,950 | B2 | 9/2003 | Brown et al. | 623/23.72 |
| 6,723,335 | B1 | 4/2004 | Moehlenbruck et al. | 424/425 |
| 7,141,072 | B2 | 11/2006 | Geistlich et al. | 623/23.74 |
| 2002/0009789 | A1 | 1/2002 | Hanyu et al. | 435/189 |
| 2002/0013627 | A1 | 1/2002 | Geistlich et al. | 623/23.63 |
| 2002/0040004 | A1 | 4/2002 | Benedict et al. | 514/21 |
| 2003/0135209 | A1 | 7/2003 | Seedhom et al. | 606/60 |

FOREIGN PATENT DOCUMENTS

| | | | |
|---|---|---|---|
| DE | WO94/26211 | | 11/1994 |
| DE | 195 03 504 | | 3/1996 |
| DE | 697 14 035 | | 3/2003 |
| EP | 0 121 976 | | 10/1984 |
| EP | 0 339 607 | B1 | 11/1989 |
| EP | 0 411 925 | A2 | 2/1991 |
| EP | 0 493 698 | | 7/1992 |
| EP | 0516901 | | 12/1992 |
| EP | 0 469 070 | B1 | 9/1996 |
| EP | 0896825 | A1 * | 8/1997 |
| EP | 0 896 825 | | 2/1999 |
| EP | 0 433 225 | | 4/1999 |
| EP | 0 747 066 | | 12/2003 |
| GB | 2 137 209 | A | 10/1984 |
| JP | 2001-514935 | | 9/2001 |
| WO | WO90/12603 | | 11/1990 |
| WO | WO91/16867 | | 11/1991 |
| WO | WO92/09697 | | 6/1992 |
| WO | WO92/18142 | | 10/1992 |
| WO | WO93/15694 | | 8/1993 |
| WO | WO94/09722 | | 5/1994 |

| | | |
|---|---|---|
| WO | WO94/20151 | 9/1994 |
| WO | WO94/25080 | 11/1994 |
| WO | WO95/13767 | 5/1995 |
| WO | WO95/16035 | 6/1995 |
| WO | WO95/30383 | 11/1995 |
| WO | WO96/24302 | 8/1996 |
| WO | WO96/24310 | 8/1996 |
| WO | WO96/27333 | 9/1996 |
| WO | WO96/34955 | 11/1996 |
| WO | WO96/39169 | 12/1996 |
| WO | WO96/39170 | 12/1996 |
| WO | WO96/41818 | 12/1996 |
| WO | WO97/41880 | 11/1997 |
| WO | WO97/46665 | 12/1997 |
| WO | WO98/32333 | 7/1998 |
| WO | WO98/35653 | 8/1998 |
| WO | WO98/56317 | 12/1998 |
| WO | WO99/02674 | 1/1999 |
| WO | WO99/08728 | 2/1999 |
| WO | WO99/31136 | 6/1999 |
| WO | WO99/57146 | 11/1999 |
| WO | WO00/15274 | 3/2000 |
| WO | WO00/17321 | 3/2000 |
| WO | WO00/48550 | 8/2000 |
| WO | WO00/62832 | 10/2000 |
| WO | WO01/34166 | 5/2001 |
| WO | WO01/43667 | 6/2001 |
| WO | WO01/66130 | 9/2001 |
| WO | WO01/76654 | 10/2001 |
| WO | WO02/00244 | 1/2002 |
| WO | WO02/47713 | 6/2002 |
| WO | WO02/50112 | 6/2002 |
| WO | WO03/026689 | 4/2003 |
| WO | WO03/059436 | 7/2003 |
| WO | WO03/077852 | 9/2003 |
| WO | WO04/075940 | 9/2004 |
| WO | WO07/011610 | 1/2007 |

OTHER PUBLICATIONS

Bourque et al., *Int. J. Dev. Biol.* 37:573–579 (1993).
Cuevas et al., *European Journal of Medical Research* 4:403–410 (Oct. 15, 1999).
Vukicevic et al., *J. Clin. Invest.* 102(1):202–214 (Jul. 1998).
Hill et al., *Biochimica et Biophysica Acta* 1201:193–202 (1994).
Song et al., *Journal of Controlled Release* 43:197–212 (Jan. 1997).
Baragi et al., *Osteoarthritis and Cartilage* 5:275–282 (1997).
Chernousov et al., *The Journal of Biological Chemistry* 266(17):10851–10858 (1991).
Cornell et al., *Nature* 387:580–583 (Jun. 1997).
Hu et al., "Injection of basic fibroblast growth factor and bone morphogenetic protein for osteogenesis stimulation," *Chemical Abstracts* 132(4):1132, Abstract No. 40522x (Jan. 24, 2000).
Levine et al., "Bone Morphogenetic Protein Promotes Vascularization and Osteoinduction in Preformed Hydroxyapatite in the Rabbit," *Annals of Plastic Surgery* 39(2):158–168 (Aug. 1997).
Mueller et al., "Myocardial angiogenesis induction with bone protein derived growth factors (animal experiment)," *Swiss Medical Weekly* 131:23–25 (Jan. 12, 2001).
Pollock et al., *Petiatr. Surg. Int.* 15:164–167 (1999).
Pollock et al., *Transplantation Proceedings* 29:2131–2133 (1997).
Procházka et al., *Journal of Reproduction and Fertility,* Abstract Series No. 25, p. 64, Abstract No. 173 (Jul. 2000).
Rodeo et al., *Am. J. Sports Med.* 27(4):476–488 (1999).
Song et al., *Journal of Controlled Release* 43:197–212 (1997).
Sampath et al., *Pro. Natl. Acad. Sci. USA* 84:7109–7113 (Oct. 1987).
Reddi, Chapter 2, "Regulation of Bone Differentiation by Local and Systemic Factors," *Bone and Mineral Research 3,* William A. Peck, editor, Elsevier Science Publishers B.V. (1985).
Block et al., *Laboratory Medicine* 13(5):290–298 (May 1982).
Lucas et al., *J. Biomed. Mater. Res.: Applied Biomaterials* 23:23–39 (1989).
Arnoczky, *Clinical Orthopaedics and Related Research,* No. 367S:S244–S253 (Oct. 1999).
Barry et al., "Chondrogenic Constructs of Mesenchymal Stem Cells on Hyaff–11, A Hyaluronan Ester, as Implants for Repair of Osteochondral Lesions," *44th Annual Meeting, Orthopaedic Research Society,* New Orleans, Louisiana, p. 799 (Mar. 16–19, 1998).
de Groot et al., *Biomaterials* 18(8):613–622 (1997).
Ertl et al., "Successful Meniscal Repair Utilizing Meniscal Tissue Engineered Constructs: One Year Results," *42nd Annual Meeting, Orthopaedic Research Society,* Atlanta, Georgia, p. 539 (Feb. 19–22, 1996).
Ibarra et al., *Transplantation Proceedings* 29:986–988 (1997).
Ibarra et al., "Transplantation of Tissue Engineered Meniscus in Sheep," *44th Annual Meeting, Orthopaedic Research Society,* New Orleans, Louisiana, p. 293 (Mar. 16–19, 1998).
Ibarra et al., "Tissue Engineered Repair of Canine Meniscus Explants In Vitro and in Nude Mice Model," *44th Annual Meeting, Orthopaedic Research Society,* New Orleans, Louisiana, p. 148–25 (Mar. 16–19, 1998).
Nehrer et al., "Autologous Chondrocyte–Seeded Type I and II Collagen Matrices Implanted in a Chondral Defect in a Canine Model," *44th Annual Meeting, Orthopaedic Research Society,* New Orleans, Louisiana, p. 377 (Mar. 16–19, 1998).
Sonoda et al., "Characterization of Tissue Healing Following Meniscal Injury and Repair: The Effect of Hyaluronan Treatment," *44th Annual Meeting, Orthopaedic Research Society,* New Orleans, Louisiana, p. 887 (Mar. 16–19, 1998).
Temple et al., "Effect of Meniscal Repair and Hyaluronan Treatment on Cartilage Degeneration of the Femur and Tibia in the Rabbit," *45th Annual Meeting, Orthopaedic Research Society,* Anaheim, California, p. 669 (Feb. 1–4, 1999).
Stone et al., "Surgical Technique of Meniscal Replacement," *Technical Note,* The Stone Clinic (Apr. 1993).
Stone et al., *Journal of Bone & Joint Surgery* 79:1770–1777 (1997).
Atkinson et al., "Elucidation of Homeoprotein Cart–1 Function During In Vitro Chondrogenesis of C3H10T1/2 Micromass Cultures," *Annals New York Academy of Sciences,* pp. 206–208 (Jun. 1996).
Atkinson et al., *Journal of Cellular Biochemistry* 65:325–339 (1997).
Atkinson et al., "A Combination of Osteoinductive Proteins Induces Type II Collagen Production in Adult Myoblast and Dermal Cells," *44th Annual Meeting, Orthopaedic Research Society,* New Orleans, Louisiana, p. 889 (Mar. 16–19, 1998).
Sellers et al., *Journal of Bone & Joint Surgery* 79:1452–1463 (1997).
McDevitt et al., *Clin. Orthoped.* 252:8–18 (Mar. 1990).
Fithian et al., *Clin. Orthoped.* 252:19–31 (Mar. 1990).

Freed et al., *J. Biomed. Mater. Res.* 27:11–23 (1993).
Spilker et al., *J. Biochem.* 25:1027–1045 (1992).
Hashimoto et al., *Amer. J. Sports Med.* 20(5):537–541 (1992).
Chen et al., *Annals of Biomedical Engineering* 25(2):269–277 (Mar. 1997).
Kempson et al., *Biochimica et Biophysica Acta* 297(2):456–472 (Feb. 28, 1973).
Riesle et al., *Journal of Cellular Biochemistry* 71(3):313–327 (Dec. 1998).
Kawa–uchi et al., *Endocrine* 3:833–837 (1995).
Ogawa et al., *The Journal of Biological Chemistry* 267:2325–2328 (1992).
Ogawa et al., *The Journal of Biological Chemistry* 267:14233–14237 (Jul. 15, 1992).
Ogawa et al., *Methods in Enzymology* 198:317–327 (1991).
Kim et al., *Biochemistry and Molecular Biology International* 33:253–261 (May 1994).
Bentz et al., *Matrix* 11:269–275 (1991).
Bulpitt et al., *In Situ Polymerizable Hyaluronic Acid Hydrogel Materials,* pp. 152–169 (1999).
Aguiar et al., *Exp. Cell Res.* 246:129–137 (1999).
Ahlgren et al., *Spine* 25:2165–2170 (2000).
Alini et al., *Eur. Spine J.* 11:S215–S220 (2002).
Antoniou et al., *Spine* 21:1153–1161 (May 15, 1996).
Antoniou et al., *J. Clin. Invest.* 98:996–1003 (Aug. 1996).
Ariga et al., *Spine* 26:2414–2420 (2001).
Bao et al., *Biomaterials* 17:1157–1167 (1996).
Buckwalter, *Spine* 20:1307–1314 (Jun. 1, 1995).
Chelberg et al., *J. Anat.* 186:43–53 (1995).
Chiba et al., *Spine* 23:1821–1827 (Sep. 1998).
Cinotti et al., *Spine* 21:995–1000 (Apr. 15, 1996).
Denker et al., *Differentiation* 59:25–34 (1995).
Duance et al., *Spine* 23:2545–2551 (Dec. 1998).
Enker et al., *Spine* 18:1061–1070 (Jun. 15, 1993).
Frick et al., *Spine* 19:1826–1834 (Aug. 15, 1994).
Griffith et al., *Spine* 19:1842–1849 (Aug. 15, 1994).
Gruber et al., *Spine* 25:2153–2157 (2000).
Gu et al., *Spine* 24:2449–2455 (1999).
Guerne et al., *The Journal of Immunology* 144:499–505 (Jan. 15, 1990).
Guerne et al., *Journal of Cellular Physiology* 158:476–484 (1994).
Guerne et al., *Arthritis & Rheumatism* 38(7):960–968 (Jul. 1995).
Hadjipavlou et al., *Orthopaedic Review* 21:733–738 (Jun. 1992).
Hiraki et al., *Journal of Bone and Mineral Research* 6(12):1373–1385 (1991).
Horner et al., *Spine* 26:2543–2549 (2001).
Jahnke et al., *Biochem. J.* 251:347–356 (1988).
Kaapa et al., *Spine* 20:59–67 (Jan. 1, 1995).
Kawakami et al., *Spine* 21:2101–2107 (Sep. 15, 1996).
Kawamura et al., *Developmental Biology* 130:435–442 (1988).
Lee et al., *Spine* 26:2316–2322 (2001).
Luyten et al., *Experimental Cell Research* 210:224–229 (1994).
Madawi et al., *Spine* 21:2123–2129 (Sep. 15, 1996).
Martz et al., *Applied Biomaterials,* pp. 267–288 (Sep. 1997).
Matsuzaki et al., *Spine* 21:178–183 (Jan. 15, 1996).
Meade et al., *Biomaterials* 11:176–180 (1990).
Melrose et al., *Matrix Biology* 14:61–75 (1994).
Moore et al., *J. Heart Valve Dis.* 6:307–315 (May 1997).
Nehrer et al., *Biomaterials* 18:769–776 (1997).
Nishida et al., *Spine* 23:2437–2442 (1998).
Nishda et al., *Spine* 24:2419–2425 (1999).
Nishimura et al., *Spine* 23:1531–1538 (Jul. 1998).
Oegema et al., *J. Biol. Chem.* 254:10579–10581 (1979).
Okuma et al., *J. Orthopaedic Research* 18:988–997 (2000).
Olmarker et al., *Spine* 21:411–414 (Feb. 15, 1996).
Pokharna et al., *Spine* 23:1645–1648 (Aug. 1998).
Reddi, *Matrix Biology* 14:599–606 (1994).
Roberts et al., *Spine* 21:415–420 (Feb. 15, 1996).
Sakaguchi et al., *Theriogenology* 54:1327–1342 (2000).
Sampath et al., *J. Biol. Chem.* 267(28):20352–20362 (1992).
Sasaki et al., *Spine* 26:463–468 (2001).
Schollmeier et al., *Spine* 25:2736–2741 (2000).
Schor et al., *J. Cell Science* 112:3879–3888 (1999).
Skaggs et al., *Spine* 19:1310–1319 (Jun. 15, 1994).
Stevens et al., *Spine* 7:223–233 (1982).
Sumida et al., *Spine* 24:1066–1070 (1999).
Urban et al., *Grieve's Modern Manual Therapy,* pp. 163–175 (1994).
Wehling et al., *Spine* 22(10):1092–1097 (May 15, 1997).
Wittenberg et al., *Spine* 26:1835–1841 (2001).
Yonggang et al., *Journal of Xi'an Medical University* 22(2):132–133 (Apr. 2001).

* cited by examiner

Radial Tear

Suture Repair + Resection

Triple Bucket Handle Tear

Suture Repair and Resection

Collagen
Thickness
1-3 mm

Zone: 1 2 3

Zone 1: Outer, vascularized zone- "repairable"
Zone 2: Middle, semi- vascularized- "irrepairable"
Zone 3: Inner, avascular zone- "irrepairable"

Longitudinal Tear in Avascular Area

COMPOSITIONS FOR REGENERATION AND REPAIR OF CARTILAGE LESIONS

Matter enclosed in heavy brackets [ ] appears in the original patent but forms no part of this reissue specification; matter printed in italics indicates the additions made by reissue.

CROSS REFERENCE TO RELATED APPLICATIONS

This application claims the benefit of priority under 35 U.S.C. §120 as a continuation-in-part of copending U.S. patent application Ser. No. 09/250,370, filed Feb. 16, 1999 *now U.S. Pat. No. 6,514,514* now allowed, and entitled "Device and Method for Regeneration and Repair of Cartilage Lesions", which is a continuation-in-part under 35 U.S.C. §120 of PCT Application No. PCT/EP 98/05100, entitled "Composition and Device for In Vivo Cartilage Repair Comprising Nanocapsules with Osteoinductive And/or Chondroinductive Factors", filed Aug. 12, 1998, which designates the United States and which claims priority from European Application No. EP 97810567.4, entitled "Composition and Device for In Vivo Cartilage Repair", filed Aug. 14, 1997. Each of the above-identified applications is incorporated herein by reference in their entireties.

FIELD OF THE INVENTION

The present invention relates to a cartilage regeneration and repair product that induces cell ingrowth into a bioresorbable material and cell differentiation into cartilage tissue, and to methods of using such a product to repair cartilage lesions.

BACKGROUND OF THE INVENTION

Articular cartilage, an avascular tissue found at the ends of articulating bones, has limited natural capacity to heal. During normal cartilage ontogeny, mesenchymal stem cells condense to form areas of high density and proceed through a series of developmental stages that ends in the mature chondrocyte. The final hyaline cartilage tissue contains only chondrocytes that are surrounded by a matrix composed of type II collagen, sulfated proteoglycans, and additional proteins. The matrix is heterogenous in structure and consists of three morphologically distinct zones: superficial, intermediate, and deep. Zones differ among collagen and proteoglycan distribution, calcification, orientation of collagen fibrils, and the positioning and alignment of chondrocytes (Archer et al., 1996, J. Anat. 189(1):23–35; Morrison et al., 1996, J. Anat. 189(1): 9–22; and Mow et al., 1992, Biomaterials 13(2): 67–97). These properties provide the unique mechanical and physical parameters to hyaline cartilage tissue.

The meniscus, a C-shaped cartilaginous tissue, performs several functions in the knee including load transmission from the femur to the tibia, stabilization in the anterior-posterior position during flexion, and joint lubrication. Damage to the meniscus results in reduced knee stability and knee locking. Over 20 years ago, meniscectomies were performed which permitted immediate pain relief, but were subsequently found to induce the early onset of osteoarthritis (Fairbank, J. Bone Joint Surg. 30B: 664–670; Allen et al., 1984, J. Bone Joint Surg. 66B:666–671; and Roos et al., 1998, Arth. Rheum. 41:687–693). More recently, partial meniscectomies and repair of meniscal tears have been performed (FIGS. 9A–D; Jackson, D., ed., 1995, Reconstructive Knee Surgery Master Techniques in Orthopedic Surgery, ed. R. Thompson, Raven Press: New York). However, partial resection results in the loss of functional meniscus tissue and the early onset of osteoarthritis (Lynch et al., 1983, Clin. Orthop. 172:148–153; Cox et al., 1975, Clin. Orthop. 109:178–183; King, 1995, J. Bone Joint Surg. 77B:836–837). Additionally, repair of meniscal tears is limited to tears in the vascular ⅓ of the meniscus; tears in the semivascular to avascular ⅔ are not repairable (FIGS. 9A–D; Jackson, ibid.). Of the approximately, 560,000 meniscal injuries that occur annually in the United States, an estimated 80% of tears are located in the avascular, irreparable zone. Clearly, a method that both repairs "non-repairable" tears or that can induce regeneration of resected menisci would be valuable for painless musculoskeletal movement and prevention of the early onset of osteoarthritis in a large segment of the population.

The proximal, concave surface of the meniscus contacts the femoral condyle and the distal, flat surface contacts the tibial plateaus. The outer one-third of the meniscus is highly vascularized and contains dense, enervated, connective tissue. In contrast, the remaining meniscus is semivascular or avascular, aneural tissue consisting of fibrochondrocytes surrounded by abundant extracellular matrix (McDevitt et al., Clin. Orthop. Rel. Res. 252:8–17). Fibrochondrocytes are distinctive in both appearance and function compared to undifferentiated fibroblasts. Fibroblasts are elongated cells containing many cellular processes and produce predominantly type I collagen. The matrix produced by fibroblasts does not produce a sufficient mechanical load. In contrast, fibrochondrocytes produce type I and type II collagen and proteoglycans. These matrix components support compressive forces that are commonly exerted on the meniscus during musculoskeletal movement.

In the 1960's, demineralized bone matrix was observed to induce the formation of new cartilage and bone when implanted in ectopic sites (Urist, 1965, Science 150:893–899). The components responsible for the osteoinductive activities were termed Bone Morphogenetic Proteins (BMP). At least seven individual BMP proteins were subsequently identified from bone (BMP 1–7) and amino acid analysis revealed that six of the seven BMPs were related to each other and to other members of the TGF-β superfamily. During endochondral bone formation, TGF-β family members direct a cascade of events that includes chemotaxis, differentiation of pluripotential cells to the cartilage lineage, maturation of chondrocytes to the hypertrophic stage, mineralization of cartilage, replacement of cartilage with bone cells, and the formation of a calcified matrix (Reddi, 1997, Cytokine & Growth Factor Reviews 8:11–20). Although individual, recombinant BMPs can induce these events, the prevalence of multiple TGF-β family members in bone tissue underlies the complexity involved in natural osteogenesis.

Bone Protein (Sulzer Orthopedics Biologics, Wheatridge, Colo.), also referred to herein as BP, is a naturally derived mixture of proteins isolated from demineralized bovine bones that has osteogenic activity in vitro and in vivo. In the rodent ectopic model, BP induces endochondral bone formation or bone formation through a cartilage intermediate (Damien, C. et al., 1990, J. Biomed. Mater. Res. 24:639–654). BP in combination with calcium carbonate promotes bone formation in the body (Poser and Benedict, PCT Publication No. WO95/13767). In vitro, BP has been shown to promote differentiation to cartilage of murine embryonic mesenchymal stem cells (Atkinson et al., 1996, In "Molecular and Developmental Biology of Cartilage", Bethesda, Md., Annals New York Acad. Sci. 785:206–208;

Atkinson et al., 1997, J. Cell. Biochem. 65:325–339) and of adult myoblast and dermal cells (Atkinson et al., 1998, 44th Annual Meeting, Orthopaedic Research Society, abstract). To ensure chondrogenesis in these in vitro systems, however, culture conditions must be tightly controlled throughout the culture period, including by controlling cellular organization within the culture, optimizing media formulations, and adding exogenous factors that must be carefully established to maximize chondrogenesis over mitogenesis. Such optimization of conditions makes the application of the disclosed in vitro methods to an in vivo system unrealistic and unpredictable. In addition, although in vitro cultures of adult myoblast and dermal cells initially resulted in chondrogenesis, the effect was only transient and over time, the cultures reverted to their original phenotype. Although certain embryonic and precursor cell types showed prolonged chrondrogenesis in vitro in these studies, it would be unpredictable or even impossible in the case of embryonic cells that these specific cell types could be recruited to a site in vivo in an adult patient.

Atkinson et al., in PCT Application No. PCT/EP/05100, incorporated herein by reference in its entirety, describe a delivery system for osteoinductive and/or chondroinductive mixture of naturally derived factors for the induction of cartilage repair.

Hunziker (U.S. Pat. Nos. 5,368,858 and 5,206,023) describes a cartilage repair composition consisting of a biodegradable matrix, a proliferation and/or chemotactic agent, and a transforming factor. A two-stage approach is used where each component has a specific function over time. First, a specific concentration of proliferation/chemotactic agent fills the defect with repair cells. Second, a larger transforming factor concentration, preferably provided in conjunction with a delivery system, transforms repair cells to chondrocytes. The second stage delivery of a high concentration of transforming factor in a delivery system (i.e., liposomes) was required to obtain formation of hyaline cartilage tissue at the treatment site.

Chen and Jeffries (U.S. Pat. No. 5,707,962) describe osteogenic compositions consisting of collagen and sorbed factors to enhance osteogenesis.

Valee and King (U.S. Pat. No. 4,952,404) describe healing of injured, avascular meniscus tissue by release of the angiogenic factor, angiogenin, over at least 3 weeks.

Previously, Amoczky et al. described a method using an autogenous fibrin clot to repair an avascular, circular lesion in canine menisci (Amoczky et al., 1988, J. Bone Joint Surg. 70A:1209–1217). This approach enhanced repair of meniscal tissue compared to controls lacking the fibrin clot. However, the repair tissue was not meniscus-like tissue, but rather connective scar tissue.

Hashimoto et al. described a method using fibrin sealant with or without endothelial cell growth factor in avascular, circular meniscal defects in the canine model (Hashimoto et al., 1992, Am. J. Sports Med. 20:537–541). The growth factor added a modest benefit compared to healing with fibrin sealant alone and this additional effect was not observed until three months after treatment, indicating an indirect contribution of the growth factor. In addition, the defect was filled with hyaline cartilage-like cells, which are not typically present in normal meniscus tissue.

Shirakura, et al. describe the use of an autogenous synovium graft sutured into meniscal tears. While the synovium did enhance healing in ⅓ of the animals, the grafts healed with fibrous tissue, not fibrocartilaginous tissue normally observed in meniscus tissue (Shirakura, 1997, Acta. Orthop. Scand. 68:51–54). Furthermore, ⅔ of the grafts did not heal.

The molecular mechanism for cartilage and bone formation has been partially elucidated. Both bone morphogenetic proteins (BMP) and transforming growth factor β (TGFβ) molecules bind to cell surface receptors (i.e., TGFβ/BMP receptors) to initiate a cascade of signals to the nucleus that promotes proliferation, differentiation to cartilage, and/or differentiation to bone (Massague, 1996, Cell 85:947–950). In 1984, Urist described a substantially pure, but not recombinant, BMP combined with a biodegradable poly (lactic acid) polymer delivery system for bone repair (U.S. Pat. No. 4,563,489). This system blends together equal quantities of BMP and poly(lactic acid) (PLA) powder (100 μg of each) and decreases the amount of BMP required to promote bone repair.

Hattersley et al. (WO 96/39170) disclose a two factor composition for inducing cartilaginous tissue formation using a cartilage formation-inducing protein and a cartilage maintenance-inducing protein. Specific recombinant cartilage inducing proteins are specified as BMP-13, MP-52 and BMP-12, and specific cartilage maintenance-inducing proteins are specified as BMP-9. In one embodiment, BMP-9 is encapsulated in a resorbable polymer system and delivered to coincide with the presence of cartilage formation inducing protein(s).

Laurencin et al. (U.S. Pat. No. 5,629,009) disclose a chondrogenesis-inducing device, consisting of apolyanhydride and polyorthoester, that delivers water soluble proteins derived from demineralized bone matrix, TGFβ, epidermal growth factor (EGF), fibroblast growth factor (FGF) or platelet-derived growth factor (PDGF).

Bentz et al. (PCT Publication No. WO 92/09697) have described the use of a bone morphogenetic protein (BMP) with a TGFβ protein for bone repair. The ratio of BMP to TGFβ in the mixture is in the range of 10:1 to 1:10. The addition of TGF-β with either BMP-2 or BMP-3 results in increased osteoinductive activity and an increased ratio of cartilage to bone when compared to either factor alone (Bentz et al., Matrix 11:269–275 (1991); Ogawa et al., J. Biol. Chem., 267(20): 14233–7 (1992); WO92/09697). However, this composition produced substantial bone in the rodent subcutaneous assay.

Bulpitt and Aeschlimann found that TGFβ-2 and BMP-2 led to accelerated bone formation and decreased cartilage formation in the rat ectopic bone formation assay (Bulpitt et al., Tissue Engineering, pp. 162–169 (1999)).

Other studies demonstrate no or little effect of the combination of TGFβ-1 or -2 with BMP. In vitro, the combination of TGFβ-1 and porcine BMP demonstrated no synergistic effects on collagen production (Kim et al., Biochem. Mol. Biol. Int'l, 33(2):253–261 (1994)). Similarly, Ballock et al., demonstrated no synergy between TGFβ-1 and BMP-3 for collagen production in periosteum derived cells in vitro (Ballock et al., J. Ortho. Res., 15:463–7 (1997)).

In the Rosen modified Sampath-Reddi rodent assay (Sampath et al., Proc. Nat'l Acad. Sci. USA, 80(21):6591–5 (1983)), BMP-2 containing implants showed cartilage and bone formation after ten days and mostly bone (no cartilage) after 21 days (U.S. Pat. No. 5,658,882).

Previously, Li and Stone (U.S. Pat. No. 5,681,353) have described a Meniscal Augmentation Device that consists of biocompatible and bioresorbable fibers that acts as a scaffold for the ingrowth of meniscal fibrochondrocytes, supports normal meniscal loads, and has an outer surface that approximates the natural meniscus contour. After partial resection of the meniscus to the vascular zone, this device is implanted into the resulting segmental defect. The results have been described in both canines and humans (Stone et al., 1992, Am. J. Sports Med. 20:104–111; and Stone et al., 1997, J. Bone Joint Surg. 79:1770–1777).

The Meniscus Augmentation Device, the research reports and patent disclosures described above, and current repair surgeries provide encouraging results in the area of cartilage repair, but are not satisfactory to induce repair of "non-repairable" avascular tears in which the repair tissue is meniscus tissue, and are not satisfactory to produce short patient rehabilitation times and regenerated meniscus tissue in the vascular zone. Furthermore, no reports have been described that demonstrate enhanced healing rates of "repairable" meniscal tears in vivo.

SUMMARY OF THE INVENTION

The present invention relates to a product and method for repairing and/or regenerating cartilage lesions. The product and method of the present invention are useful for repairing a variety of cartilage lesions, including articular and mensical lesions, including vascular, semivascular and avascular lesions. Moreover, the product and method of the present invention can be used to repair different sizes and shapes of cartilage lesions, including radial tears, bucket handle tears, and segmental defects.

A first embodiment of the product of the present invention relates to a product for repair of cartilage lesions. Such a product includes: (a) a cartilage repair matrix; and, (b) a cartilage-inducing composition associated with the matrix for provision of a mixture of proteins. In one embodiment of the product of the present invention, a cartilage-inducing composition includes a mixture of proteins which includes: transforming growth factor β1 (TGFβ1), bone morphogenetic protein (BMP)-2, BMP-3, and BMP-7. The quantity of the TGFβ1 in the mixture is from about 0.01% to about 99.99% of total proteins in the mixture; the quantity of the BMP-2 in the mixture is from about 0.01% to about 10% of total proteins in the mixture; the quantity of the BMP-3 in the mixture is from about 0.1% to about 15% of total proteins in the mixture; and, the quantity of the BMP-7 in the mixture is from about 0.01% to about 10% of total proteins in the mixture.

In a second embodiment of the product of the present invention, a cartilage-inducing composition includes a mixture of proteins which includes (a) a bone-derived osteogenic or chondrogenic formulation; and, (b) an exogenous TGFβ protein. The exogenous TGFβ protein is present in an amount sufficient to increase cartilage induction by the composition over a level of cartilage induction by the bone-derived osteogenic or chondrogenic protein formulation in the absence of the exogenous TGFβ protein. In one aspect of this embodiment, the exogenous TGFβ protein is TGFβ1. In this aspect, the ratio of TGFβ1 to all other proteins in the mixture of proteins is at least about 1:10, at least about 1:3, at least about 1:1, or at least about 10:1.

In a third embodiment of the product of the present invention, a cartilage-inducing composition includes a mixture of proteins comprising: (a) a TGFβ protein; and, (b) at least one bone morphogenetic protein (BMP), wherein the ratio of the TGFβ protein to the BMP protein is greater than about 10:1. In this embodiment, the TGFβ protein can be any TGFβ protein, including TGFβ1, TGFβ2, TGFβ3, TGFβ4, TGFβ5, or mixtures thereof. In a preferred embodiment, the TGFβ protein is TGFβ1 or TGFβ2, with TGFβ1 being most preferred. The BMP protein can be any BMP protein, including, but not limited to, BMP-2, BMP-3, BMP-4, BMP-5, BMP-6, BMP-7, BMP-8, BMP-9, CDMP, and mixtures thereof.

In one aspect of the any of the above-described embodiments of the present invention, the mixture of proteins includes TGFβ superfamily proteins: TGFβ1, bone morphogenetic protein (BMP)-2, BMP-3, and BMP-7, wherein the TGFβ superfamily proteins comprise from about 0.5% to about 99.99% of the mixture of proteins. In one aspect, the TGFβ superfamily proteins comprise from about 0.5% to about 25% of the mixture of proteins; in another aspect, the TGFβ superfamily proteins comprise from about 1% to about 10% of the mixture of proteins.

In one aspect of each of the above-referenced embodiments, the quantity of the TGFβ1 in the mixture is from about 0.01% to about 75% of total proteins in the mixture; in another aspect, the quantity of the TGFβ1 in the mixture is from about 0.01% to about 50% of total proteins in the mixture; in another aspect, the quantity of the TGFβ1 in the mixture is from about 0.01% to about 25% of total proteins in the mixture; in another aspect, the quantity of the TGFβ1 in the mixture is from about 0.01% to about 10% of total proteins in the mixture; in another aspect, the quantity of the TGFβ1 in the mixture is from about 0.1% to about 1% of total proteins in the mixture; in another aspect, the quantity of the TGFβ1 in the mixture is from about 33% to about 99.99% of total proteins in the mixture; in another aspect, the quantity of the TGFβ1 in the mixture is from about 50% to about 99.99% of total proteins in the mixture.

In one aspect of each of the above-referenced embodiments, the quantity of the BMP-2 in the mixture is from about 0.1% to about 5% of total proteins in the mixture. In one aspect of each of the above-referenced embodiments, the quantity of the BMP-3 in the mixture is from about 0.1% to about 5% of total proteins in the mixture. In one aspect of each of the above-referenced embodiments, the quantity of the BMP-7 in the mixture is from about 0.1% to about 5% of total proteins in the mixture. In the first embodiment of the product of the present invention, the quantity of BMP-3 in the mixture is from about 0.1% to about 10% of total proteins in the mixture.

In one aspect of each of the above-referenced embodiments, the mixture of proteins further comprises a protein selected from the group consisting of TGFβ2, TGFβ3, BMP-4, BMP-5, BMP-6, BMP-8, BMP-9, and cartilage-derived morphogenetic protein (CDMP). In one aspect, the TGFβ2 comprises from about 0.5% to about 12% of the mixture of proteins; in another aspect, the TGFβ3 comprises from about 0.01% to about 15% of the mixture of proteins; in another aspect, the BMP-4 comprises from about 0.01% to about 1% of the mixture of proteins; in another aspect, the BMP-5 comprises from about 0.01% to about 1% of the mixture of proteins; in another aspect, the BMP-6 comprises from about 0.01% to about 1% of the mixture of proteins; in another aspect, the CDMP comprises from about 0.01% to about 1% of the mixture of proteins.

In another aspect of each of the above-referenced embodiments, the mixture of proteins further comprises at least one bone matrix protein. The bone matrix protein can include, but is not limited to, osteocalcin, osteonectin, bone sialoprotein (BSP), lysyloxidase, cathepsin L pre, osteopontin, matrix GLA protein (MGP), biglycan, decorin, proteoglycanchondroitin sulfate III (PG-CS III), bone acidic glycoprotein (BAG-75), thrombospondin (TSP) and fibronectin. Typically, the bone matrix protein comprises from about 20% to about 98% of the mixture of proteins. In one aspect, the bone matrix proteins comprise: osteocalcin, osteonectin, bone sialoprotein (BSP), lysyloxidase, and cathepsin L pre. In another aspect, the bone matrix protein comprises from about 40% to about 98% of the mixture of proteins.

In another aspect of each of the above-referenced embodiments, the mixture of proteins further comprises at least one growth factor protein. The growth factor protein can include, but is not limited to, fibroblast growth factor-I (FGF-I), FGF-II, FGF-9, leukocyte inhibitory factor (LIF), insulin, insulin growth factor I (IGF-I), IGF-II, platelet-derived growth factor AA (PDGF-AA), PDGF-BB, PDGF-AB, stromal derived factor-2 (SDF-2), pituitary thyroid hormone (PTH), growth hormone, hepatocyte growth factor (HGF), epithelial growth factor (EGF), transforming growth factor-α (TGFα) and hedgehog proteins. Typically, the growth factor protein comprises from about 0.01% to about 50% of the mixture of proteins. In one aspect, the growth factor protein comprises from about 0.05% to about 25% of the mixture of proteins; in another aspect, the growth factor protein comprises from about 0.1% to about 10% of the mixture of proteins. Preferably, the growth factor protein is fibroblast growth factor-I (FGF-I). In this aspect, the FGF-I comprises from about 0.001% to about 10% of the mixture of proteins.

In yet another aspect of each of the above-identified embodiments of the present invention, the composition further comprises one or more serum proteins. The serum proteins can include, but are not limited to, albumin, transferrin, α2-Hs GlycoP, IgG, α1-antitrypsin, β2-microglobulin, Apo A1 lipoprotein (LP) and Factor XIIIb. In one aspect, the serum proteins are selected from the group consisting of albumin, transferrin, Apo A1 LP and Factor XIIIb.

In one aspect of any of the above-referenced embodiments of the present invention, the mixture of proteins comprises TGFβ1, TGFβ2, TGFβ3, BMP-2, BMP-3, BMP-4, BMβ5, BMP-6, BMP-7, CDMP, FGF-I, osteocalcin, osteonectin, BSP, lysyloxidase, cathepsin L pre, albumin, transferrin, Apo A1 LP and Factor XIIIb. In another aspect, the mixture of proteins comprises Bone Protein (BP). In yet another aspect, the cartilage inducing composition has an identifying characteristic selected from the group consisting of an ability to induce cellular infiltration, an ability to induce cellular proliferation, an ability to induce angiogenesis, and an ability to induce cellular differentiation to type II collagen-producing chondrocytes.

In one aspect of any of the above-referenced embodiments of the present invention, the cartilage-inducing composition is at a concentration of from about 0.5% to about 33% by weight of the product. In another aspect, the cartilage-inducing composition is at a concentration of from about 1% to about 20% by weight of the product.

In the first embodiment of the product of the present invention, the mixture of proteins, when used at a concentration of at least about 10 μg per 6.5–7.3 mg of bovine tendon collagen in a rat subcutaneous assay, induces a bone score of from about 1.0 to about 3.5, using a bone grading scale set forth in Table 8, and induces a cartilage score of at least about 1.2, using a cartilage grading scale set forth in Table 9.

In the second and third embodiments of the product of the present invention, the composition, when used at a concentration of at least about 10 μg per 6.5–7.3 mg of bovine tendon collagen in a rat subcutaneous assay, induces a bone score of less than about 2.0, using a bone grading scale set forth in Table 8, and induces a cartilage score of at least about 2.0, using a cartilage grading scale set forth in Table 9. Preferably, in the second and third embodiments, the composition, when used at a concentration of at least about 10 μg per 6.5–7.3 mg of bovine tendon collagen in a rat subcutaneous assay, induces a bone score of less than about 2.0, using a bone grading scale set forth in Table 8, and induces a cartilage score of at least about 2.5, using a cartilage grading scale set forth in Table 9. More preferably, in the second and third embodiments, the composition, when used at a concentration of at least about 10 μg per 6.5–7.3 mg of bovine tendon collagen in a rat subcutaneous assay, induces a bone score of less than about 2.0, using a bone grading scale set forth in Table 8, and induces a cartilage score of at least about 3.0, using a cartilage grading scale set forth in Table 9.

In one aspect of the first embodiment of the present invention, the ratio of TGFβ1 to all other proteins in the mixture of proteins is at least about 1:10; in another aspect, the ratio of TGFβ1 to all other proteins in the mixture of proteins is at least about 1:3; in another aspect, the ratio of TGFβ1 to all other proteins in the mixture of proteins is at least about 1:1; in another aspect, the ratio of TGFβ1 to all other proteins in the mixture of proteins is at least about 10:1.

In the second or third embodiment of the product of the present invention, the TGFβ protein can be a recombinant TGFβ protein, or can be purified from a bone-derived protein mixture. In one aspect, the ratio of the TGFβ protein to the BMP protein is greater than about 100:1; in another aspect, the ratio of the TGFβ protein to the BMP protein is greater than about 1000:1; in another aspect, the ratio of the TGFβ protein to the BMP protein is greater than about 10,000:1.

In the third embodiment referenced above, in a preferred aspect, the TGFβ protein is TGFβ1. In another preferred aspect of this embodiment, the BMP protein is selected from the group consisting of BMP-2, BMP-3, BMP-4, BMP-5, BMP-6, BMP-7, BMP-8, BMP-9 and CDMP.

Various other aspects of each of the above-identified embodiments of the product of the present invention are described in detail below.

The product of the present invention can also be formulated to include: (a) a cartilage repair matrix; and (b) a cartilage-inducing composition associated with the matrix, which includes cells that have been cultured with the above-described mixture of chondrogenesis-enhancing proteins.

The cartilage repair matrix of a shape and size that conforms to the cartilage defect such that the defect is repaired. As such, the matrix can be configured as a sheet, which is most suitable for repairing cartilage tears, or the matrix can be configured to repair a segmental defect, which can include a tapered shape. The cartilage repair matrix can be formed of any suitable material, including synthetic polymeric material and ground substances. In one embodiment, the matrix is bioresorbable. In another embodiment, the matrix is porous. When the matrix is configured as a sheet, the matrix is preferably not cross-linked, and when the matrix is configured to repair a segmental defect, the matrix is preferably cross-linked.

The cartilage-inducing composition can be associated with the matrix by any suitable method, including, but not limited to freeze-drying the composition onto a surface of said matrix and suspension within said cartilage repair matrix of a delivery formulation containing said composition. Additionally, the composition can be associated with the matrix ex vivo or in vivo.

Another embodiment of the present invention relates to a method for repair of cartilage lesions, which includes the steps of implanting and fixing into a cartilage lesion a cartilage repair product of the present invention, as described above, including a cartilage repair product including an of the above-referenced embodiments of a cartilage-inducing composition. The method of the present invention can be used to enhance the rate and/or quality of repair of vascular cartilage tears and segmental defects, and can provide the ability to repair semivascular and avascular tears and segmental defects that, prior to the present invention, were typically considered to be irreparable. When the lesion is in semivascular or avascular cartilage, the product can additionally include a time controlled delivery formulation.

In one aspect, the method of the present invention includes the use of two cartilage repair products to repair a segmental defect. The first product includes a cartilage repair matrix, which is configured as a sheet, is associated with the chondrogenesis-inducing composition as described above. The second product includes a cartilage repair matrix configured to replace cartilage removed from the segmental defect, which may or may not be associated with the chondrogenesis-inducing composition of the present invention.

BRIEF DESCRIPTION OF THE FIGURES OF THE INVENTION

DETAILED DESCRIPTION OF THE INVENTION

Figure 1A:
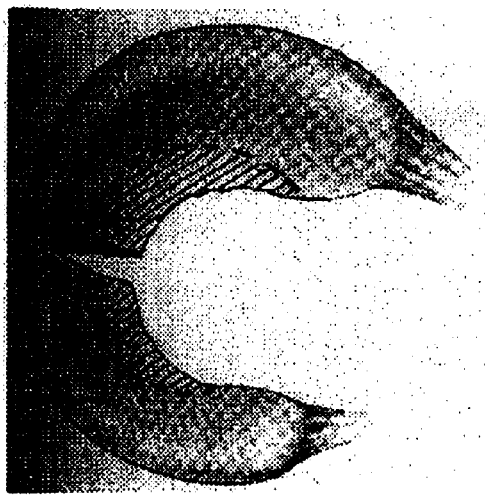
FIG. 1A shows a meniscal radial tear.

The present application generally relates to a product for repairing and/or regenerating cartilage lesions, and methods of repairing or regenerating cartilage lesions using such a product. The product and methods of the present invention are particularly useful for repairing defects (i.e., lesions) in articular cartilage (e.g., hyaline cartilage) and meniscal cartilage (e.g., fibrocartilage). When used to repair meniscal cartilage, the product and method of the present invention are effective for repairing both vascular and avascular meniscal cartilage lesions. In particular, the product and method of the present invention increase the rate of meniscus repair and induce more normal (i.e., endogenous-type) meniscal tissue than is commonly observed during the conventional repair practiced currently. The cartilage repair product of the present invention can also induce meniscus repair of avascular, "irreparable" tears and, furthermore, fill the defect with meniscus-like tissue. Moreover, the product and method are useful for repairing and regenerating meniscal tissue which has been removed by partial or complete meniscectomy. The product and method of the present invention can enhance blood vessel formation, produce fibrochondrocytes, induce cellular infiltration into the product, induce cellular proliferation, and produce cellular and spatial organization to form a three-dimensional meniscus tissue.

The ability of the product of the present invention to repair and/or regenerate both vascular and avascular cartilage in vivo has not been achieved by any of the presently known cartilage repair devices/compositions or methods. Moreover, previous devices and methods have been primarily directed to the repair of very small defects and have not been successful in solving problems associated with repair of large, clinically relevant defects. Without being bound by theory, the present inventors believe that the reason that these previous approaches failed to adequately repair cartilage is that they were not able to recapitulate natural cartilage ontogeny faithfully enough, this natural ontogeny being based on a very complicated system of different factors, factor combinations and factor concentrations with temporal and local gradients. A single recombinant factor or two recombinant factors may lack the inductive complexity to mimic cartilage development to a sufficient degree. Moreover, prior investigators had not discovered how to manipulate various combinations of osteogenic/chondrogenic factors in order to limit bone growth and enhance cartilage growth in vivo. Similarly, the system used to provide one or two recombinant factors may not have been able to mimic the gradient complexity of the natural system to a satisfactory degree or to maintain a factor concentration for a time that is sufficient to allow a full and permanent differentiation of precursor cells to chondrocytes. Without being bound by theory, the present inventors believe that the repair of certain defects, particularly large defects, requires the maintenance of a sufficient concentration of a particular complex mixture of repair factors at the site for a time sufficient to induce the proper formation of cartilage.

As discovered by the present inventors and as described herein, Bone Protein (BP) and mixtures derived from BP are chondrogenic in avascular environments (e.g. articular cartilage and in vitro), with limited osteogenic activity. However, although BP is chondrogenic in other, vascularized environments (lumbar spine, subcutaneous, etc.), it has significant osteogenic activity as well. Certain cartilage regeneration applications, such as the meniscus, require cartilaginous repair in a vascular environment. Because the meniscus is vascularized, it is therefore expected that BP and other bone-inducing molecules will induce bone formation during repair despite also inducing cartilage formation, which is not desirable for clinical applications. The present invention describes the identification of a novel mixture of factors derived from bovine bone to induce cartilage without bone formation. The cartilage induction activity was observed in a permissive bone-forming environment: the vascularized, rodent subcutaneous model. Specifically, this new mixture combines unexpectedly high concentrations of TGFβ proteins with the cartilage-inducing compositions disclosed herein, including mixtures that also have osteoinductive properties, to produce this novel chondrogenic activity with significantly reduced, or eliminated, osteogenic activity. To the present inventors' knowledge, prior to the present invention, the combination of high concentration TGFβ protein plus osteogenic and/or chondrogenic protein(s) to promote only cartilage formation in the absence of bone formation in a vascularized (permissive bone forming) environment, has not been described.

One aspect of the present invention is directed to a product for repair of cartilage lesions. In one embodiment, such a product includes: (a) a cartilage repair matrix; and, (b) a cartilage-inducing composition associated with the matrix for provision of a mixture of proteins, which can be referred to herein as chondrogenesis-enhancing proteins (described in detail below). According to the present invention, the phrase "cartilage-inducing composition" refers to a formulation which contains a mixture of different chondrogenesis-enhancing proteins and which enhances (i.e., augments, amplifies, improves, increases, or supplements) cartilage growth in vivo. In a preferred embodiment, the cartilage-inducing composition useful in the product of the present invention has an identifying characteristic which includes: an ability to induce cellular infiltration, an ability to induce cellular proliferation, an ability to induce angiogenesis, and/or an ability to induce cellular differentiation to type II collagen-producing chondrocytes, in vivo or under appropriate in vitro conditions.

More specifically, the cartilage-inducing composition of the present invention provides a mixture of proteins which includes proteins that have osteogenic- and/or chondrogenic-enhancing activities, particularly when combined into mixtures as described in detail herein. According to the present invention, the term "enhancing", particularly with regard to enhancing chondrogenesis, refers to any measure of augmenting, amplifying, improving, increasing, or supplementing a biological activity associated with chondrogenesis such that cartilage forms in a manner that more closely mimics the natural ontogeny of cartilage formation, as compared to cartilage formation that would occur in the absence of the product, or in the absence of the composition portion of the product. The term enhancing also means that endochondral maturation to mineralized cartilage and bone may be prevented or delayed.

In one embodiment of the present invention, a mixture of chondrogenesis-enhancing proteins that are included in a chondrogenesis-inducing composition can be characterized as being capable, when cultured together with ATDC5 cells for seven days at a concentration of about 100 ng/ml or less, of inducing a statistically significant increase in $A_{595}$ in an Alcian Blue assay performed with the ATDC5 cells. The specific conditions associated with such an ATDC5/Alcian Blue assay are described in detail below. It is noted that although the mixture of chondrogenesis-enhancing proteins has the above-described characteristic, an individual chondrogenesis-enhancing protein, when isolated from the other proteins in the mixture, is not necessarily chondrogenic. For example, as described below, a bone matrix protein such as osteocalcin is a chondrogenesis-enhancing protein according to the present invention, because when such protein is combined with other suitable proteins, such as combinations of TGFβ superfamily proteins as described herein, the mixture of proteins is capable of inducing a significant increase in $A_{595}$ in an ATDC5 Alcian Blue assay. Osteocalcin is not, however, chondrogenic in the absence of such TGFβ superfamily proteins.

Various embodiments of the chondrogenesis-inducing composition of the present invention are described in detail below. For general reference, however, the following description is provided. According to the present invention, the chondrogenesis-enhancing proteins in the cartilage-inducing composition of the present invention typically include at least two different members of the TGFβ superfamily proteins. In other embodiments, the chondrogenesis-enhancing proteins include at least three different members of the TGFβ superfamily proteins, and in alternative embodiments, at least four, five, six, seven, eight, nine, and most preferably ten different members of the TGFβ superfamily proteins. As used herein, a "TGFβ superfamily protein" can be any protein of the art-recognized superfamily of extracellular signal transduction proteins that are structurally related to TGFβ1–5. Preferably, a TGFβ superfamily protein suitable for use in the present invention includes, but is not limited to the following proteins: TGFβ1, TGFβ2, TGFβ3, TGFβ4, TGFβ5, bone morphogenetic protein (BMP)-2, BMP-3, BMP-4, BMP-5, BMP-6, BMP-7, BMP-8, BMP-9, cartilage-derived morphogenetic protein (CDMP)-1, CDMP-2, and/or CDMP-3. More preferably, the chondrogenesis-enhancing proteins useful in the composition of the present invention include, but are not limited to: TGFβ1, TGFβ2, TGFβ3, BMP-2, BMP-3, BMP-4, BMP-5, BMP-6, BMP-7, and/or CDMP (CDMP-1, CDMP-2, and/or CDMP-3).

In some aspects of the present invention, the cartilage-inducing composition of the present invention can include at least one bone matrix protein and/or at least one growth factor protein. In a preferred aspect, the mixture of proteins includes at least one bone matrix protein and at least one growth factor protein. In a more preferred embodiment, the chondrogenesis-enhancing proteins include, in increasing preference, at least two, three, four, and most preferably five different bone matrix proteins, and/or at least two growth factor proteins.

As used herein, "bone matrix proteins" are any of a group of proteins known in the art to be a component of or associated with the minute collagenous fibers and ground substances which form bone matrix. As used herein, a bone matrix protein is not a member of the TGFβ superfamily as described herein, nor a growth factor protein as described herein. Bone matrix proteins can include, but are not limited to, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and/or fibronectin. Preferably, bone matrix proteins suitable for use with the product of the present invention include one or more of: osteocalcin, osteonectin, MGP, TSP, BSP, lysyloxidase and cathepsin L pre. In one embodiment, the at least one bone matrix protein includes at least osteocalcin, osteonectin, BSP, lysyloxidase and cathepsin L pre. A particularly preferred bone matrix protein is MGP, and more preferred is osteonectin, and most preferred is TSP.

As used herein, "growth factor proteins" are any of a group of proteins characterized as an extracellular polypeptide signaling molecule that stimulates a cell to grow or proliferate. Such growth factors may also have other actions besides the induction of cell growth or proliferation. As used herein, a growth factor is not a member of the TGFβ superfamily as defined herein nor is it a bone matrix protein as defined herein. Preferably, growth factor proteins suitable for use with the product of the present invention include one or more of: fibroblast growth factor I (FGF-I), FGF-II, FGF- 9, leukocyte inhibitory factor (LIF), insulin, insulin growth factor I (IGF-I), IGF-II, platelet-derived growth factor AA (PDGF-AA), PDGF-BB, PDGF-AB, stromal derived factor-2 (SDF-2), pituitary thyroid hormone (PTH), growth hormone, hepatocyte growth factor (HGF), epithelial growth factor (EGF), transforming growth factor-α (TGFα) and hedgehog proteins. A most preferred growth factor protein for use with the product of the present invention is FGF-I.

In one aspect of the present invention, the mixture of proteins in the chondrogenesis-inducing composition can also include one or more serum proteins. As used herein, serum proteins are any of a group of proteins that is a component of serum. A serum protein is not a member of the TGFβ superfamily, a bone matrix protein or a growth factor, as described herein. In one embodiment, chondrogenesis-inducing compositions include, in increasing preference, at least one, two, three, and most preferably four different serum proteins. Serum proteins suitable for use with the product of the present invention include one or more of albumin, transferrin, α2-Hs GlycoP, IgG, α1-antitrypsin, β2-microglobulin, Apo A1 lipoprotein (LP) and Factor XIIIb. Preferably, serum proteins suitable for use with the product of the present invention include one or more of albumin, transferrin, Apo A1 LP and Factor XIIIb.

In one aspect of the present invention, the relative proportions of the proteins in the mixture of proteins are any proportions which are sufficient for the mixture, at a concentration of 100 ng/ml or less, to induce a statistically significant increase in $A_{595}$ in an Alcian Blue assay performed with ATDC5 cells as described below. In one embodiment, the percentage of TGFβ superfamily members within the mixture ranges between about 0.1% to about 99.99% of the total mixture, and preferably between about 0.5% to about 99.99% of the total mixture, and more preferably between about 0.1% to about 50% of the total mixture, and more preferably between about 0.5% to about 50% of the total mixture, and more preferably, between about 0.5% and about 25%, and even more preferably, between about 1% and about 10% of the total mixture. The percentage of growth factors within the mixture ranges between about 0.01% to about 50% of the total mixture, and preferably, between about 0.05% and about 25%, and even more preferably, between about 0.1% and about 10% of the total mixture. The percentage of serum and bone matrix protein components, either separately or combined, ranges between about 20% to about 98%, and preferably between about 40% to about 98%, and even more preferably between about 80% to about 98%. In one embodiment of the invention, the mixture of chondrogenesis-inducing proteins contains at least BMP-3, BMP-2 and TGFβ1, wherein the quantity of BMP-3 in the mixture is about 2–6 fold greater than the quantity of BMP-2 and about 10–30 fold greater than the quantity of TGFβ1 in the mixture. Unless otherwise specified, reference to percentages of proteins or ratios of proteins either to the mixture of proteins or to specific proteins is based on weight to weight (w/w).

Having generally discussed certain aspects of mixtures of proteins which may be present in a chondrogenesis-inducing composition of the present invention, particular preferred embodiments of such a composition are described below.

In a first embodiment of the present invention, a cartilage-inducing composition includes a mixture of proteins which includes: transforming growth factor β1 (TGFβ1), bone morphogenetic protein (BMP)-2, BMP-3, and BMP-7. The quantity of the TGFβ1 in the mixture is typically from about 0.01% to about 99.99% of total proteins in the mixture. The quantity of the BMP-2 in the mixture is typically from about 0.01% to about 10% of total proteins in the mixture, or from about 0.01 to about 1%, or from about 0.01 to about 0.1%, or from about 0.1 to about 1%, or from about 0.1 to about 10% of total proteins. The quantity of the BMP-3 in the mixture is typically from about 0.1% to about 15% of total proteins in the mixture, or from about 0.1 to about 1%, or from about 0.01 to about 15%, or from about 0.01 to about 1%, or from about 0.01 to about 0.1%. The quantity of the BMP-7 in the mixture is typically from about 0.01% to about 10% of total proteins in the mixture, or from about 0.01 to about 1%, or from about 0.01 to about 0.1%, or from about 0.1 to about 1%, or from about 0.1 to about 10% of total proteins. The amino acid and nucleic acid sequence for each of the above-referenced proteins are known in the art and can be publicly accessed, for example, through a database such as GenBank. Additionally, these proteins can be purified, if desired, from an appropriate source, such as demineralized bone. For example, high purity TGFβ-1 can be isolated from bovine bone using methods disclosed by Seyedin (Ogawa et al., Meth. Enzymol., 198:317–327 (1991); Seyedin et al., PNAS, 82:2267–71 (1985)).

In one aspect of this embodiment of the present invention, the mixture of proteins comprises TGFβ superfamily proteins: TGFβ1, bone morphogenetic protein (BMP)-2, BMP-3, and BMP-7, wherein the TGFβ superfamily proteins comprise from about 0.5% to about 99.99% of the mixture of proteins. Alternatively, the TGFβ superfamily proteins can be present at a percentage of from about 0.5% to about 25% of the mixture of proteins, or from about 1% to about 10% of the mixture of proteins.

As discussed above, mixtures of proteins according to the present invention that are capable of inducing significant chondrogenesis in vivo may have a relatively low percentage of TGFβ proteins, and particularly TGFβ1, relative to the total amount of protein in the mixture of proteins (e.g., from about 0.01 to about 1%). However, the present inventors have discovered that the use of unexpectedly high concentrations of a TGFβ protein, and particularly, TGFβ1, relative to the total mixture of proteins of the present invention, results in enhanced induction of chondrogenesis in vivo, with significantly reduced osteogenesis. This discovery is particularly important for in vivo chondrogenesis-induction in a vascular, or bone-forming, environment, and will significantly improve the clinical performance of compositions of the present invention in such in vivo environments. A mixture of proteins in this embodiment of the present invention can therefore include a quantity of TGFβ1 which is from about 0.01% to about 99.99% of the total quantity of proteins in the mixture, with increasing TGFβ1 relative to the total amount of protein resulting in enhanced chondrogenesis. In other embodiments, the quantity of TGFβ1 is from about 0.01% to about 75% of total proteins in the mixture, from about 0.01% to about 50% of total proteins in the mixture, from about 0.01% to about 25% of total proteins in the mixture, from about 0.01% to about 10% of total proteins in the mixture, or from about 0.1% to about 1% of total proteins in the mixture. In a preferred embodiment, the quantity of TGFβ1 is at least about 33% of total proteins in the mixture (up to a maximum of about 99.99%). In another preferred embodiment, the quantity of TGFβ1 is at least about 50% of total proteins in the mixture (up to a maximum of about 99.99%).

Alternatively, the amount of TGFβ1 to be added to the mixture of proteins can be determined as a ratio. In one embodiment, the ratio of TGFβ1 to all other proteins in the mixture of proteins is at least about 1:10. Preferably, the ratio of TGFβ1 to all other proteins in the mixture of proteins is at least about 1:3, and more preferably, at least about 1:1, and even more preferably, at least about 10:1. Examples of the use of TGFβ1 at aratio of 1:10, 1:3 and 1:1 relative to the total quantity of protein in the mixture in vivo is demonstrated in Example 15. Example 15 demonstrates that unexpectedly high concentrations of TGFβ protein relative to the total protein results in significantly enhanced chondrogenesis and significantly decreased osteogenesis. The optimal amount of TGFβ1 to be added for a given mixture of proteins, cartilage repair matrix, and in vivo environment (i.e., vascular or avascular) can be determined, for example, by using a simple rat subcutaneous assay as described in detail in the examples section (e.g., see Example 14).

In yet another embodiment, the amount of TGFβ proteins such as TGFβ1 to be included in the mixture of proteins can be determined as an amount of TGFβ protein in excess of one or the total of BMP proteins in the mixture. In a preferred embodiment, the amount of TGFβ protein should be greater than 10× higher than the amount of BMP (one or a combination of BMPs in the mixture), but less than 100× higher than the amount of BMP in the mixture.

The quantity of the BMP-2 in the mixture is typically from about 0.01% to about 10% of total proteins in the mixture, or from about 0.01 to about 1%, or from about 0.01 to about 0.1%, or from about 0.1 to about 1%, or from about 0.1 to about 10%, and in one embodiment, is present in a quantity of from about 0.1% to about 5% of total proteins in the mixture. The quantity of BMP-3 in the mixture is typically from about 0.01% to about 15% of total proteins in the mixture, or from about 0.01 to about 1%, or from about 0.01 to about 0.1%, or from about 0.1 to about 1%, or from about 0.1 to about 15%, and in one embodiment, is present in a quantity of from about 0.1% to about 10% of total proteins in the mixture, and in another embodiment, is present in a quantity of from about 0.1% to about 5% of total proteins in the mixture. The quantity of BMP-7 in the mixture is typically from about 0.01% to about 10% of total proteins in the mixture, or from about 0.01 to about 1%, or from about 0.01 to about 0.1%, or from about 0.1 to about 1%, or from about 0.1 to about 10%, and in one embodiment, can be present in a quantity of from about 0.1% to about 5% of total proteins in the mixture.

In one aspect of this embodiment of the present invention, the mixture of proteins further includes one or more of the following TGFβ superfamily proteins: TGFβ2, TGFβ3, BMP-4, BMP-5, BMP-6, BMP-8, BMP-9, and cartilage-derived morphogenetic protein (CDMP), which can include one or more of CDMP-1, CDMP-2 or CDMP-3. The quantity of TGFβ2 in such a mixture is typically from about 0.5% to about 12% of the total mixture of proteins, although additional TGFβ2 can be added to enhance the chondrogenic activity of the mixture of proteins, if desired, up to as much as about 99.99% of the total mixture of proteins. The quantity of TGFβ3 in such a mixture is typically from about 0.01% to about 15% of the total mixture of proteins, although additional TGFβ3 can be added to enhance the chondrogenic activity of the mixture of proteins, if desired, up to as much as about 99.99% of the total mixture of proteins. The quantity of BMP-4 in such a mixture typically comprises from about 0.01% to about 1% of the total mixture of proteins, although additional BMP-4 can be added to enhance the chondrogenic activity of the mixture of proteins, if desired, up to as much as about 10% of the total mixture of proteins. The quantity of BMP-5 in the mixture of proteins is typically from about 0.01% to about 1% of the total mixture of proteins, although additional BMP-5 can be added to enhance the chondrogenic activity of the mixture of proteins, if desired, up to as much as about 10% of the total mixture of proteins. The quantity of BMP-6 in the mixture of proteins is typically from about 0.01% to about 1% of the total mixture of proteins, although additional BMP-6 can be added to enhance the chondrogenic activity of the mixture of proteins, if desired, up to as much as about 10% of the total mixture of proteins. The quantity of CDMP in the mixture of proteins is typically from about 0.01% to about 1% of the total mixture of proteins, although additional CDMP can be added to enhance the chondrogenic activity of the mixture of proteins, if desired, up to as much as about 10% of the total mixture of proteins.

In one aspect of this embodiment, the mixture of proteins can additionally include at least one bone matrix protein. Bone matrix proteins are generally described above. Preferred bone matrix proteins for use in this mixture of proteins include, but are not limited to, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and fibronectin. More preferably, bone matrix proteins suitable for use in this mixture of proteins include, but are not limited to, osteocalcin, osteonectin, bone sialoprotein (BSP), lysyloxidase, and cathepsin L pre. The bone matrix proteins are typically present in the mixture in a quantity from about 20% to about 98% of the total mixture of proteins. In one embodiment, the bone matrix proteins are present in the mixture in a quantity from about 40% to about 98% of the total mixture of proteins.

In another aspect of this embodiment, the mixture of proteins can additionally include at least one growth factor protein. Growth factor proteins are generally described above. Preferred growth factor proteins for use in this mixture of proteins include, but are not limited to, fibroblast growth factor-I (FGF-I), FGF-II, FGF-9, leukocyte inhibitory factor (LIF), insulin, insulin growth factor I (IGF-I), IGF-II, platelet-derived growth factor AA (PDGF-AA), PDGF-BB, PDGF-AB, stromal derived factor-2 (SDF-2), pituitary thyroid hormone (PTH), growth hormone, hepatocyte growth factor (HGF), epithelial growth factor (EGF), transforming growth factor-α (TGFα) and hedgehog proteins. A particularly preferred growth factor for use in this mixture of the present invention is FGF-I. Typically, the growth factor protein is present in the mixture of proteins at a quantity from about 0.01% to about 50% of the total mixture of proteins. In other embodiments, the quantity of growth factor proteins in the mixture is from about 0.5% to about 25% of the total mixture of proteins; or from about 0.1% to about 10% of the total mixture of proteins. When the growth factor is FGF-I, the quantity of FGF-I in the mixture of proteins is typically from about 0.001% to about 10% of the total mixture of proteins.

In yet another aspect of this embodiment, the mixture of proteins can include one or more serum proteins. Serum proteins have been generally described above. Preferably, serum proteins useful in this mixture include, but are not limited to, albumin, transferrin, α2-Hs GlycoP, IgG, α1-antitrypsin, β2-microglobulin, Apo A1 lipoprotein (LP) and/or Factor XIIIb. More preferably, serum proteins useful in this mixture include, but are not limited to, albumin, transferrin, Apo A1 LP and/or Factor XIIIb.

In one aspect of this embodiment of the present invention, a mixture of proteins suitable for use in a chondrogenesis-inducing composition portion of a cartilage repair product of the present invention includes the following proteins: TGFβ1, TGFβ2, TGFβ3, BMP-2, BMP-3, BMP-4, BMP-5, BMP-6, BMP-7, CDMP, FGF-I, osteocalcin, osteonectin, BSP, lysyloxidase, cathepsin L pre, albumin, transferrin, Apo A1 LP and Factor XIIIb. In yet another embodiment, a suitable mixture of chondrogenesis-enhancing proteins includes the mixture of proteins referred to herein as Bone Protein (BP), which is defined herein as a partially-purified protein mixture from bovine long bones as described in Poser and Benedict, WO 95/13767, incorporated herein by reference in its entirety. As described in Poser and Benedict, WO 95/13767: "Bone growth factor was isolated from the cortical diaphyses of bovine long bones. The marrow and soft tissue was cleaned from the long bones, and the bones were pulverized and demineralized in 1.0 normal (N) hydrochloric acid at a 1:13 weight to volume ratio for 16 hours at 25° C. The bone particles were washed in distilled water and then extracted in a buffered solution comprising of 4 N guanidine hydrochloride buffered with 0.1 N Tris, pH 7.6 at a concentration of 3 milliliters of buffered solution per gram of original powdered bone. The bone was extracted for 48 h at 15° C. The extracted bone particles were then passed through a series of chromatographic purification steps as described in U.S. application Ser. No. 07/689,459 to extract bone growth factor having bone inductive effect at doses less than 35 microgram (μg)."

In another aspect of this embodiment of the present invention, the cartilage inducing composition has an identifying characteristic selected from the group consisting of an ability to induce cellular infiltration, an ability to induce cellular proliferation, an ability to induce angiogenesis, and an ability to induce cellular differentiation to type II collagen-producing chondrocytes. In yet another aspect of this embodiment of the present invention, the mixture of proteins, when used at a concentration of at least about 10 μg per 6.5–7.3 mg of bovine tendon collagen in a rat subcutaneous assay, induces a bone score of from about 1.0 to about 3.5, using a bone grading scale set forth in Table 8 (Example 10), and induces a cartilage score of at least about 1.2, using a cartilage grading scale set forth in Table 9 (Example 10). A rat subcutaneous assay suitable for determining bone and cartilage scores according to this aspect, and the grading scales of Tables 8 and 9 are described in detail in the Examples Section.

In a second embodiment of the present invention, a cartilage-inducing composition includes a mixture of proteins which includes (a) a bone-derived osteogenic or chondrogenic formulation; and, (b) an exogenous TGFβ protein. The exogenous TGFβ protein is present in an amount sufficient to increase cartilage induction by the composition over a level of cartilage induction by the bone-derived osteogenic or chondrogenic protein formulation in the absence of the exogenous TGFβ protein. According to the present invention, a "bone-derived osteogenic or chondrogenic formulation" refers to any mixture of proteins containing a complex mixture of proteins which is isolated, or derived, (e.g., by at least one, and typically, multiple purification steps) from a starting material of bone, and which is osteogenic or chondrogenic in vivo. A bone-derived osteogenic or chondrogenic formulation contains at least one bone morphogenetic protein (BMP) and the ratio of exogenous TGFβ to the BMP (or more than one BMP) in the mixture is greater than about 10:1. The BMP protein can include any BMP protein, including, but not limited to, BMP-2, BMP-3, BMP-4, BMP-5, BMP-6, BMP-7, BMP-8, BMP-9, CDMP, and mixtures thereof. Preferably, the bone-derived formulation is capable of inducing bone and/or cartilage formation in an in vivo rat subcutaneous assay such as that described in the Examples section of the Rosen modified Sampath-Reddi rodent assay (Sampath et al., Proc. Nat'l Acad. Sci. USA, 80(21):6591–5 (1983)). More preferably, the bone-derived formulation is capable of inducing a bone score of at least about 1.0 when used at a concentration of at least about 10 μg per 6.5–7.3 mg of bovine tendon collagen in a rat subcutaneous assay as set forth in Example 10 using a bone grading scale set forth in Table 8 (Example 10), and/or induces a cartilage score of at least about 1.0 under the same conditions, using a cartilage grading scale set forth in Table 9 (Example 10). Without being bound by theory, the present inventors believe that given their discovery described herein of the enhanced chondrogenic effects on osteogenic or chondrogenic protein mixtures of significantly high levels of TGFβ protein, it is likely that even protein mixtures that have strong osteogenic activity and little or no chondrogenic activity in the absence of excess (exogenous) TGFβ protein can be converted to chondrogenic mixtures by the addition of high dose TGFβ protein, and particularly, TGFβ1. Particularly preferred bone-derived osteogenic or chondrogenic formulations for use in this embodiment of the present invention include Bone Protein (BP) and subfractions and related derivatives thereof. The Examples Section describes examples of BP (Example 9), subfractions thereof (Example 12) and related derivatives thereof (Example 11).

The starting material of bone can be a bone sample from any source, including, but not limited to, bovine bone and human bone. The bone can be processed by any of a number of methods known in the art for producing compositions which have osteogenic activity, alone or in combination with some level of chondrogenic activity (See for example, U.S. Pat. No. 4,563,489 to Urist; U.S. Pat. No. 5,629,009 to Laurencin et al.; PCT Publication No. WO 92/09697 to Bentz et al.; and Poser and Benedict, PCT Publication No. WO95/13767). According to the present invention, a "bone-derived osteogenic or chondrogenic formulation" is not used to refer to mixtures of one or more recombinant proteins, since recombinant proteins are not produced using bone as a starting material.

For example, one method for producing Bone Protein according to the present invention, and as described, for example, in U.S. Pat. No. 5,290,763, entitled "Osteoinductive Protein Mixtures and Purification Processes", incorporated herein by reference in its entirety, typically includes the steps of conducting anion exchange chromatography on a demineralized bone extract solution, a cation exchange procedure, and reverse phase HPLC procedure.

According to the present invention, an "exogenous TGFβ protein" refers to a TGFβ protein that is in substantially pure form and which is not a part of the bone-derived osteogenic or chondrogenic formulation of proteins (i.e., the exogenous TGFβ protein was not isolated from with the bone-derived osteogenic or chondrogenic formulation of proteins). The exogenous TGFβ protein is instead added to the formulation as an additional protein from a different source. It is to be understood that the bone-derived osteogenic or chondrogenic formulation of proteins can contain TGFβ proteins (i.e., "endogenous" proteins), since such mixtures typically do contain at least TGFβ1 and TGFβ2. However, the second component in the composition of exogenous TGFβ protein is intended as a means of increasing the total amount of TGFβ protein in the composition beyond what is naturally found in bone and mixtures derived therefrom. Specifically, the TGFβ protein is provided in an amount that is sufficient to increase cartilage induction (i.e., in vivo) by the composition over a level of cartilage induction (i.e., in vivo under the same conditions) by the bone-derived osteogenic or chondrogenic protein formulation in the absence of the exogenous TGFβ protein. The exogenous TGFβ protein can be recombinant TGFβ protein or substantially purified TGFβ protein from any suitable source, such as bone. Recombinant TGFβ proteins are publicly available and TGFβ proteins can be purified to high purity from bone, for example, using previously described methods (Ogawa et al., Meth. Enzymol., 198:317–327 (1991); Seyedin et al., PNAS, 82:2267–71 (1985). The exogenous TGFβ protein can be any TGFβ protein, including TGFβ1, TGFβ2, TGFβ3, TGFβ4, TGFβ5, or mixtures thereof. In a preferred embodiment, the TGFβ protein is TGFβ1 or TGFβ2, with TGFβ1 being most preferred.

Preferably, the ratio of the TGFβ protein to the at least one BMP protein in the mixture (w/w), is greater than about 10:1, and in one aspect, is greater than about 100:1, and in another aspect, is greater than about 1000:1, and in another aspect, is greater than about 10,000:1. In one embodiment, the ratio of TGFβ protein to total BMP proteins in the mixture of proteins is greater than 10:1, and in another aspect, is greater than about 100:1, and in another aspect, is greater than about 1000:1, and in another aspect, is greater than about 10,000:1. It is noted that the percentages of various components in a mixture of proteins will adjust according to the amount of excess TGFβ added, and in some embodiments, including where very high concentrations of TGFβ are added, the percentage of a BMP as a total of the composition, for example, may fall significantly below the more typical amount of BMP in the mixture.

In one aspect of this embodiment of the present invention, the mixture of proteins, which includes both the bone-derived osteogenic or chondrogenic formulation of proteins and the exogenous TGFβ protein, comprises TGFβ superfamily proteins: TGFβ1, bone morphogenetic protein (BMP)-2, BMP-3, and BMP-7, wherein the TGFβ superfamily proteins comprise from about 0.5% to about 99.99% of the mixture of proteins. Alternatively, the TGFβ superfamily proteins can be present at a percentage of from about 0.5% to about 25% of the mixture of proteins, or from about 1% to about 10% of the mixture of proteins. In this embodiment of the present invention, a TGFβ protein can be provided by the bone-derived osteogenic or chondrogenic formulation and/or the exogenous source of TGFβ. All other proteins are typically provided by the bone-derived osteogenic or chondrogenic formulation, although other exogenous proteins may be added to the mixture to further enhance the chondrogenic properties of the composition, if desired.

A mixture of proteins in this embodiment of the present invention can therefore include a quantity of TGFβ1 which is from about 0.01% to about 99.99% of the total quantity of proteins in the mixture, with increasing TGFβ1 relative to the total amount of protein resulting in enhanced chondrogenesis. In other embodiments, the quantity of TGFβ1 is from about 0.01% to about 75% of total proteins in the mixture, from about 0.01% to about 50% of total proteins in the mixture, from about 0.01% to about 25% of total proteins in the mixture, from about 0.01% to about 10% of total proteins in the mixture, or from about 0.1% to about 1% of total proteins in the mixture. Typically, the bone-derived osteogenic or chondrogenic formulation will contribute from about 0.01% to about 1% TGFβ1 protein to the mixture, with higher amounts being contributed by the exogenous TGFβ1. In a preferred embodiment, the quantity of TGFβ1 is at least about 33% of total proteins in the mixture (up to a maximum of about 99.99%). In another preferred embodiment, the quantity of TGFβ1 is at least about 50% of total proteins in the mixture (up to a maximum of about 99.99%).

Alternatively, the amount of TGFβ1 to be added to the mixture of proteins can be determined as a ratio. In one embodiment, the ratio of TGFβ1 to all other proteins in the mixture of proteins is at least about 1:10 (with the ratio of TGFβ protein to at least one BMP being greater than about 10:1). Preferably, the ratio of TGFβ1 to all other proteins in the mixture of proteins is at least about 1:3, and more preferably, at least about 1:1, and even more preferably, at least about 10:1.

In yet another embodiment, the amount of TGFβ proteins such as TGFβ1 to be included in the mixture of proteins can be determined as an amount of TGFβ protein in excess of one or the total of BMP proteins in the mixture. In a preferred embodiment, the amount of TGFβ protein should be greater than 10× higher than the amount of BMP (one or a combination of BMPs in the mixture), but less than 100× higher than the amount of BMP in the mixture.

The quantity of the BMP-2 in the mixture is typically from about 0.1% to about 5% of total proteins in the mixture, or from about 0.01 to about 1%, or from about 0.01 to about 0.1%, or from about 0.1 to about 1%, although the percentage of BMP-2 can be less than 0.01% of the total proteins when high concentrations of TGFβ proteins are added (e.g., when the ratio of TGFβ protein to BMP is greater than 10,000:1). The quantity of BMP-3 in the mixture is typically from about 0.1% to about 5% of total proteins in the mixture, or from about 0.01 to about 1%, or from about 0.01 to about 0.1%, or from about 0.1 to about 1%, although the percentage of BMP-3 can be less than 0.01% of the total proteins when high concentrations of TGFβ proteins are added. The quantity of BMP-7 in the mixture is typically from about 0.1% to about 5% of total proteins in the mixture, or from about 0.01 to about 1%, or from about 0.01 to about 0.1%, or from about 0.1 to about 1%, although the percentage of BMP-7 can be less than 0.01% of the total proteins when high concentrations of TGFβ proteins are added.

In one aspect of this embodiment of the present invention, the mixture of proteins further includes one or more of the following TGFβ superfamily proteins: TGFβ2, TGFβ3, BMP-4, BMP-5, BMP-6, BMP-8, BMP-9, and cartilage-derived morphogenetic protein (CDMP), which can include one or more of CDMP-1, CDMP-2 or CDMP-3. The quantity of TGFβ2 in the bone-derived osteogenic or chondrogenic formulation is typically from about 0.5% to about 12–15% of the total formulation, although additional TGFβ2 can be added as an exogenous TGFβ protein to enhance the chondrogenic activity of the mixture of proteins, if desired, up to as much as about 99.99% of the total mixture of proteins. The quantity of TGFβ3 in the bone-derived osteogenic or chondrogenic formulation is typically from about 0.01% to about 15% of the total formulation, although additional TGFβ3 can be added to enhance the chondrogenic activity of the mixture of proteins, if desired, up to as much as about 99.99% of the total mixture of proteins. The quantity of BMP-4 in the bone-derived osteogenic or chondrogenic formulation typically comprises from about 0.01% to about 1% of the total formulation, although additional BMP-4 can be added to enhance the chondrogenic activity of the mixture of proteins. In some embodiments, the percentage of BMP-4 can be less than 0.01% of the total proteins when high concentrations of TGFP proteins are added (e.g., when the ratio of TGFβ to BMP is greater than 10,000:1). The quantity of BMP-5 in the bone-derived osteogenic or chondrogenic formulation is typically is from about 0.01% to about 1% of the total formulation, although additional BMP-5 can be added to enhance the chondrogenic activity of the mixture of proteins. In some embodiments, the percentage of BMP-5 can be less than 0.01% of the total proteins when high concentrations of TGFβ proteins are added (e.g., when the ratio of TGFβ to BMP is greater than 10,000:1). The quantity of BMP-6 in the bone-derived osteogenic or chondrogenic formulation is typically from about 0.01% to about 1% of the total formulation, although additional BMP-6 can be added to enhance the chondrogenic activity of the mixture of proteins. In some embodiments, the percentage of BMP-6 can be less than 0.01% of the total proteins when high concentrations of TGFβ proteins are added (e.g., when the ratio of TGFβ to BMP is greater than 10,000:1). The quantity of CDMP in the bone-derived osteogenic or chondrogenic formulation is typically from about 0.01% to about 1% of the total formulation, although additional CDMP can be added to enhance the chondrogenic activity of the mixture of proteins. In some embodiments, the percentage of CDMP can be less than 0.01% of the total proteins when high concentrations of TGFβ proteins are added (e.g., when the ratio of TGFβ to BMP is greater than 10,000:1).

In one aspect of this embodiment, the mixture of proteins can additionally include at least one bone matrix protein, typically provided by the bone-derived osteogenic or chondrogenic formulation. Bone matrix proteins are generally described above. Preferred bone matrix proteins for use in this mixture of proteins include, but are not limited to, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and fibronectin. More preferably, bone matrix proteins suitable for use in this mixture of proteins include, but are not limited to, osteocalcin, osteonectin, bone sialoprotein (BSP), lysyloxidase, and cathepsin L pre. The bone matrix proteins are typically present in the mixture in a quantity from about 20% to about 98% of the total mixture of proteins. In one embodiment, the bone matrix proteins are present in the mixture in a quantity from about 40% to about 98% of the total mixture of proteins.

In another aspect of this embodiment, the mixture of proteins can additionally include at least one growth factor protein. Growth factor proteins are generally described above. Preferred growth factor proteins for use in this mixture of proteins include, but are not limited to, fibroblast growth factor-I (FGF-I), FGF-II, FGF-9, leukocyte inhibitory factor (LIF), insulin, insulin growth factor I (IGF-I), IGF-II, platelet-derived growth factor AA (PDGF-AA), PDGF-BB, PDGF-AB, stromal derived factor-2 (SDF-2), pituitary thyroid hormone (PTH), growth hormone, hepatocyte growth factor (HGF), epithelial growth factor (EGF), transforming growth factor-α (TGFα) and hedgehog proteins. A particularly preferred growth factor for use in this mixture of the present invention is FGF-I. Typically, the growth factor protein are present in the mixture of proteins at a quantity from about 0.01% to about 50% of the total mixture of proteins. In other embodiments, the quantity of growth factor proteins in the mixture is from about 0.5% to about 25% of the total mixture of proteins; or from about 0.1% to about 10% of the total mixture of proteins. When the growth factor is FGF-I, the quantity of FGF-I in the mixture of proteins is typically from about 0.001% to about 10% of the total mixture of proteins.

In yet another aspect of this embodiment, the mixture of proteins can include one or more serum proteins. Serum proteins have been generally described above. Preferably, serum proteins useful in this mixture include, but are not limited to, albumin, transferrin, α2-Hs GlycoP, IgG, α1-antitrypsin, β2-microglobulin, Apo A1 lipoprotein (LP) and/or Factor XIIIb. More preferably, serum proteins useful in this mixture include, but are not limited to, albumin, transferrin, Apo A1 LP and/or Factor XIIIb.

In one aspect of this embodiment of the present invention, a mixture of proteins suitable for use in a chondrogenesis-inducing composition portion of a cartilage repair product of the present invention includes the following proteins: TGFβ1, TGFβ2, TGFβ3, BMP-2, BMP-3, BMP-4, BMP-5, BMP-6, BMP-7, CDMP, FGF-I, osteocalcin, osteonectin, BSP, lysyloxidase, cathepsin L pre, albumin, transferrin, Apo A1 LP and Factor XIIIb. In yet another embodiment, a suitable mixture of chondrogenesis-enhancing proteins includes the mixture of proteins referred to herein as Bone Protein (BP), which is defined herein as a partially-purified protein mixture from bovine long bones as described in Poser and Benedict, WO 95/13767, incorporated herein by reference in its entirety. In another aspect of this embodiment of the present invention, the cartilage inducing composition has an identifying characteristic selected from the group consisting of an ability to induce cellular infiltration, an ability to induce cellular proliferation, an ability to induce angiogenesis, and an ability to induce cellular differentiation to type II collagen-producing chondrocytes.

Preferably, in this embodiment, the composition, when used at a concentration of at least about 10 μg per 6.5–7.3 mg of bovine tendon collagen in a rat subcutaneous assay, induces a bone score of less than about 2.0, using a bone grading scale set forth in Table 8, and induces a cartilage score of at least about 2.0, using a cartilage grading scale set forth in Table 9. More preferably, the composition, when used at a concentration of at least about 10 μg per 6.5–7.3 mg of bovine tendon collagen in arat subcutaneous assay, induces a bone score of less than about 2.0, using a bone grading scale set forth in Table 8, and induces a cartilage score of at least about 2.5, using a cartilage grading scale set forth in Table 9. Even more preferably, the composition, when used at a concentration of at least about 10 μg per 6.5–7.3 mg of bovine tendon collagen in a rat subcutaneous assay, induces a bone score of less than about 2.0, using a bone grading scale set forth in Table 8, and induces a cartilage score of at least about 3.0, using a cartilage grading scale set forth in Table 9.

In a third embodiment of the product of the present invention, a cartilage-inducing composition includes a mixture of proteins comprising: (a) a TGFβ protein; and, (b) at least one bone morphogenetic protein (BMP), wherein the ratio of the TGFβ protein to the BMP protein is greater than about 10:1. In this embodiment, the TGFβ protein can be any TGFβ protein, including TGFβ1, TGFβ2, TGFβ3, TGFβ4, TGFβ5, or mixtures thereof. In a preferred embodiment, the TGFβ protein is TGFβ1 or TGFβ2, with TGFβ1 being most preferred. The BMP protein can be any BMP protein, including, but not limited to, BMP-2, BMP-3, BMP-4, BMP-5, BMP-6, BMP-7, BMP-8, BMP-9, CDMP, and mixtures thereof.

Preferably, the ratio of the TGFβ protein to the at least one BMP protein in the mixture (w/w), is greater than about 10:1, and in one aspect, is greater than about 100:1, and in another aspect, is greater than about 1000:1, and in another aspect, is greater than about 10,000:1. In one embodiment, the ratio of TGFβ protein to total BMP proteins in the mixture of proteins is greater than 10:1, and in another aspect, is greater than about 100:1, and in another aspect, is greater than about 1000:1, and in another aspect, is greater than about 10,000:1. It is noted that the percentages of various components in a mixture of proteins will adjust according to the amount of excess TGFβ added, and in some embodiments, including where very high concentrations of TGFβ are added, the percentage of a BMP as a total of the composition, for example, may fall significantly below the more typical amount of BMP in the mixture.

In yet another embodiment, the amount of TGFβ proteins such as TGFβ1 to be included in the mixture of proteins can be determined as an amount of TGFβ protein in excess of one or the total of BMP proteins in the mixture. In a preferred embodiment, the amount of TGFβ protein should be greater than 10× higher than the amount of BMP (one or a combination of BMPs in the mixture), but less than 100× higher than the amount of BMP in the mixture.

According to this embodiment of the present invention, the TGFβ protein and the at least one BMP protein can be provided as a recombinant protein, as a substantially pure protein, or as a component of a mixture of proteins, such as a component of a bone-derived osteogenic or chondrogenic formulation as described in the embodiment above.

Although in this embodiment, the mixture of proteins can include as few as one TGFβ protein and one BMP protein, in one aspect of this embodiment of the present invention, the mixture of proteins comprises TGFβ superfamily proteins: TGFβ1, bone morphogenetic protein (BMP)-2, BMP-3, and BMP-7, wherein the TGFβ superfamily proteins comprise from about 0.5% to about 99.99% of the mixture of proteins. Alternatively, the TGFβ superfamily proteins can be present at a percentage of from about 0.5% to about 25% of the mixture of proteins, or from about 1% to about 10% of the mixture of proteins.

A mixture of proteins in this embodiment of the present invention can include a quantity of TGFβ1 which is from about 0.01% to about 99.99% of the total quantity of proteins in the mixture, as long as the ratio of TGFβ to at least one BMP protein in the mixture is greater than 10:1. In other embodiments, the quantity of TGFβ1 is from about 0.01% to about 75% of total proteins in the mixture, from about 0.01% to about 50% of total proteins in the mixture, from about 0.01% to about 25% of total proteins in the mixture, from about 0.01% to about 10% of total proteins in the mixture, or from about 0.1% to about 1% of total proteins in the mixture. In a preferred embodiment, the quantity of TGFβ1 is at least about 33% of total proteins in the mixture (up to a maximum of about 99.99%). In another preferred embodiment, the quantity of TGFβ1 is at least about 50% of total proteins in the mixture (up to a maximum of about 99.99%).

The quantity of the BMP-2 in the mixture is typically from about 0.1% to about 5% of total proteins in the mixture, or from about 0.01 to about 1%, or from about 0.01 to about 0.1%, or from about 0.1 to about 1%, although the percentage of BMP-2 can be less than 0.01% of the total proteins when high concentrations of TGFβ proteins are added (e.g., when the ratio of TGFβ protein to BMP is greater than 10,000:1). The quantity of BMP-3 in the mixture is typically from about 0.1% to about 5% of total proteins in the mixture, or from about 0.01 to about 1%, or from about 0.01 to about 0.1%, or from about 0.1 to about 1%, although the percentage of BMP-3 can be less than 0.01% of the total proteins when high concentrations of TGFβ proteins are added. The quantity of BMP-7 in the mixture is typically from about 0.1% to about 5% of total proteins in the mixture, or from about 0.01 to about 1%, or from about 0.01 to about 0.1%, or from about 0.1 to about 1%, although the percentage of BMP-7 can be less than 0.01% of the total proteins when high concentrations of TGFβ proteins are added.

In one aspect of this embodiment of the present invention, the mixture of proteins further includes one or more of the following TGFβ superfamily proteins: TGFβ2, TGFβ3, BMP-4, BMP-5, BMP-6, BMP-8, BMP-9, and cartilage-derived morphogenetic protein (CDMP), which can include one or more of CDMP-1, CDMP-2 or CDMP-3. The quantity of TGFβ2 in such a mixture is typically from about 0.5% to about 12% of the total mixture of proteins, although additional TGFβ2 can be added to enhance the chondrogenic activity of the mixture of proteins, if desired, up to as much as about 99.99% of the total mixture of proteins. The quantity of TGFβ3 in such a mixture is typically from about 0.01% to about 15% of the total mixture of proteins, although additional TGFβ3 can be added to enhance the chondrogenic activity of the mixture of proteins, if desired, up to as much as about 99.99% of the total mixture of proteins. The quantity of BMP-4 in the bone-derived osteogenic or chondrogenic formulation typically comprises from about 0.01% to about 1% of the total formulation, although additional BMP-4 can be added to enhance the chondrogenic activity of the mixture of proteins. In some embodiments, the percentage of BMP-4 can be less than 0.01% of the total proteins when high concentrations of TGFβ proteins are added (e.g., when the ratio of TGFβ to BMP is greater than 10,000:1). The quantity of BMP-5 in the bone-derived osteogenic or chondrogenic formulation is typically from about 0.01% to about 1% of the total formulation, although additional BMP-5 can be added to enhance the chondrogenic activity of the mixture of proteins. In some embodiments, the percentage of BMP-5 can be less than 0.01% of the total proteins when high concentrations of TGFβ proteins are added (e.g., when the ratio of TGFβ to BMP is greater than 10,000:1). The quantity of BMP-6 in the bone-derived osteogenic or chondrogenic formulation is typically from about 0.01% to about 1% of the total formulation, although additional BMP-6 can be added to enhance the chondrogenic activity of the mixture of proteins. In some embodiments, the percentage of BMP-6 can be less than 0.01% of the total proteins when high concentrations of TGFβ proteins are added (e.g., when the ratio of TGFβ to BMP is greater than 10,000:1). The quantity of CDMP in the bone-derived osteogenic or chondrogenic formulation is typically from about 0.01% to about 1% of the total formulation, although additional CDMP can be added to enhance the chondrogenic activity of the mixture of proteins. In some embodiments, the percentage of CDMP can be less than 0.01% of the total proteins when high concentrations of TGFβ proteins are added (e.g., when the ratio of TGFβ to BMP is greater than 10,000:1).

In one aspect of this embodiment, the mixture of proteins can additionally include at least one bone matrix protein. Bone matrix proteins are generally described above. Preferred bone matrix proteins for use in this mixture of proteins include, but are not limited to, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and fibronectin. More preferably, bone matrix proteins suitable for use in this mixture of proteins include, but are not limited to, osteocalcin, osteonectin, bone sialoprotein (BSP), lysyloxidase, and cathepsin L pre. The bone matrix proteins are typically present in the mixture in a quantity from about 20% to about 98% of the total mixture of proteins. In one embodiment, the bone matrix proteins are present in the mixture in a quantity from about 40% to about 98% of the total mixture of proteins.

In another aspect of this embodiment, the mixture of proteins can additionally include at least one growth factor protein. Growth factor proteins are generally described above. Preferred growth factor proteins for use in this mixture of proteins include, but are not limited to, fibroblast growth factor-I (FGF-I), FGF-II, FGF-9, leukocyte inhibitory factor (LIF), insulin, insulin growth factor I (IGF-I), IGF-II, platelet-derived growth factor AA (PDGF-AA), PDGF-BB, PDGF-AB, stromal derived factor-2 (SDF-2), pituitary thyroid hormone (PTH), growth hormone, hepatocyte growth factor (HGF), epithelial growth factor (EGF), transforming growth factor-α (TGFα) and hedgehog proteins. A particularly preferred growth factor for use in this mixture of the present invention is FGF-I. Typically, the growth factor protein are present in the mixture of proteins at a quantity from about 0.01% to about 50% of the total mixture of proteins. In other embodiments, the quantity of growth factor proteins in the mixture is from about 0.5% to about 25% of the total mixture of proteins; or from about 0.1% to about 10% of the total mixture of proteins. When the growth factor is FGF-I, the quantity of FGF-I in the mixture of proteins is typically from about 0.001% to about 10% of the total mixture of proteins.

In yet another aspect of this embodiment, the mixture of proteins can include one or more serum proteins. Serum proteins have been generally described above. Preferably, serum proteins useful in this mixture include, but are not limited to, albumin, transferrin, α2-Hs GlycoP, IgG, α1-antitrypsin, β2-microglobulin, Apo A1 lipoprotein (LP) and/or Factor XIIIb. More preferably, serum proteins useful in this mixture include, but are not limited to, albumin, transferrin, Apo A1 LP and/or Factor XIIIb.

In one embodiment of the present invention, a mixture of chondrogenesis-enhancing proteins suitable for use in a chondrogenesis-inducing composition portion of a cartilage repair product of the present invention includes the following proteins: TGFβ1, TGFβ2, TGFβ3, BMP-2, BMP-3, BMP-4, BMP-5, BMP-6, BMP-7, CDMP, FGF-I, osteocalcin, osteonectin, MGP, BSP, lysyloxidase, and cathepsin L pre, wherein the ratio of TGFβ1 to at least one, and preferably all, BMP proteins (including CDMP) is greater than 10:1. In another embodiment, a suitable mixture of chondrogenesis-enhancing proteins includes the following proteins: TGFβ1, TGFβ2, TGFβ3, BMP-2, BMP-3, BMP-4, BMP-5, BMP-6, BMP-7, CDMP, FGF-I, osteocalcin, osteonectin, BSP, lysyloxidase, cathepsin L pre, albumin, transferrin, Apo A1 LP and Factor XIIIb, wherein the ratio of TGFβ1 to at least one, and preferably all, BMP proteins (including CDMP) is greater than 10:1. In yet another embodiment, a suitable mixture of chondrogenesis-enhancing proteins includes the mixture of proteins referred to herein as Bone Protein (BP; described above), wherein the ratio of TGFβ1 in the mixture to at least one, and preferably all, BMP proteins in the mixture, including in BP, is greater than 10:1. An example of a mixture of proteins which contained TGFβ1 and at least one BMP protein (as present in BP) at a ratio of greater than from about 10:1 to 10,000:1 is illustrated in Example 14.

In one embodiment of the cartilage repair product of the present invention, each of the chondrogenesis-enhancing proteins in the cartilage-inducing composition is provided by the composition either: (1) directly as a protein that is associated with the matrix, or (2) as a recombinant nucleic acid molecule associated with the matrix, such recombinant nucleic acid molecule encoding the protein and being operatively linked to a transcription control sequence such that the protein can be expressed under suitable conditions. Therefore, a cartilage-inducing composition of the present invention can include proteins, recombinant nucleic acid molecules, or a combination of proteins and recombinant nucleic acid molecules, such composition providing the chondrogenesis-enhancing proteins described above.

According to the present invention, a chondrogenesis-enhancing protein can be obtained from its natural source, produced using recombinant DNA technology, or synthesized chemically. As used herein, a chondrogenesis-enhancing protein can be a full-length protein (i.e., in its full-length, naturally occurring form), any homologue of such a protein, any fusion protein containing such a protein, or any mimetope of such a protein. The amino acid sequences for chondrogenesis-enhancing proteins disclosed herein, including the TGFβ superfamily proteins described herein, as well as nucleic acid sequences encoding the same are known in the art and are publicly available, for example, from sequence databases such as GenBank. Such sequences can therefore be obtained and used to produce proteins and/or recombinant nucleic acid molecules of the present invention.

A homologue is defined as a protein in which amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). A homologue of a chondrogenesis-enhancing protein is a protein having an amino acid sequence that is sufficiently similar to a naturally occurring chondrogenesis-enhancing protein amino acid sequence that the homologue has substantially the same or enhanced biological activity compared to the corresponding naturally occurring protein.

As used herein, a mimetope (also referred to as a synthetic mimic) of a chondrogenesis-enhancing protein according to the present invention refers to any compound that is able to mimic the activity of such a chondrogenesis-enhancing protein, often because the mimetope has a structure that mimics the chondrogenesis-enhancing protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of naturally occurring chondrogenesis-enhancing protein. Mimetopes can also be obtained by generating random samples of molecules, such as oligonucleotides, peptides or other organic or inorganic molecules, and screening such samples by affinity chromatography techniques using the corresponding binding partner.

According to the present invention, a fusion protein is a protein that includes a chondrogenesis-enhancing protein-containing domain attached to one or more fusion segments. Suitable fusion segments for use with present invention include, but are not limited to, segments that can: enhance a protein's stability; enhance the biological activity of a chondrogenesis-enhancing protein; and/or assist purification of a chondrogenesis-enhancing protein (e.g., by affinity chromatography). A suitable fusion segment can be a domain of any size that has the desired function (e.g., imparts increased stability, imparts enhanced biological activity to a protein, and/or simplifies purification of a protein). Fusion segments can be joined to amino and/or carboxyl termini of the chondrogenesis-enhancing protein-containing domain of the protein and can be susceptible to cleavage in order to enable straight-forward recovery of a chondrogenesis-enhancing protein. Fusion proteins are preferably produced by culturing a recombinant cell transformed with a fusion nucleic acid molecule that encodes a protein including the fusion segment attached to either the carboxyl and/or amino terminal end of a chondrogenesis-enhancing protein-containing domain. Preferred fusion segments include a metal binding domain (e.g., a poly-histidine segment); an immunoglobulin binding domain (e.g., Protein a; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies).

In one embodiment, a mixture of chondrogenesis-enhancing proteins according to the present invention is capable, when cultured together with ATDC5 cells for seven days at a concentration of about 100 ng/ml or less, of inducing a statistically significant increase in $A_{595}$ in an Alcian Blue assay performed with the ATDC5 cells. In a preferred embodiment, a mixture of chondrogenesis-enhancing proteins is capable of inducing a significant increase in $A_{59}$ in an Alcian Blue assay performed with the ATDC5 cells when cultured under the above conditions at a concentration of about 50 ng/ml or less, and more preferably, about 25 ng/ml or less, and even more preferably, about 10 ng/ml or less. As used herein, a statistically significant increase is defined as an increase in $A_{595}$ as compared to a control, in which the probability of such an increase being due to chance is $p<0.05$, and more preferably, $p<0.001$, and even more preferably, $p<0.005$.

According to the present invention, an ATDC5 Alcian Blue assay is known in the art and is described, for example, in von Schroeder et al., 1994, Teratology 50:54–62. For the purposes of determining whether a mixture of chondrogenesis-enhancing proteins meets the requirements of being capable of inducing a significant increase in $A_{595}$ in an Alcian Blue assay performed with the ATDC5 cells when cultured with such cells at a given concentration (e.g., 100 ng/ml), the following protocol can be used.

Murine ATDC5 cells were deposited by T. Atsumi (Deposit No. RCB0565) and are publicly available from the Riken Cell Bank, 3-1-1 Koyadai, Tsukuba Science City, 305 Japan. The ATDC5 cells are maintained in 100×20 mm standard tissue culture plates in Dulbecco's modified Eagle's medium (DMEM):Ham's F-12 (1:1) media that contains 5% fetal bovine serum, penicillin (50 U/ml), and streptomycin (50 mg/ml). Cultures are incubated in a humidified incubator at 37° C. and 5% $CO_2$. Passages 3–8 can be used to assay the activity of the mixture of proteins to be evaluated. To perform the Alcian Blue assay, first, the micromass culture technique is performed as described in Atkinson et al., 1997, ibid., with minor alterations. Briefly, trypsinized cells are resuspended in the ATDC5 culture medium described above at a concentration of about 100,000 cells/25 μl. The 25 μl spot of cells is placed in the center of a 24 well polystyrene microtiter tissue culture dish. After 1.5 hours, 1 ml of the culture media described above is added to the dish. After overnight incubation at 37° C. and 5% $CO^2$, media containing various concentrations of the mixture of chondrogenesis-inducing proteins (e.g., 100 ng/ml, 50 ng/ml, 25 ng/ml, 10 ng/ml), 5% FBS, 50 μg/ml ascorbic acid, and 10 mM β-glycerophosphate are added (Day 0), and the incubation is continued. This latter media is then replaced every 3–4 days (for a total of 2 more additions of BP). After incubation with the mixture of proteins to be tested, on Day 7, the culture media is removed and the cultures are washed three times with 1 ml of PBS. The cultures are then fixed with 10% neutral buffered formalin for 15 hours and washed twice with 0.5 N HCl. Cultures are stained for one hour at room temperature with a 0.5% Alcian Blue solution (pH 1.4). The stain is then removed and the cultures are washed with PBS to remove unbound stain. The blue stain is then extracted with guanidium HCl (4M, pH 1.7) at 70° C. for 18 hours, followed by measurement of absorption at 595 nm.

It is noted that those of skill in the art will be able to make minor modifications to the above protocol and obtain a similar outcome. Such modifications include seeding the bottom of a well with ATDC5 cells (i.e, about 25,000–50,000, not in micromass culture), using a serum substitute in the media, altering the concentration of serum, and/or omitting ascorbic acid and/or β-glycerophosphate from the media. Minor modifications to the Alcian Blue assay itself can include altering the pH of the Alcian Blue solution within the range from about pH 1 to about pH 1.4 and altering the concentration of the Alcian Blue solution within the range from about 0.05% to about 0.5%.

As discussed above, one or more of the chondrogenesis-enhancing proteins in the cartilage-inducing composition can be provided by the composition as a recombinant nucleic acid molecule associated with the cartilage repair matrix, such recombinant nucleic acid molecule encoding a chondrogenesis-enhancing protein and being operatively linked to a transcription control sequence such that the protein can be expressed under suitable conditions. A recombinant nucleic acid molecule useful in the present invention can include an isolated natural gene encoding a chondrogenesis-enhancing protein or a homologue of such a gene, the latter of which is described in more detail below. A nucleic acid molecule useful in the present invention can include one or more regulatory regions, full-length or partial coding regions, or combinations thereof.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated nucleic acid molecule encoding a chondrogenesis-enhancing protein can be isolated from its natural source or produced using recombinant DNA technology (e.g., polymerase chain reaction (PCR) amplification, cloning) or chemical synthesis. Isolated nucleic acid molecules can include, for example, natural allelic variants and nucleic acid molecule homologues modified by nucleotide insertions, deletions, substitutions, and/or inversions in a manner such that the modifications do not substantially interfere with the nucleic acid molecule's ability to encode a chondrogenesis-enhancing protein of the present invention or to form stable hybrids under stringent conditions with natural gene isolates. An isolated nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a chondrogenesis-enhancing protein of the present invention can vary due to degeneracies.

A nucleic acid molecule homologue can be produced using a number of methods known to those skilled in the art (see, for example, Sambrook et al., ibid.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologues can be selected by hybridization with a naturally occurring gene or by screening for the function of a protein encoded by the naturally occurring nucleic acid molecule. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a chondrogenesis-enhancing protein.

Knowing the nucleic acid sequence encoding a naturally occurring chondrogenesis-enhancing protein according to the present invention allows one skilled in the art to, for example, (a) make copies of those nucleic acid molecules, and (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including screening appropriate expression libraries with antibodies; traditional cloning techniques using oligonucleotide probes to screen appropriate libraries or DNA; and PCR amplification of appropriate libraries or DNA using oligonucleotide primers. Techniques to clone and amplify genes are disclosed, for example, in Sambrook et al., ibid.

According to the present invention, a nucleic acid molecule encoding a chondrogenesis-enhancing protein is operatively linked to one or more transcription control sequences to form a recombinant molecule. The phrase "operatively linked" refers to linking a nucleic acid molecule to a transcription control sequence in a manner such that the molecule is able to be expressed when transfected (i.e., transformed, transduced or transfected) into a host cell.

Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells useful in the product and method of the present invention. A variety of such transcription control sequences are known to those skilled in the art. Preferred transcription control sequences include those which function in mammalian, bacterial, insect cells, and preferably in mammalian cells.

One or more recombinant nucleic acid molecules encoding a chondrogenesis-enhancing protein can be used to produce the protein. In one embodiment, the protein is produced by expressing a recombinant nucleic acid molecule under conditions effective to produce the protein. A preferred method to produce an encoded protein is by transforming a host cell with one or more recombinant molecules to form a recombinant cell. Suitable host cells to transform include any mammalian cell that can be transformed. Host cells can be either untransfected cells or cells that are already transformed with at least one nucleic acid molecule. Host cells useful in the present invention can be any cell capable of producing a chondrogenesis-enhancing protein. In a preferred embodiment, the host cell itself is useful in enhancing chondrogenesis. A particularly preferred host cell includes a fibrochondrocyte, a chondrocyte, and a mesenchymal precursor cell.

According to the method of the present invention, ahost cell can be transformed with a recombinant nucleic acid molecule encoding a chondrogenesis-enhancing protein in vitro or in vivo. Transformation of a recombinant nucleic acid molecule into a cell in vitro can be accomplished by any method by which a nucleic acid molecule can be inserted into the cell. Transformation techniques include, but are not limited to, transfection, electroporation, microinjection, lipofection, adsorption, andprotoplast fusion. The resulting recombinant cell can then be associated with the cartilage repair matrix of the present invention by any suitable method to provide the chondrogenesis-enhancing proteins.

Recombinant nucleic acid molecules can be delivered in vivo and associated with the cartilage repair matrix in a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, Science 247, 1465–1468); (b) administering a nucleic acid molecule packaged as a recombinant virus or a recombinant cell (i. e., the nucleic acid molecule is delivered by a viral or cellular vehicle), whereby the virus or cell is associated with the cartilage repair matrix; or (c) administering a recombinant nucleic acid molecule associated with the cartilage repair matrix via a delivery vehicle such as a liposome or nanosphere delivery system described herein.

As discussed above, arecombinant nucleic acid molecule encoding a chondrogenesis-enhancing protein can be associated with the cartilage repair matrix as a recombinant virus particle. A recombinant virus includes a recombinant molecule that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. When administered to an animal, a recombinant virus infects cells at the site of administration of the cartilage repair product and directs the production of a chondrogenesis-enhancing protein.

Suitable liposomes for use as a delivery vehicle for a recombinant nucleic acid in vivo include any liposome. Preferred liposomes of the present invention include those liposomes commonly used in, for example, gene delivery methods known to those of skill in the art. Methods for preparation of liposomes and complexing nucleic acids with liposomes are well known in the art.

As described in detail below, a cartilage-inducing composition is associated with a cartilage repair matrix, such that the cartilage repair matrix serves, in one capacity, as a delivery vehicle for the composition to be delivered to the site of a cartilage lesion. Suitable methods for associating a cartilage-inducing composition containing chondrogenesis-enhancing proteins and/or recombinant nucleic acid molecules encoding such proteins with a cartilage repair matrix include any method which allows the proteins and/or recombinant nucleic acid molecules to be delivered to a site of cartilage repair together with a cartilage repair matrix such that the cartilage repair product is effective to repair and/or regenerate cartilage at the site. Such methods of association include, but are not limited to, suspension of the composition within the cartilage repair matrix, freeze-drying of the composition onto a surface of the matrix and suspension within the matrix of a carrier/delivery formulation containing the composition. Additionally, the cartilage-inducing composition can be associated with the matrix prior to placement of the product into a cartilage lesion (i.e., the association of the composition with matrix occurs ex vivo) or alternatively, a cartilage repair matrix can first be implanted into a lesion, followed by association of the cartilage-inducing composition with the matrix, such as by injection into or on top of the matrix (i.e., the association of the composition with matrix occurs in vivo). A cartilage-inducing composition can contain additional delivery formulations or carriers which enhance the association of the composition with the matrix, which enhance the delivery of the composition to the appropriate cells and tissue at the site of the lesion, and which assist in controlling the release of the factors in the composition at the site of the lesion. Suitable delivery formulations include carriers, which, as used herein, include compounds that increase the half-life of a cartilage-inducing composition in the treated animal. Suitable carriers include, but are not limited to, polymeric controlled release vehicles, biodegradable implants, liposomes, bacteria, viruses, oils, cells, esters, and glycols.

One embodiment of the present invention is a controlled release formulation that is capable of slowly releasing a composition of the present invention into an animal. As used herein, a controlled release formulation comprises a cartilage-inducing composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon association with the matrix or upon administration to an animal, form a solid or a gel in situ. Such controlled release vehicles are preferably associated with the cartilage repair matrix by one of the above-described methods. Preferred controlled release formulations are biodegradable (i.e., bioerodible).

A preferred controlled release formulation of the present invention is capable of releasing a composition of the present invention at the site of a cartilage lesion of a treated animal at a constant rate sufficient to attain therapeutic dose levels of the chondrogenesis-enhancing proteins provided by the composition to result in enhancement of chondrogenesis at the lesion. A particularly preferred controlled release vehicle according to the present invention is a nanosphere delivery vehicle.

A nanosphere delivery vehicle according to the present invention includes the nanosphere delivery vehicle described in copending PCT ApplicationNo. PCT/EP 98/05100, which is incorporated herein by reference in its entirety. In a preferred embodiment, such a delivery vehicle includes polymer particles having a size of less than 1000 nm and being loaded with between 0.001% and 17% by weight of the cartilage-inducing composition. The nanospheres have an in vitro analytically determined release rate profile with an initial burst of about 10% to about 20% of the total amount of the composition over a first 24 hour period, and a long time release rate of a least 0.1% per day during at least seven following days.

A cartilage-inducing composition useful in the cartilage repair product of the present invention can also include one or more pharmaceutically acceptable excipients. As used herein, a pharmaceutically acceptable excipient refers to any substance suitable for associating a cartilage-inducing composition with a cartilage repair matrix and maintaining and delivering the components of the composition (e.g., proteins and/or recombinant nucleic acid molecules) to the appropriate cells at a suitable in vivo site (i.e., a cartilage lesion). Preferred pharmaceutically acceptable excipients are capable of maintaining a nucleic acid molecule in a form that, upon arrival of the nucleic acid molecule at the delivery site, the nucleic acid molecule is capable of expressing a chondrogenesis-enhancing protein either by being expressed by a recombinant cell or by entering a host cell at the site of the lesion and being expressed by the cell. A suitable pharmaceutically acceptable excipient is capable of maintaining a protein in a form that, upon arrival of the protein at the delivery site, the protein is biologically active such that chondrogenesis at the site is enhanced. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Particularly preferred excipients include non-ionic diluents, with a preferred non-ionic buffer being 5% dextrose in water (DW5). Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzol alcohol. Cartilage-inducing compositions of the present invention can be sterilized by conventional methods and/or lyophilized.

A cartilage-inducing composition is present in the cartilage repair product of the present invention at a concentration that is effective to induce, at the site of a cartilage lesion, one or more of: cellular infiltration, cellular proliferation, angiogenesis, and cellular differentiation to type II collagen-producing chondrocytes. Preferably, a cartilage-inducing composition is present in the cartilage repair product of the present invention at a concentration that is effective to induce cartilage repair and/or regeneration at the site of a cartilage lesion. When the chondrogenesis-enhancing proteins are provided by the cartilage-inducing protein directly as a protein, the cartilage-inducing composition is typically provided at a concentration of from about 0.5% to about 33% by weight of the cartilage repair product. More preferably, the cartilage-inducing composition is provided at a concentration of from about 1% to about 20% by weight of the cartilage repair product. When one or more of the chondrogenesis-enhancing proteins are provided by the composition as a recombinant nucleic acid molecule, an appropriate concentration of a nucleic acid molecule expressing one chondrogenesis-enhancing protein is an amount which results in at least about 1 pg of protein expressed per mg of total tissue protein at the site of delivery per μg of nucleic acid delivered, and more preferably, an amount which results in at least about 10 pg of protein expressed per mg of total tissue protein per μg of nucleic acid delivered; and even more preferably, at least about 50 pg of protein expressed per mg of total tissue protein per μg of nucleic acid delivered; and most preferably, at least about 100 pg of protein expressed per mg of total tissue protein per μg of nucleic acid delivered. One of skill in the art will be able to adjust the concentration of proteins and/or nucleic acid molecules in the composition depending on the types and number of proteins to be provided by the composition, and the delivery vehicle used.

In another embodiment of the cartilage repair product of the present invention, a cartilage-inducing composition can also contain a factor that non-covalently attaches to one or more of any of the chondrogenesis-enhancing proteins or recombinant nucleic acid molecules in the composition and thus, modify the release rate of the factor. Such factors include, but are not limited to, any ground substance or other polymeric substance. As used herein, a ground substance is defined as the non-living matrix of connective tissue, which includes natural polymers and proteoglycans. Natural polymers include, but are not limited to collagen, elastin, reticulin and analogs thereof. Proteoglycans include, but are not limited to any glycosaminoglycan-containing molecules, and include chondroitin sulfate, dermatan sulphate, heparan sulphate, keratan sulphate and hyaluronan. Preferred ground substances include, but are not limited to, type I collagen, type II collagen, type III collagen, type IV collagen and hyaluronic acid. Preferred other polymeric substances include, but are not limited to, poly(lactic acid) and poly (glycolic acid).

In a further embodiment, the cartilage-inducing composition can include one or more types of cells which are provided to further enhance chondrogenesis at the site of the cartilage lesion. Such cells include, but are not limited to, fibrochondrocytes, chondrocytes, mesenchymal precursors, and any other cell that can serve as a chondrocyte precursor. Such cells can be associated with the composition and the matrix by any of the methods described above. In one embodiment, at least some of the cells are transformed with a recombinant nucleic acid molecule encoding a chondrogenesis-enhancing protein to form a recombinant cell.

The cartilage repair product of the present invention also includes a cartilage repair matrix. The cartilage repair matrix is the component of the cartilage repair device which provides a vehicle for delivery of the cartilage-inducing composition to the site of a cartilage lesion and a suitable scaffold upon which cartilage repair and regeneration can occur. In a preferred embodiment, the cartilage repair matrix is bioresorbable.

According to the present invention, a cartilage repair matrix can be formed of any material that is suitable for in vivo use, and which provides the above-described characteristics of a cartilage repair matrix for use with a cartilage-inducing composition of the present invention. The matrix can be formed of materials which include, but are not limited to, synthetic polymers and/or a ground substance. Preferred ground substances include natural polymers and proteoglycans. Natural polymers include, but are not limited to collagen, elastin, reticulin and analogs thereof Proteoglycans include, but are not limited to, any glycosaminoglycan-containing molecules. Particularly preferred glycosaminoglycans include chondroitin sulfate, dermatan sulphate, heparan sulphate, keratan sulphate and hyaluronan. Other preferred ground substances include, but are not limited to, type I collagen, type II collagen, type III collagen, type IV collagen and hyaluronic acid. Preferred synthetic polymers include poly(lactic acid) and poly(glycolic acid).

In one embodiment of the present invention, the cartilage repair matrix includes collagen. Preferably, the matrix contains from about 20% to about 100% collagen by dry weight of the matrix, and more preferably, from about 50% to about 100% collagen by dry weight of the matrix, and even more preferably, from about 75% to about 100% collagen by dry weight of the matrix. In one embodiment, a suitable cartilage repair matrix includes collagen from bovine tendon.

A cartilage repair matrix suitable for use in the present invention can include a material as described above which is in any suitable form for use in repairing a cartilage lesion, including a sponge, a membrane, a film or a gel. In one embodiment, a suitable cartilage repair matrix includes autograft tissue, allograft tissue and/or xenograft tissue.

Figure 1B:
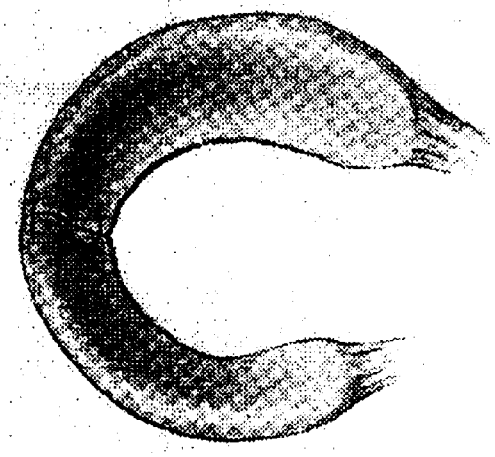
FIG. 1B shows a conventional suture repair and resection of the meniscal radial tear illustrated in FIG. 1A.
Figure 1C:
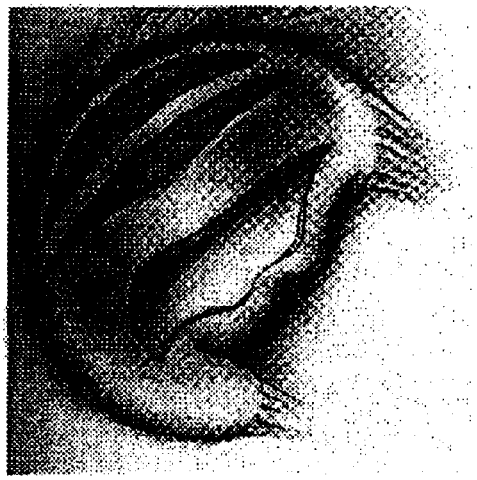
FIG. 1C shows a meniscal triple bucket handle tear.
Figure 1D:
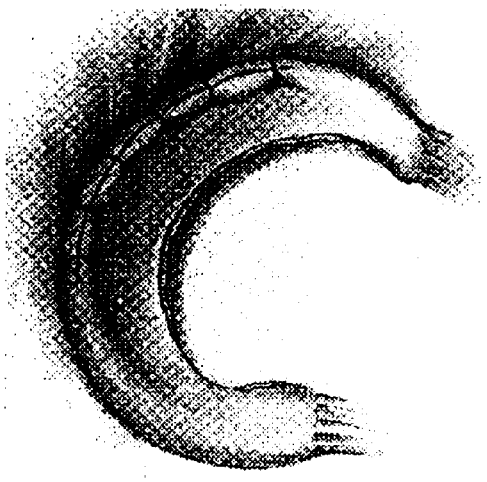
FIG. 1D shows a conventional suture repair and resection of the meniscal triple bucket handle tear illustrated in FIG. 1C.
Figures 2A, 2B:
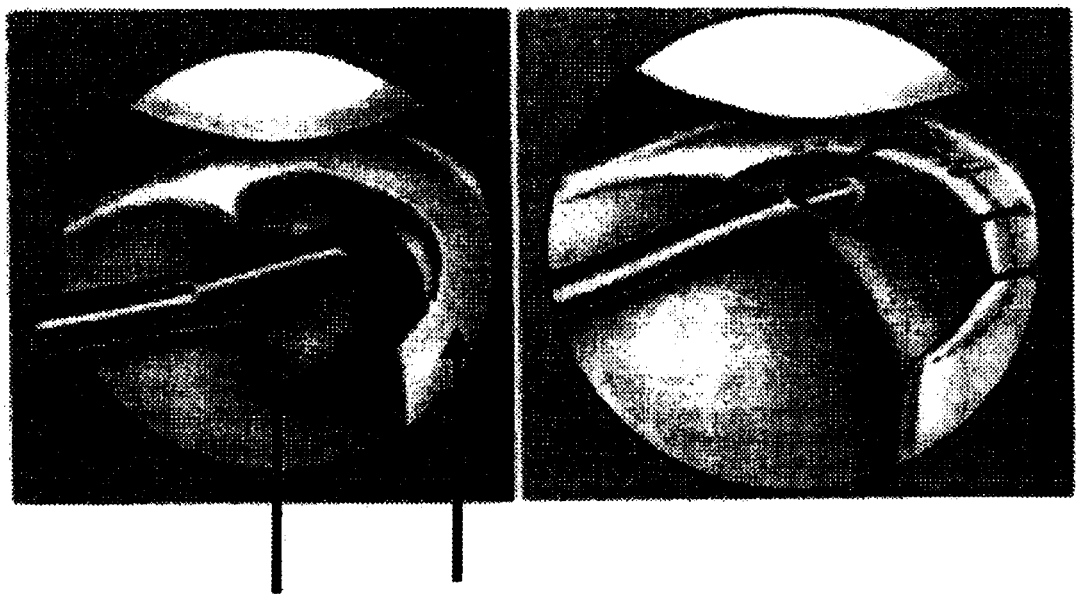
FIG. 2A illustrates implantation of a cartilage repair product of the present invention to a meniscal segmental lesion.
FIG. 2B illustrates fixation of a cartilage repair product of the present invention to a meniscal segmental lesion.
Figure 3B:
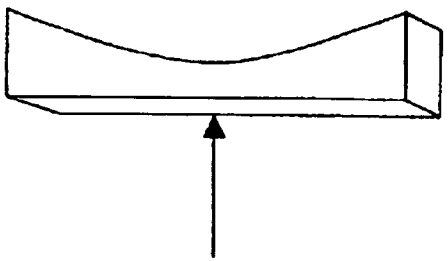
FIG. 3B illustrates one approximate shape of a cartilage repair product of the present invention.
Figure 3A:
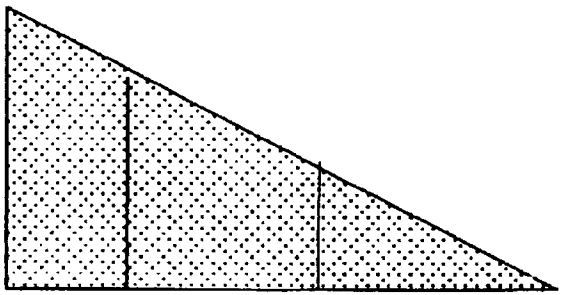
FIG. 3A is a diagram illustrating a meniscus cross section having vascular, semivascular and avascular zones.
Figure 4A:
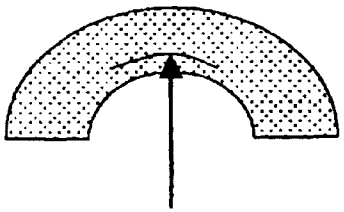
FIG. 4A is an illustration of a meniscus having a longitudinal tear in the avascular region as viewed from the femur towards the tibia.

A cartilage repair product of the present invention is useful for repairing a variety of defects in cartilage, including both tears and segmental defects in both vascular and avascular cartilage tissue. The product is particularly useful for repairing defects in hyaline (e.g., articular) and/or fibrocartilage (e.g., meniscal). Examples of various types of cartilage tears and segmental defects for which the cartilage repair product of the present invention can be used are illustrated in FIGS. 1–4. Briefly, FIG. 1 shows a meniscal radial tear (FIG. 1A); a meniscal triple bucket handle tear (FIG. 1C); and a longitudinal tear in the avascular area of a meniscus (FIG. 4A). A meniscal segmental lesion is illustrated in FIGS. 2A and 2B. FIG. 3A additionally schematically illustrates a cross section of the meniscus, which includes vascular, semi-vascular and avascular regions for which, prior to the present invention, only tears in the vascular region were repairable.

Therefore, since cartilage defects (i.e., lesions) can occur in a variety of shapes, sizes, and locations, a cartilage repair matrix suitable for use in a cartilage repair product of the present invention is of a shape and size sufficient to conform to a specific defect in the cartilage of the patient to be treated. Preferably, the cartilage repair matrix, when used in the repair of a cartilage defect, achieves a geometry at the defect site that is suitable to provide a therapeutic benefit to the patient. Such a therapeutic benefit can be any improvement in a patient's health and well being that is related to a correction of the cartilage defect, and preferably, the therapeutic benefit includes the repair of the defect such that the natural configuration of the cartilage is at least partially restored.

Figure 4B:
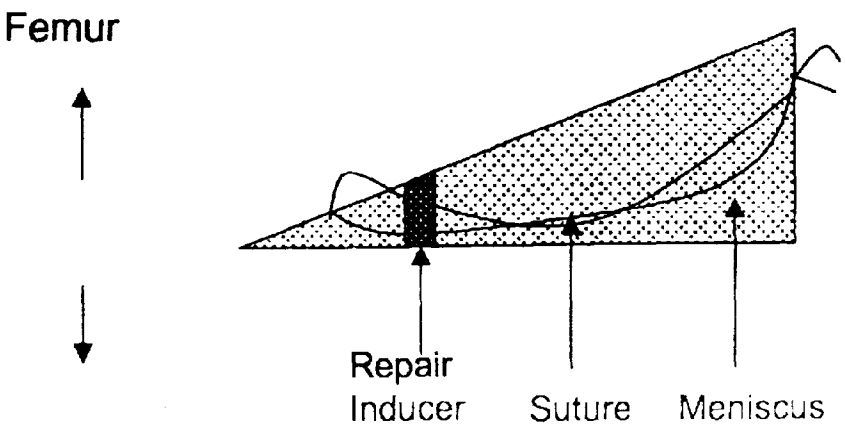
FIG. 4B is a diagram illustrating a cross section of the meniscus depicted in FIG. 4A containing a cartilage repair product of the present invention.

In the case of a cartilage tear, the cartilage repair matrix is typically configured as a sheet. The sheet is preferably of a shape and size suitable for insertion into the tear and to cover the entire tear surface. One embodiment of a sheet type matrix is schematically illustrated in FIG. 3B. The use of such a matrix to repair an avascular longitudinal tear is schematically illustrated in FIG. 4B. Preferably, the matrix provides an immediate mechanical repair of the tear, a surface for interacting the cartilage-inducing composition with the natural cartilage tissue, and a scaffold upon which chondrogenesis can occur. Additionally, the matrix preferably imparts upon the product a mechanical stability sufficient to allow the product to be anchored into the lesion. Prior to the present invention, a tear in meniscal vascular cartilage as shown in FIGS. 1A and 1C was repaired by suture repair and resection as illustrated in FIGS. 1B and 1D, respectively. Additionally, prior to the present invention, if the tear occurred in avascular cartilage tissue (or in semi-vascular tissue as shown in FIG. 3A), the tear would have been considered "irreparable". The cartilage repair product of the present invention advantageously allows for the repair of tears in both avascular and vascular cartilage and when used in vascular cartilage, the product enhances the rate and quality of the repair as compared to previously used products and methods, such as shown in FIGS. 1B and 1D.

In the embodiment in which the cartilage repair matrix is configured as a sheet, the matrix preferably has a thickness of from about 0.1 mm to about 3 mm, and more preferably, from about 0.5 mm to about 2 mm. The thickness can, of course, be varied depending on the configuration of the tear which is to be repaired. In this embodiment, the matrix can be prepared by applying an aqueous dispersion of matrix material into a mold, for example, wherein the mold sets the appropriate thickness for the sheet. Such a method is described in Example 4. In a preferred embodiment, the matrix is prepared from an aqueous dispersion of from about 0.2% to about 4% collagen by weight, and more preferably, the matrix is prepared from an aqueous dispersion of from about 0.5% to about 3% collagen by weight.

In the case of a segmental defect in cartilage (i.e., any defect that is larger and of a different shape than a tear), the cartilage repair matrix is typically configured to achieve a suitable geometry that repairs the defect, and includes matrices which are configured to replace damaged cartilage which has been removed. Prior to the present invention, repair of a segmental defect or indeed, any defect which occurred in the avascular region of meniscal tissue, typically involved the removal of the damaged tissue, such as by partial or complete excision of the meniscus (i.e., a meniscectomy). Excision was then sometimes followed by a replacement prosthetic meniscus, but until the present invention, such methods were unable to regenerate endogenous-type cartilage in the avascular region of the meniscus. The cartilage repair matrix useful for segmental cartilage defects (i.e., "non-tear" defects) is preferably of a shape and size suitable for providing an immediate mechanical repair of the defect, a surface for interacting the cartilage-inducing composition with the natural cartilage tissue, and a scaffold upon which chondrogenesis can occur. Additionally, the matrix preferably imparts upon the product a mechanical stability sufficient to allow the product to be anchored into the lesion. A cartilage repair matrix suitable for use for repairing segmental defects in the cartilage repair product of the present invention is described in detail in U.S. Pat. No. 5,681,353 to Li et al. which is incorporated herein by reference in its entirety. Other preferred cartilage repair matrices are described in the Examples section. In one embodiment, a cartilage repair matrix used to repair a segmental defect in meniscal cartilage contains a porous ground substance composite which includes collagen and has the shape and mechanical characteristics suitable to repair a meniscus lesion.

In one embodiment, a cartilage repair matrix suitable for use in the repair of segmental defects has a tapered shape. Such a matrix typically varies in thickness from about 0.5 mm to about 3 mm at its thinnest region to from about 4 mm to about 10 mm at its thickest region. Such a matrix typically has a density of from about 0.07 to about 0.5 grams matrix per $cm^3$, and more preferably, from about 0.1 to about 0.25 grams matrix per $cm^3$, wherein $g/cm^3$ represents the number of grams in a cubic centimeter of matrix. FIGS. 2A and 2B illustrate a cartilage repair matrix configured to repair a segmental defect in a memscus.

In a preferred embodiment, the cartilage repair matrix of the present invention is porous, which enhances the ability of the matrix to serve as a delivery vehicle for the cartilage-inducing composition and particularly, as a scaffold for chondrogenesis, such as by allowing for the ingrowth of cells into the matrix. Preferably, the pore size is sufficient to maintain the desired mechanical strength of the matrix, while allowing sufficient ingrowth of cells for regeneration of cartilage at the lesion. The porosity of the matrix can vary depending on the configuration of the matrix, but typically, the matrix has a pore size of from about 10 μm to about 500 μm. When the matrix is configured to repair a tear defect, the pore size is typically from about 10 μm to about 100 μm. When the matrix is configured to repair a segmental defect, the pore size is typically from about 50 μm to about 500 μm.

When the cartilage repair matrix is configured as a sheet, it is preferably not cross-linked. When the cartilage repair matrix is configured to repair a segmental defect, however, the matrix can be cross-linked, such as by artificial cross-linking methods, although such cross-linking is not required a cartilage repair matrix can be cross-linked by any suitable agent which includes, but is not limited to, formaldehyde, glutaraldehyde, dimethyl suberimidate, carbodiimides, multi-functional epoxides, succinimidyls, Genipin, poly (glycidyl ether), diisocyanates, acyl azide, ultraviolet irradiation, dehydrothermal treatment, tris(hydroxymethyl) phosphine, ascorbate-copper, glucose-lysine and photo-oxidizers. In one embodiment, a cartilage repair matrix is cross-linked with an aldehyde.

Another embodiment of the present invention relates to a product for the repair of cartilage lesions which includes: (a) a cartilage repair matrix as described in detail above; and, (b) a cartilage inducing composition associated with the matrix which includes cells that have been cultured with a mixture of the chondrogenesis-enhancing proteins as previously described herein. The cartilage-inducing composition can be any of the above-described cartilage-inducing compositions useful in a product of the present invention. Preferably, the cells to be cultured with the mixture of proteins are cells which are involved in chondrogenesis, and include, but are not limited to, fibrochondrocytes, chondrocytes, mesenchymal precursors, and any other cell that can serve as a chondrocyte precursor. Such cells are preferably cultured in vitro prior to their association with a cartilage repair matrix, under conditions effective to allow the cells to interact with the proteins and initiate chondrogenesis by the cells. Effective culture conditions include, but are not limited to, effective media, bioreactor, temperature, pH and oxygen conditions that permit interaction of the proteins and cells and initiation of chondrogenesis processes by the cells. An effective, medium refers to any medium in which a cell is cultured provide such a result. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a the cell. Such culturing conditions are within the expertise of one of ordinary skill in the art. In another aspect of this embodiment of the present invention, a cartilage repair matrix is cultured in vitro together with the cells and mixture of proteins prior to implantation into a cartilage lesion in vivo. In a further embodiment, the cells that have been cultured with the mixture of proteins can be associated with the cartilage repair matrix in conjunction with additional chondrogenesis-enhancing proteins and/or recombinant nucleic acid molecules encoding such proteins as described above.

Another embodiment of the present invention relates to a product for the repair of vascular and avascular meniscus tears. Such a product includes: (a) a cartilage repair matrix comprising collagen and configured as a sheet; and, (b) a cartilage-inducing composition associated with the matrix. The cartilage-inducing composition can be any of the above-described cartilage-inducing compositions useful in a product of the present invention. Each of the chondrogenesis-enhancing proteins is provided as a protein or by a recombinant nucleic acid molecule encoding the protein operatively linked to a transcription control sequence. In one embodiment, the cartilage repair matrix is formed of a collagen sponge. When the lesion to be repaired is in the avascular region, the product can additionally include a time controlled delivery formulation as described in detail above.

Yet another embodiment of the present invention relates to a method for repair of cartilage lesions. The method includes the steps of implanting and fixing into a cartilage lesion a product which includes: (a) a cartilage repair matrix; and (b) a cartilage-inducing composition associated with the matrix. The cartilage-inducing composition can be any of the above-described embodiments of a cartilage-inducing composition suitable for use with a product of the present invention. In one embodiment, a cartilage-inducing composition useful in the method of the present invention includes a mixture of proteins including: transforming growth factor β1 (TGFβ1), bone morphogenetic protein (BMP)-2, BMP-3, and BMP-7, wherein the quantity of the TGFβ1 in the mixture is from about 0.01% to about 99.99% of total proteins in the mixture; wherein the quantity of the BMP-2 in the mixture is from about 0.01% to about 10% of total proteins in the mixture; wherein the quantity of the BMP-3 in the mixture is from about 0.1% to about 15% of total proteins in the mixture; and, wherein the quantity of the BMP-7 in the mixture is from about 0.01% to about 10% of total proteins in the mixture. Various alternate and additional aspects of this embodiment of a cartilage-inducing composition have been described in detail above. In particular, in one aspect of this embodiment, the ratio of TGFβ1 to all other proteins in the mixture of proteins is at least about 1:10, and more preferably, at least about 1:3, and more preferably, at least about 1:1, and even more preferably, at least about 10:1, weight for weight (w/w).

In another embodiment, the cartilage-inducing composition suitable for use in the method of the present invention includes a mixture of proteins including: (a) a bone-derived osteogenic or chondrogenic formulation of proteins; and, (b) an exogenous TGFβ protein, wherein the exogenous TGFβ protein is present in an amount sufficient to increase cartilage induction by the composition over a level of cartilage induction by the bone-derived osteogenic or chondrogenic protein formulation in the absence of the exogenous TGFβ protein. Various alternate and additional aspects of this embodiment of a cartilage-inducing composition have been described in detail above. In particular, in one aspect of this embodiment, the TGFβ protein is TGFβ1, and the ratio of TGFβ1 to all other proteins in the mixture of proteins is at least about 1:10, and more preferably, at least about 1:3, and more preferably, at least about 1:1, and even more preferably, at least about 10:1, weight for weight (w/w).

In another embodiment, the cartilage-inducing composition suitable for use in the method of the present invention includes a mixture of proteins including: (a) a TGFβ protein; and, (b) at least one bone morphogenetic protein (BMP), wherein the ratio of the TGFβ protein to the BMP protein is greater than about 10:1. Various alternate and additional aspects of this embodiment of a cartilage-inducing composition have been described in detail above. In particular, in one aspect of this embodiment, the TGFβ protein is TGFβ1, and the ratio of TGFβ1 to the BMP protein is greater than about 100:1, and more preferably, greater than about 1000:1, and even more preferably, greater than about 10,000:1, weight for weight (w/w).

The method of the present invention is useful for repairing any of the cartilage lesions described above, including both articular and meniscal cartilage lesions, and both avascular and vascular defects. The step of implanting is performed using surgical techniques known in the art, and typically involves inserting the repair product directly into the tear when the matrix is configured as a sheet, and involves a more complex process of removing damaged tissue and implanting the repair product when the matrix is configured to repair a segmental defect. The step of fixing can include attaching the product to the cartilage at the site of the lesion by any means suitable for attaching a matrix as described herein to cartilage or tissue surrounding the cartilage in vivo. Such a means for attaching can include, but is not limited to application of bioresorbable sutures, application of non-resorbable sutures, press-fitting, application of arrows, application of nails, or application of a T-fix suture anchor device. Examples 5 and 7–9 describe the method of the present invention when the cartilage repair matrix is configured as a sheet and used to repair meniscal and articular cartilage. Example 6 describes the method of the present invention which is used to repair meniscal and articular cartilage when the repair matrix is configured to repair a segmental defect. FIGS. 2A and 2B illustrate the implantation and fixation of a cartilage repair product into a segmental defect in meniscal cartilage. FIGS. 4A and 4B schematically illustrate the repair of a longitudinal tear in avascular meniscal tissue using a cartilage repair product configured as a sheet.

Figure 8:
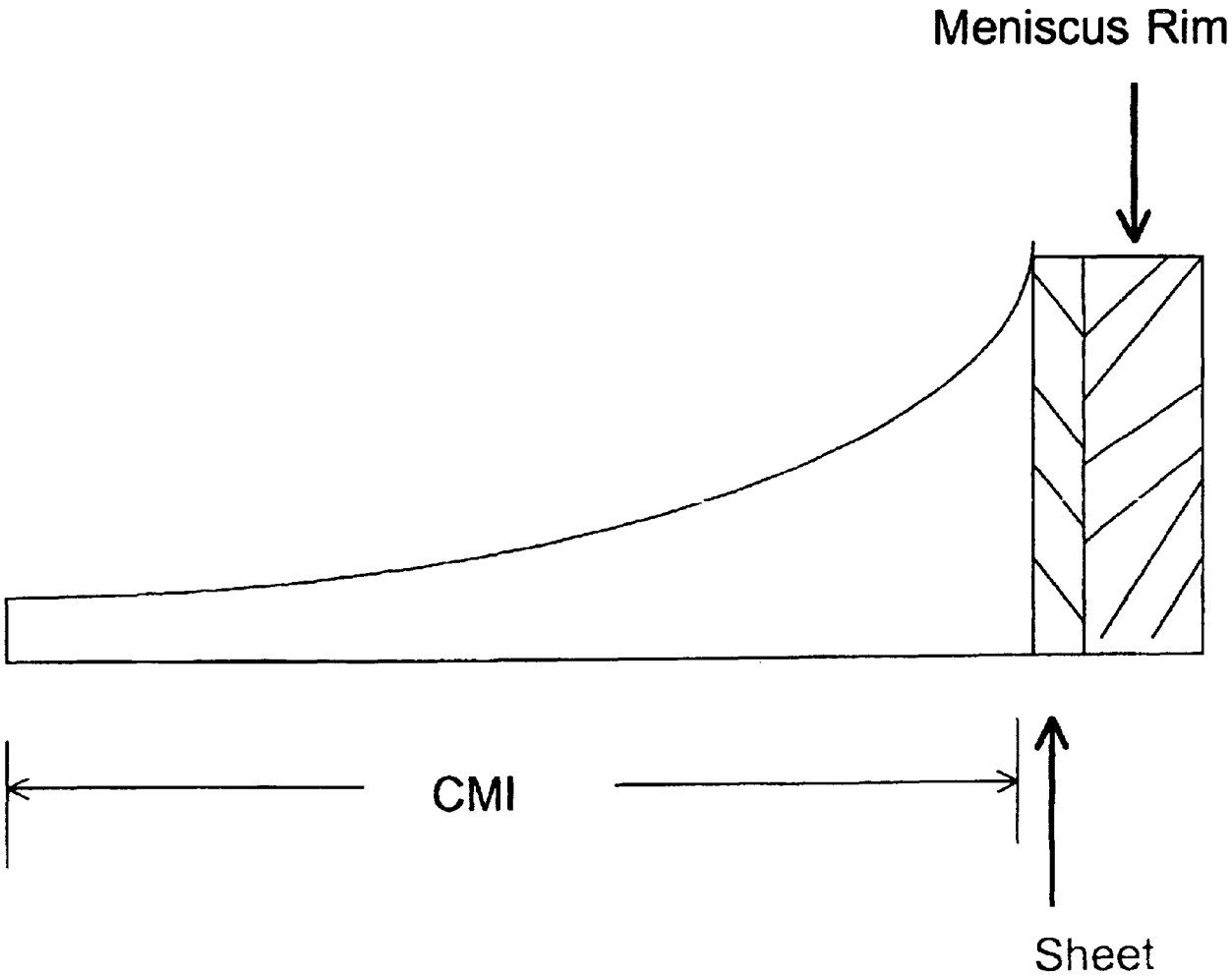
FIG. 8 is a diagram illustrating a cross-section view of a combination collagen meniscus implant (CMI) and sheet cartilage repair product of the present invention used to repair a meniscal defect.

In one embodiment of the method of the present invention, a cartilage lesion which is a segmental defect is repaired by using two cartilage repair products of the present invention. In this embodiment, a segmental defect, and preferably a meniscal segmental defect, is repaired by trimming damaged cartilage tissue away to form a suitable interface for implantation of the repair devices. A first cartilage repair product having a matrix configured as a sheet is implanted and fixed along the defect (e.g., along the meniscal rim when the defect is in vascular cartilage and this cartilage has been removed). A second cartilage repair matrix configured to replace the segmental defect, or a cartilage repair product having a matrix configured to replace the segmental defect, is implanted and fixed to the first product configured as a sheet. The sheet provides an interface in which cells can quickly infiltrate and react with the cartilage repair composition. In this embodiment, the cartilage repair product configured as a sheet contains a cartilage repair composition as described herein, and the cartilage repair product configured to repair the segmental defect may or may not be associated with the cartilage repair composition, as deemed necessary by the surgeon. FIG. 8 schematically illustrates the concurrent use of both a cartilage repair product configured as a sheet and a cartilage repair product configured to repair a segmental defect.

Another embodiment of the method of the present invention relates to a method for repair of avascular meniscus lesions. The method includes the steps of implanting and fixing into a cartilage lesion of the avascular region of a meniscus a cartilage repair product as described herein, wherein the cartilage repair matrix is configured as a sheet, and wherein the cartilage repair product further includes a time controlled delivery formulation which is associated with the matrix in conjunction with the cartilage-inducing composition.

Another embodiment of the method of the present invention is a method for enhanced repair of vascular meniscus lesions. The method includes the steps of implanting and fixing into a cartilage lesion in the vascular region of a meniscus a cartilage repair product as described herein, wherein the cartilage repair matrix includes collagen and is configured as a sheet. The present inventors have discovered that the use of the cartilage repair product of the present invention to repair vascular lesions measurably enhances the rate of repair of the vascular lesion as compared to the rate of repair of a meniscus lesion repaired in the absence of the product. According to the present invention, a measurable enhancement of the rate of repair is any measurable improvement in the time between Day 0 of the repair (i.e., the day the product is implanted into the patient) and the day on which it is determined that suitable cartilage tissue growth has occurred at the lesion as compared to a vascular lesion that is repaired in the absence of the product of the present invention. Suitable cartilage tissue growth is defined as an initial indication of enhanced blood vessel formation, production of fibrochondrocytes, induction of cellular infiltration into the product, induction of cellular proliferation, and production of cellular and spatial organization to form a three-dimensional tissue that more nearly represents endogenous cartilage tissue from the site of the lesion. In a preferred embodiment, the product of the present invention measurably enhances the rate of repair of a vascular cartilage lesion, as compared to a vascular lesion that is repaired in the absence of the product of the present invention, by at least 25%, and more preferably, by at least about 50%, and more preferably by at least about 100%.

In addition, the use of the cartilage repair product of the present invention to repair vascular cartilage lesions results in a measurable enhancement of the quality of repair of the vascular lesion as compared to the quality of repair of a lesion repaired in the absence of the product. A measurable enhancement in the quality of repair of the vascular lesion is defined as any measurable improvement in quality of cartilage formation at the site of the lesion, with an improvement being defined as development of a more normal cartilage tissue, which can be indicated by enhanced blood vessel formation, production of fibrochondrocytes, induction of cellular infiltration into the product, induction of cellular proliferation, and production of cellular and spatial organization to form a three-dimensional tissue that more nearly represents endogenous cartilage tissue from the site of the lesion.

More particularly, the quality of repair of cartilage tissue according to the present invention can be evaluated as follows.

The quality of meniscal cartilage repair (i.e., fibrocartilage cartilage) can be evaluated by histological analysis of the tissue at the repair site on a scale of 0 to 4 based on the following parameters: I. Histological cartilage staining in the defect, II. Cellular infiltration into the collagen implant, and III. Integration into the endogenous meniscus. These scales according to the present invention are defined as follows:

I.

| Score | % of cells within implant that stain with Azure at pH - 2 |
|---|---|
| 4 | 75-100 |
| 3 | 50-75 |
| 2 | 25-50 |
| 1 | 10-25 |
| 0 | 0-10 |

II.

| Score | % of cells that have infiltrated the collagen implant |
|---|---|
| 4 | 75-100 |
| 3 | 50-75 |
| 2 | 25-50 |
| 1 | 10-25 |
| 0 | 0-10 |

III.

| Score | % of the repaired site that integrates with the endogenous meniscus |
|---|---|
| 4 | 75-100 |
| 3 | 50-75 |
| 2 | 25-50 |
| 1 | 10-25 |
| 0 | 0-10 |

Preferably, a measurable enhancement in the quality of repair of a meniscal lesion is defined as a higher score in at least one of the parameters defined above as I, II and III, with a "4" being the highest score in each parameter, than a lesion repaired in the absence of the product of the present invention. More preferably, a measurable enhancement in the quality of repair of a meniscal lesion is defined as a score of at least 1, and more preferably at least 2 and more preferably at least 3, and most preferably at least 4 in at least one of the parameters defined above as I, II and/or III, as compared to a lesion repaired in the absence of the product of the present invention.

The quality of osteochondral repair (articular cartilage defects) can be evaluated by histological analysis of the tissue at the repair site on a scale of 0 to 4 based on the following parameters:: I. defect filling with bone, II. thickness of the repaired cartilage, and III. repaired cartilage integration with the endogenous cartilage. These scales according to the present invention are defined as follows:

I.

| Score | % of defect that is filled with bone |
|---|---|
| 4 | 75-100 |
| 3 | 50-75 |
| 2 | 25-50 |
| 1 | 10-25 |
| 0 | 0-10 |

II.

| Score | % of repaired cartilage that is thickness of endogenous cartilage |
|---|---|
| 4 | 75-100 |
| 3 | 50-75 |
| 2 | 25-50 |
| 1 | 10-25 |
| 0 | 0-10 |

| III. | |
|---|---|
| Score | % of repaired cartilage that integrates with the endogenous cartilage |
| 4 | 75-100 |
| 3 | 50-75 |
| 2 | 25-50 |
| 1 | 10-25 |
| 0 | 0-10 |

Preferably, a measurable enhancement in the quality of repair of an osteochondral lesion is defined as a higher score in at least one of the parameters defined above as I, II and III, with "4" being the highest score, than a lesion repaired in the absence of the product of the present invention. More preferably, a measurable enhancement in the quality of repair of an osteochondral lesion is defined as a score of at least 1, and more preferably at least 2 and more preferably at least 3, and most preferably at least 4 in at least one of the parameters defined above as I, II or III, as compared to a lesion repaired in the absence of the product of the present invention.

The grading scale utilized for bone-inductive activity in the rodent subcutaneous assay, which was developed by Sulzer Biologics, Inc., is shown in Example 10, Table 8. The grading scale utilized for cartilage-inductive activity in the rodent subcutaneous assay, which was also developed by Sulzer Biologics, Inc., is shown in Example 10, Table 9. Such grading scales can also be used to optimize compositions for use in the present invention and to evaluate the predicted in vivo efficacy of such compositions.

It is to be noted that the term "a" or "an" entity refers to one or more of that entity; for example, a protein refers to one or more proteins, or to at least one protein. As such, the terms "a" (or "an"), "one or more" and "at least one" can be used interchangeably herein. It is also to be noted that the terms "comprising", "including", and "having" can be used interchangeably.

The following examples are provided for the purposes of illustration and are not intended to limit the scope of the present invention.

EXAMPLES

Example 1

The following example demonstrates that a naturally derived mixture of proteins isolated from demineralized bovine bones (BP) induces spheroid formation and chondrogenesis in vitro in the mesenchymal precursor cell lines, 10T1/2 and $C_2C_{12}$.

Murine C3H/10T1/2 (ATCC No. CCL-226) embryonic mesenchymal stem cells and $C_2C_{12}$ adult myoblast cells (ATCC No. CRL-1772; derived from leg muscle) were obtained from the American Type Tissue Collection. 10T1/2 and $C_2C_{12}$ cells were proliferated in the presence of 10% and 15% FBS, respectively. Micromass cultures were performed as follows. Briefly, trypsinized cells were resuspended in media containing FBS at a concentration of $10^7$ cells/ml, and 10 μl of cells were placed in the center of a 24 well microtiter tissue culture dish. After 2–3 hours at 37° C., 1 ml of DMEM (for 10T1/2) or 1:1 DMEM:F-12 (for $C_2C_{12}$) media containing 1% Nutridoma and various concentrations of BP (prepared as described in Poser and Benedict, WO 95/13767, ibid.) were added. BP was present for the initial 48 hours and was not subsequently added.

The results presented in Table 1 show that BP concentrations greater than or equal to 20 ng/ml induced spheroid formation in >90% of 10T1/2 micromass cultures. In >90% of $C_2C_{12}$ micromass cultures, BP concentrations greater than or equal to 100 ng/ml induce spheroid formation.

TABLE 1

| | BP Concentration (ng/ml) | | | | | |
|---|---|---|---|---|---|---|
| Cell | 0 | 10 | 20 | 50 | 100 | >100 |
| 10T1/2 | − | − | + | + | + | + |
| $C_2C_{12}$ | − | − | − | +/− | + | + |

− = spheroid formation in 0% of micromass cultures
+/− = spheroid formation in <90% of micromass cultures
+ = spheroid formation in >90% of micromass cultures For $C_2C_{12}$ cells, the resulting spheroids were placed in Bouin's fixative for 24 hours and histology and immunocytochemistry was performed. The myosin F1.652 antibody was purchased from the Iowa Hybridoma Bank.

More specifically, for histology, spheroids were dehydrated and fixed for 20 minutes in absolute methanol at 4° C. Fixed sections were infiltrated and polymerized using the glycol methacrylate embedding technique. The polymerized plugs were then sectioned at 5 mm thickness using a JB-4 Sorvall microtome. Sections were mounted on silate-coated slides and stained with 0.2% Azure II at pH 1.

For immunocytochemistry, spheroids were snap-frozen in a 100% isopentane/dry ice solution, sectioned at 5 μm thickness using a Reichert-Jung cryostat, and mounted on silane-coated slides. Frozen sections were then fixed in 1% paraformaldehyde for 20 min. rinsed in 0.05 M Tris-Cl (pH 7.4), blocked with 1% BSA for 20 min. at room temperature, and incubated with either goat or mouse primary antibody for 1 hour at room temperature. After rinsing, the sections were blocked with 10% normal rabbit serum for 20 min. at room temperature. The sections were then treated with 1:2,000 biotinylated, rabbit anti-goat IgG followed by incubation with a 1:100 streptavidin-conjugated alkaline phosphatase. Each incubation was for 30 min. at room temperature. The mouse-antibody treated slides were incubated with an unlabeled rabbit anti-mouse (rat absorbed) antibody and then incubated with an alkaline phosphatase anti-alkaline phosphatase antibody. Each incubation was for 30 minutes at room temperature. The reaction was visualized with an alkaline phosphatase substrate, New Fuchsin. The slides were counterstained with Gill's #1 hematoxylin for 10 sec., dehydrated through graded alcohols, and cleared in Americlear xylene substitute. Polyclonal goat primary antibodies for type II collagen were diluted 1:200 in 0.5 M Tris-HCl (pH 7.4), 1% BSA, and 1% sodium azide prior to use.

Chondrogenesis is indicated by positive staining of sulfated proteoglycans with Azure at pH 1, morphology of a rounded cell type encompassed by a territorial matrix, and the presence of type II collagen. The collagen quantity was subjectively graded in duplicate samples with a '−' representing no stain detected and increasing '+'s reflecting increasing amounts and intensity of stain. Samples lacking the primary antibody received a '−' score.

Table 2 shows that BP (500 ng/ml) induces chondrogenic markers in 10T1/2 cells over a period of 28 days.

TABLE 2

| Marker | Correlated with | Days in culture 2 | 7 | 14 | 21 | 28 |
|---|---|---|---|---|---|---|
| Azure (pH 1) | Cartilage/sulfated proteoglycan | – | ++ | + | ++ | +++ |
| Morphology | Cartilage/rounded cells and territorial matrix | – | ++ | ++ | ++ | +++ |
| Type II Collagen | Cartilage | – | ++++ | ++++ | ++++ | ++++ |

Table 3 shows that in $C_2C_{12}$ cells, BP (1000 ng/ml) inhibits myosin production (an indicator of muscle) and induces type II collagen production (an indicator of cartilage) after three days in culture.

TABLE 3

| Marker | Indicative of: | Presence of Marker |
|---|---|---|
| Myosin | Muscle | – |
| Type II Collagen | Cartilage | ++++ |

Example 2

The following example demonstrates that a naturally derived mixture of proteins isolated from demineralized bovine bones (BP) inhibits myogenesis in a dose dependent manner in $C_2C_{12}$ cells.

For myogenesis inhibition experiments, 25,000 $C_2C_{12}$ cells were seeded in triplicate to a 24 well plate in DMEM media that contained 15% FBS. The next day (day 0), this media was replaced with media containing 1% Nutridoma +/– various concentrations of BP. Media was replaced every 2–3 days.

BP concentrations (0, 10, 20, 60, 100, 400, 1000, or 3000 ng/ml) were tested for the effect on $C_2C_{12}$ myotube formation. As shown in Table 4, a BP concentration of 10 ng/ml produced no morphological differences when compared to cultures lacking BP. However, at 20 and 60 ng/ml, BP substantially decreased the number of myotubes. Complete myotube inhibition was observed at BP concentrations above or equal to 100 ng/ml.

TABLE 4

| BP concentration (ng/ml) 0 | 10 | 20 | 60 | 100 | 400 | 1000 | 3000 |
|---|---|---|---|---|---|---|---|
| ++++ | ++++ | ++ | + | – | – | – | – |

Example 3

The following example demonstrates that a naturally derived mixture of proteins isolated from demineralized bovine bones (BP) quantitatively induces chondrogenesis of ATDC5 cells in a dose dependent manner.

In this experiment, 100,000 ATDC5 cells/25 μl media (DMEM:Ham's F-12 (1:1); 5% FBS; 50 U/ml penicillin; 50 mg/ml streptomycin) were seeded in triplicate to a 24 well plate (micromass culture). ATDC5 cells were deposited by T. Atusmi and are publicly available as Deposit No. RCB0565 from the Riken Cell Bank, 3-1-1 Koyadai, Tsukuba Science City, 305 Japan. After 1½ hour, 1 ml of the media was added. The next day, the same media containing various concentrations of BP, 50 μg/ml ascorbic acid, 5% FBS, and 10 mM β-glycerophosphate were added (day 0). This latter media was replaced every 3–4 days. To those skilled in the art, slight modifications can be made to this protocol to obtain a similar result. For example, fewer cells (e.g., 25,000–50,000) could be seeded to the bottom of the well (e.g., not in micromass culture). Media containing a serum substitute, such as 1% Nutridoma (Boehringer Mannheim) could be used in place of serum. Also, the cultures may contain different concentrations of serum or may contain or lack the ascorbic acid and/or the β-glycerophosphate.

To measure cartilage matrix production, an Alcian Blue staining method was used as previously described (von Schroeder et al, 1993, ibid.) with minor modifications. Briefly, after incubation with BP as described above, the culture media was removed and the cultures were washed three times with 1 ml of PBS. The cultures were then fixed with 10% neutral buffered formalin for 15 hours and washed twice with 0.5 N HCl. Cultures were stained for 1 hour at room temperature with a 0.5% Alcian Blue solution (pH 1.4). The stain was removed and the cultures were washed with PBS to remove the unbound stain. The blue stain was then extracted with guanidium HCl (4M, pH 1.7) at 70° C. for 18 hours, followed by measurement of absorption at 595 nm. The cultures were performed in triplicate. Using this method, glycosaminoglycan quantification was demonstrated to be proportional to $^{35}SO_4$ incorporation (Lau, et al., 1993, Teratology 47:555–563).

Figure 5:
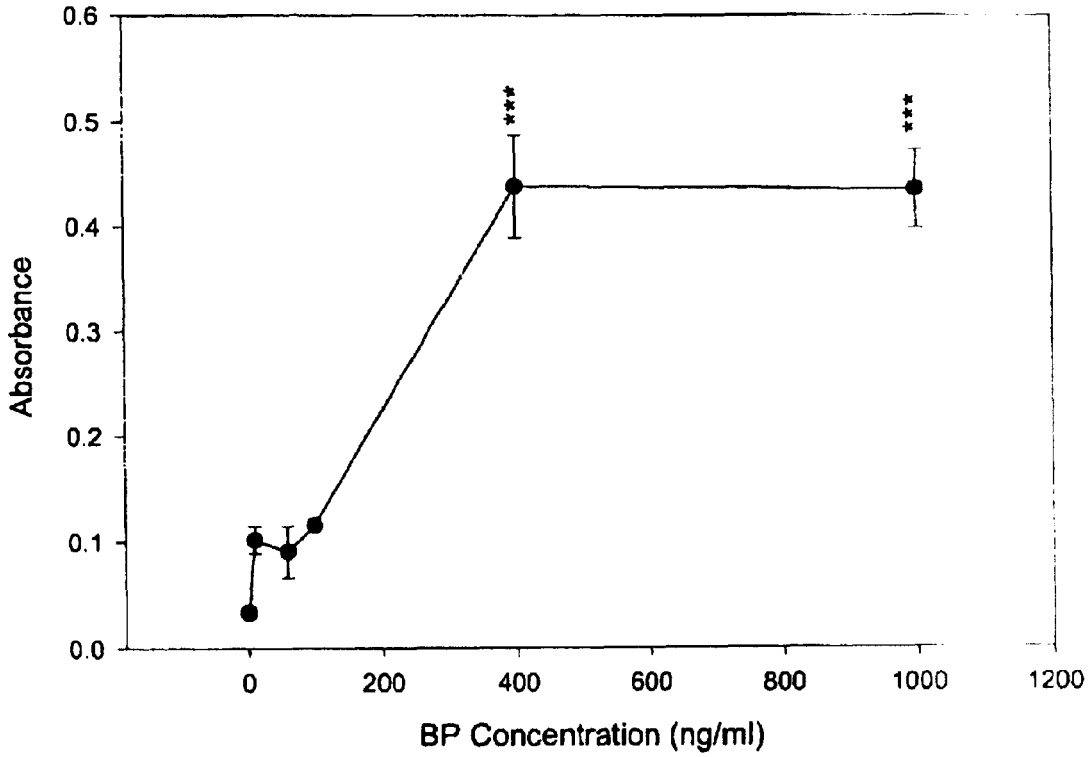
FIG. 5 is a line graph showing quantitation of Alcian Blue staining of ATDC5 micromass cultures.

To determine the effect of BP on chondrogenesis, 0, 10, 20, 60, 100, 400, and 1000 ng/ml BP were added to chondrogenic ATDC5 micromass cultures and, after 7 days, the cultures were stained with Alcian Blue. Qualitative, microscopic evaluation showed that cultures lacking BP contained no positive staining and cultures containing low BP concentrations (10, 20, and 60 ng/ml) showed diffuse staining. With higher doses of BP (100, 400 and 1000 ng/ml BP), both staining intensity and the number of positively stained focal cell areas increased in a dose dependent manner. Cultures treated with 400 and 1000 ng/ml BP contained positively stained focal clusters consisting of rounded cells encompassed by a territorial matrix (data not shown). Negatively stained areas were also present. Quantitation of Alcian Blue staining (FIG. 5) revealed that BP concentrations as low as 10 ng/ml significantly increased Alcian Blue content compared to control cultures lacking BP ($p<0.0005$). Maximal Alcian Blue staining was observed at 400 ng/ml BP.

Figure 6:
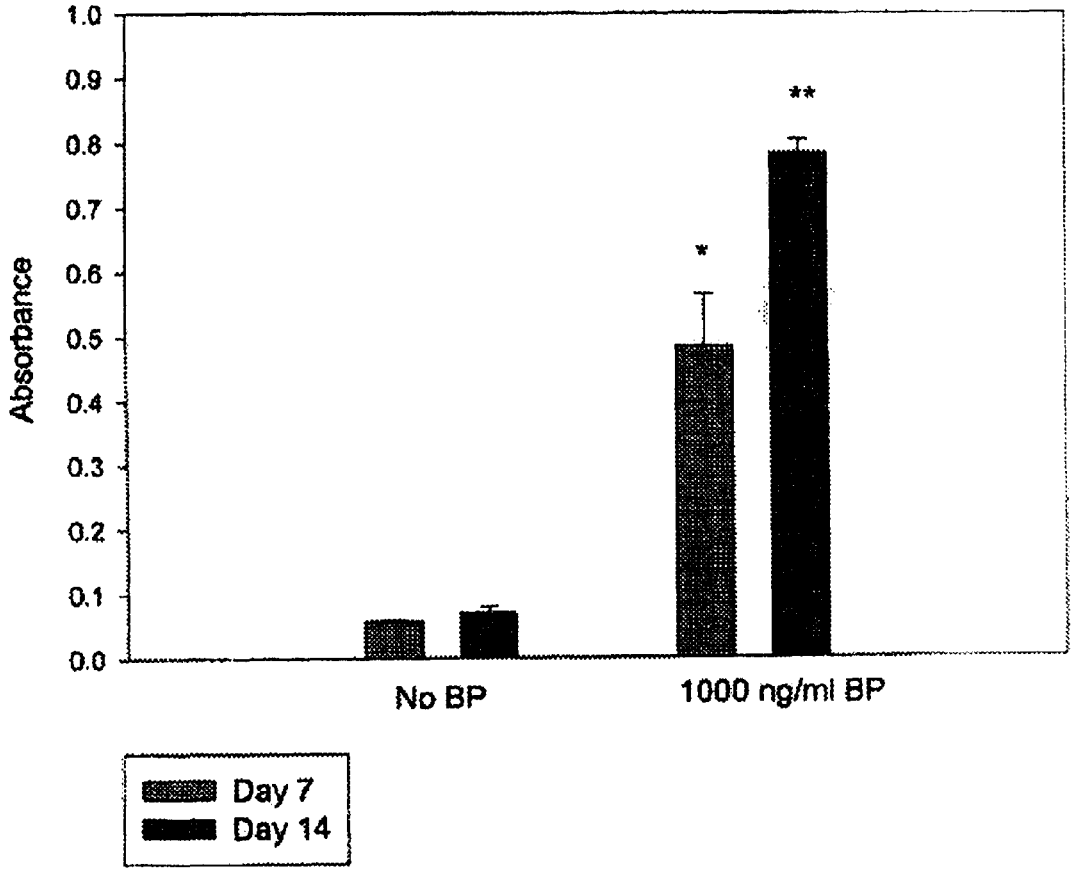
FIG. 6 is a bar graph showing quantitation of Alcian Blue staining of ATDC5 micromass cultures in Nutridoma-containing media at 7 and 14 days.

BP also stimulates chondrogenesis in cultures containing a serum substitute, Nutridoma, and this stimulation occurs over 14 days. In the absence of BP, very little Alcian Blue staining was observed at days 7 and 14 (FIG. 6). However, cultures containing 1000 ng/ml BP significantly ($p<0.001$) stimulated chondrogenesis 8.5 and 11.2 fold at days 7 and 14, respectively, compared to cultures lacking BP (FIG. 6).

Figure 7:
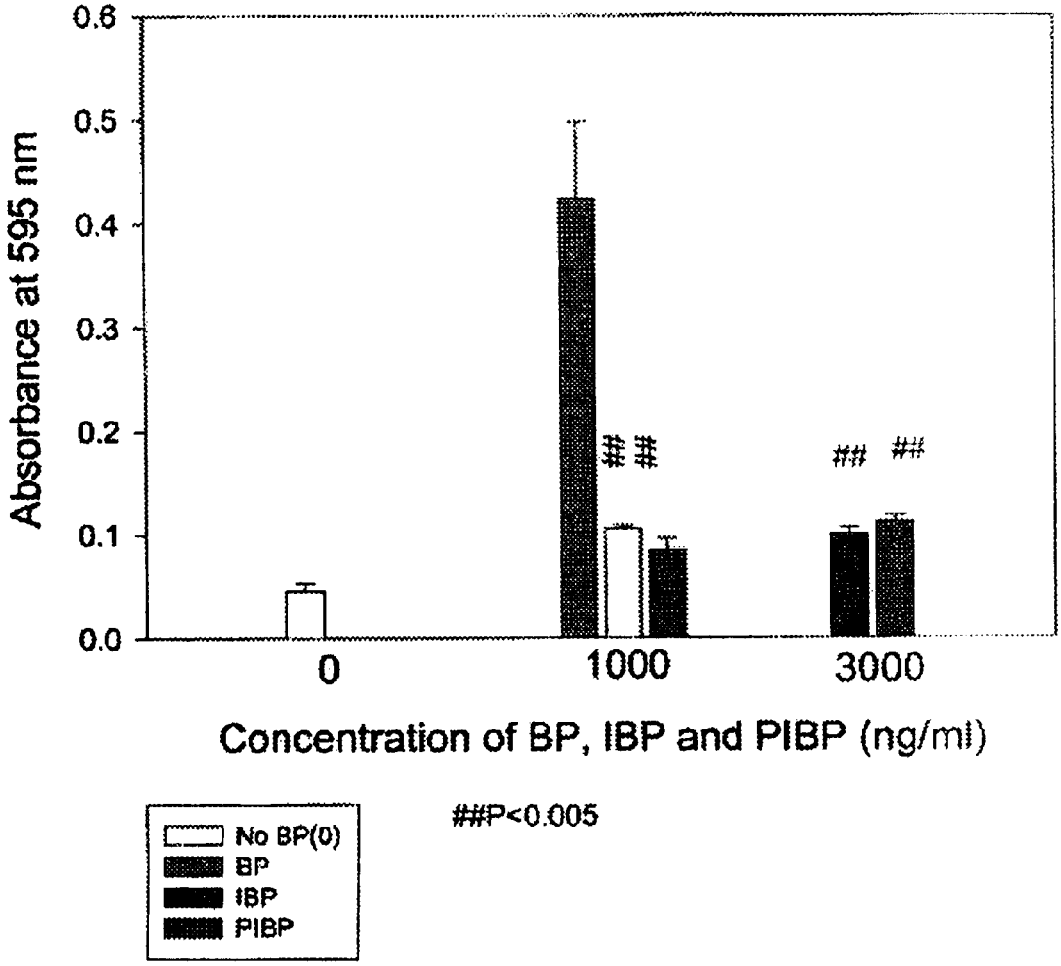
FIG. 7 is a bar graph showing quantitation of Alcian Blue staining of ATDC5 micromass cultures containing HPLC fractions of proteins isolated from demineralized bovine bones.

To determine whether other fractions isolated from bone have a similar activity as BP, the following experiment was performed. BP was purified as previously described (Poser and Benedict, PCT Publication No. WO95/13767). However, after the BP containing fractions were collected from the HPLC, two fractions, IBP and PIBP, that were more hydrophobic than BP, were also collected. The chondrogenic activity of BP, IBP and PIBP was tested on ATCD5 cells. FIG. 7 shows that both IBP and PIBP induce significantly less ($p<0.005$) chondrogenesis than BP.

To determine whether different lots of BP differed significantly for chondrogenesis, two lots were tested at two concentrations. Table 5 shows that the chondrogenic activity is not significantly different between two different BP lots.

TABLE 5

| | Absorbance | |
|---|---|---|
| BP Lot # | 200 ng/ml | 300 ng/ml |
| 97182 | 0.364 +/− 0.019 | 0.535 +/− 0.031 |
| 98001 | 0.353 +/− 0.041 | 0.484 +/− 0.043 |

Example 4

The following example describes a procedure for preparation of a cartilage repair product of the present invention, configured as a sheet.

Bovine tendon type I collagen, obtained from ReGen Biologics, Inc., was placed in one syringe. The appropriate volume of 10 mM acetic acid was placed in another syringe. For sponges that contain BP, the appropriate dose of BP was placed in the syringe containing 10 mM acetic acid. The syringes were coupled, and the contents of each syringe were mixed to produce a 2% collagen (w/w) slurry. After an overnight incubation, the preparation was placed in molds of appropriate thickness, frozen at −20° C. for more than 4 hours, and lyophilized until dry. Approximate implant dimensions for the sheet are length: 15.5 mm; width: 4.8 mm; and thickness: 1.2 mm.

Example 5

The following example describes the procedure for surgical implantation of a cartilage repair product of the present invention which is configured as a sheet.

Adult castrated male Capra hircus goats weighing 50–70 pounds were used in this study. After pre-anesthesia administration, the goats were anesthetized with an inhalation anesthetic (IsoFlurane). The hind limbs of each goat were clipped, scrubbed, and draped in preparation for the surgical procedure. An incision was made over the medial aspect of the knee (stifle) joint. The sartorial fascia was dissected to expose the medial collateral ligament (MCL). A wedge shaped femoral bone block centered on the MCL was created with an oscillating saw and osteotome. The block was then drilled and tapped for later reattachment using a 3.5 mm bicortical screw. The bone block was then elevated to expose the surface of the medial meniscus leaving the coronary ligaments intact. A longitudinal tear was placed in the central, avascular portion of the meniscus using a scalpel. Four treatments were tested in the defect as follows. Group I: nothing was placed in the defect, but the defect was repaired using 1-0 non-absorbable sutures and a horizontal mattress technique (i.e., a conventional repair method); Group II: a collagen sheet was sutured into the defect using the method of Group I; and, Group III: a collagen sheet containing 35 μg BP was sutured into the defect using the method of Group I.

After reduction and fixation of the bone block with a screw and washer, the sutures were tied outside the capsulate. The subcutaneous tissues were then closed with absorbable suture and subcuticular 3-0 prolene skin closure. After recovery from anesthesia, the goats were placed in holding pens and then placed in an outdoor facility with unrestricted activity.

After 8 weeks, the animals were euthanized with a pentobarbitol sodium solution (100 mg/kg IV) solution. The menisci were fixed in a 10% neutral buffered formalin solution. Tissue sections for the menisci were then stained with H+E.

Group III defects that contained 35 μg BP were filled with tissue from the superior to inferior sides of the meniscus and the reparative tissue was integrated into the endogenous meniscus tissue. In addition, the endogenous meniscus tissue immediately adjacent to the defect was more cellular than normal endogenous meniscus, indicating a reparative response. In contrast, Group I and II defects remained empty; no evidence of healing was observed.

Example 6

The following example describes the procedure for surgical implantation of a cartilage repair product of the present invention which is configured to replace a segmental meniscal cartilage defect.

If a meniscal repair can not be accomplished (i.e., such as by using a product of the present invention configured as a sheet) due to the severity of the tear or poor quality of the tissue, then preparation of the meniscal rim is undertaken by removing the torn portions of the cartilaginous tissue. A cartilage repair product of the present invention can be configured to replace the segmental meniscal cartilage defect, thereby serving to both regenerate and repair meniscal cartilage. The surgical procedure, in the absence of the cartilage repair product of the present invention, has been previously described by Stone and Rosenberg (cites). The following procedure describes a modification of the procedure of Stone and Rosenberg, incorporating the use of a cartilage repair product of the present invention.

Briefly, the torn, fragmented pieces of native meniscal cartilage are removed, and the attachment sites for meniscal horns are anatomically placed or the natural peripheral rim and horns are preserved. Using the surgical techniques described by Stone and Rosenberg, a cartilage repair matrix configured as a collagen meniscus implant (CMI; having the shape and mechanical characteristics of the meniscus), which is associated with a cartilage repair composition according to the present invention, is implanted and fixed to the meniscal rim. During the surgery, the periphery of the meniscal implant must be attached securely enough to permit axial and rotational loads, and the surrounding capsule and ligaments of the knee joint must be neither excessively violated nor constrained by the fixation technique.

In some cases, a cartilage repair product of the present invention which is configured as a sheet can be fixed to the meniscus rim using the same surgical procedures as described for the CMI product above. This combination use of the cartilage repair product of the present invention is illustrated schematically in FIG. 8. Use of such a sheet optimizes the integration between the meniscal rim and the CMI by providing a thin, porous collagen containing the cartilage repair composition. The sheet provides an interface in which cells can quickly infiltrate and react with the cartilage repair composition. In this embodiment, the cartilage repair product configured as a sheet contains the cartilage repair composition of the present invention, and the cartilage repair product configured as a CMI may or may not be associated with the cartilage repair composition.

Example 7

The following experiment demonstrates that a cartilage repair product of the present invention enhances and induces meniscus regeneration in both vascular and avascular meniscal tissue in vivo.

One hind leg was operated on in 1–2 year old female sheep. Briefly, the surgical approach was to make an incision in the skin and subcutaneous tissues from the distal fourth of the femur distally to the proximal fourth of the tibia. A bone block that contained the origin of the medial collateral ligament was then removed from the femoral condyle. The tibia was abducted and externally rotated. Using a 3 mm dermal biopsy punch (Miltex), two defects were created in the vascular/avascular zone of the medial meniscus. The Collagen Meniscus Implant (CMI) was obtained from ReGen Biologics. Using a 4 mm dermal biopsy punch (Miltex), CMI sponges were cut to size. The 4 mm implants were press-fit into the meniscal defects. CMI either lacked or contained BP (69 μg/mg collagen). To produce CMI containing BP, the following protocol was followed. A saturating volume of 10 mM acetic acid solution that contained BP was added to the 4 mm CMI sponges. The sponges were placed in a humidified environment at room temperature for 30 minutes, frozen at −20° C. for more than 4 hours, and then lyophilized until dry.

The animals were sacrificed after four weeks and the menisci were fixed in a 10% neutral buffered formalin solution. Tissue sections were stained with Azure B at pH 1 and 4.5. Cells infiltrated the CMI matrix both in the presence or absence of BP, however, histology results demonstrated that only undifferentiated fibroblast cells were present in the implant that lacked BP (data not shown). In contrast, the BP impregnated implant contained differentiated fibrochondrocytes (data not shown). Fibrochondrocytes were identified by rounded cell shape and cells surrounded by positively staining lacunae. In addition, CMI sponges that lacked BP contained cells that did not stain with antibodies against type II collagen. In contrast, CMI sponges that contained BP contained cells that stained positively with antibodies against type II collagen.

Example 8

The following example demonstrates that a cartilage repair product of the present invention enhances and induces articular cartilage repair in vivo.

Five 8 month old (skeletally mature) New Zealand White Rabbits were used in this experiment. Bilateral defects, 8 mm long, 3 mm wide, and 3 mm deep, were produced in the trochlear groove of each knee. For each rabbit, a 2% collagen sponge 8 mm long, 3 mm wide and 3 mm deep, was placed in each knee defect, with one knee receiving the sponge in the absence of BP, and one knee receiving the sponge containing 40–45 μg of BP. Autologous fibrin was prepared from 50 ml of rabbit blood using the alcohol precipitation method according to Kjaergard et al., 1992, Surg. Gynecol. Obst. 175(1): 72–73. Approximately 20 μl of fibrinogen was placed on top of the collagen and was polymerized with 10 μl bovine thrombin (Gentrak). After 2 months, the animals were sacrificed.

A 500 μm slab of the defect area was embedded in glycol methacrylate after fixation in cold methanol and stained with azure B at pH 1 and 4.5. An adjacent 500 μm slab was fixed and decalcified with EDTA in 4% paraformaldehyde and embedded in paraffm. Serial sections were digested with chondroitinase ABC and stained with hemotoxilin and eosin.

Histologically, defects that contained the collagen sponge only produced more immature tissue than defects that contained collagen+BP. Without added BP, the bone region was filled with fibrocartilage and fibroblastic tissue. In contrast, defects containing BP were filled with osteoblasts and contained a bone morphology. The cartilage area, in the absence of BP, was often 3 mm dep, rather than the normal 0.5–0.7 mm deep. With BP added, the cartilage surface thickness was nearly identical to the endogenous cartilage thickness. In addition, polarized light microscopy revealed that the BP treated defects contained a more mature collagen fiber architecture than defects that did not contain BP.

Example 9

The following example demonstrates that bone protein (BP) is a complex mixture of proteins which includes at least: TGFβ1, TGFβ2, TGFβ3, BMP-2, BMP-3, BMP-4, BMP-5, BMP-6, BMP-7, CDMP, FGF-I, osteocalcin, osteonectin, BSP, lysyloxidase, cathepsin L pre, albumin, transferrin, Apo A1 LP and Factor XIIIb.

The present inventors used standard techniques and reagents available in the art to identify these proteins within bone protein (See for example, "Current Protocols in Protein Science", Ed. J E Coligan et al.; 1995–1998, John Wiley and Sons, Inc.; "Protein Purification: Principles and Practice" Scopes and Verlas; 1982). The proteins which have been identified as present in BP by at least one of these assays are identified in Table 6.

TABLE 6

BP COMPOSITION

| | Mass (kD) | | | Presence in BP | | |
|---|---|---|---|---|---|---|
| Compound | Literature | Experimental | pI | ELISA | Immunoblot | Mass. Spec./ Sequencing |
| TGFβ Superfamily | | | | | | |
| TGFβ1 | 12.5$^{Ob}$ | 12.5 | | YES | YES | |
| TGFβ2 | 12.7$^{T}$ | 12 | 7.7$^{T}$ | | YES | YES |
| TGFβ3 | | | | | YES | |
| BMP-2 | 16-18$^{Ob}$ | 16 | 7.9$^{T}$ | NO | YES | |
| BMP-3 | 16-18$^{Ob}$ | 31 | 8.5$^{T}$ | YES | YES | |
| BMP-4 | 16-18$^{Ob}$ | | 7.7$^{T}$ | | YES | |
| BMP-5 | 16-18$^{Ob}$ | | 8.3$^{T}$ | | YES | |
| BMP-6 | 16-18$^{Ob}$ | 17 | 8.6$^{T}$ | | YES | |
| BMP-7 | 16-18$^{Ob}$ | 17.5 | 8.1$^{T}$ | YES | YES | |
| CDMP (pen) | | | | YES | YES | |
| Growth Factors | | | | | | |
| PGF-1 (acidic) | 16$^{Ob}$ | 13 & 15 | 5.4 | | YES | |
| Bone Matrix Proteins | | | | | | |
| Osteocalcin | 5.8 | <10 | | YES | YES | |
| Osteonectin | 32 | 33 | | NO | YES | |
| ESP (BSP-II) | 35$^{T}$ | | | | YES | |
| Lysyloxidase | | | | | | YES |
| Cathepsin L Pre | 37.4$^{T}$ | 38 | 6.6 | | NO | YES |
| Serum Proteins | | | | | | |
| Albumin | 66$^{T}$ | 68 | 5.6$^{T}$ | YES | YES | |
| Serotransferrin Precursor | 76$^{T}$ | 80 | 6.5$^{T}$ | | YES | YES |
| Apo-A1-Lipoprotein | 28 | 36 | 5.6 | | YES | |
| Factor XIIIb Precursor | | 80 | | | | YES |

Additionally, intracellular proteins identified in Bone Protein include intracellular proteins: Dynein associated protein, protamine II, histone-like protein, L6 (ribosomal protein), and L32 (ribosomal protein). Other serum proteins that have been identified in BP include α2 microglobulin. Other extracellular matrix (bone matrix) proteins that have been identified include Frizzled related protein. All such proteins can be included, if desired, in a composition of the present invention.

Several preparations of protein mixtures or Bone Protein or derivatives thereof were examined to provide a gross estimate of the amount of several of the proteins in Table 6. Specifically, several different lots of BP and AX fractions that were extracted at pH 9.0, 9.5 and 10.0 (See Example 11) were examined by standard Western blot analysis using antibodies against TGFβ1, TGFβ2, BMP-3 and BMP-7. The resulting radiograph was scanned using a Sharp JX-330 scanner and the lane volume was calculated using Image-Master ID software. To quantitate the amount of TGFβ1 in BP and its derivatives, recombinant bovine TGFβ1 was run as a standard (2, 4, 8 and 16 ng; Promega) and anti-bovine TGFβ1 was used. To calculate the amount of TGFβ1, TGFβ2, BMP-3, or BMP-7 in any given sample, the following formula was utilized: (lane volume sample/lane volume standard TGFβ1)×(quantity of standard TGFβ1 loaded). Anti-bovine TGFβ antibody was used. This method is a specific estimator of the amount of TGFβ1 in the samples and a gross estimator of the quantities of TGFβ2, BMP-3 and BMP-7 in the mixtures. Only gross estimates of TGFβ2, BMP-3 and BMP-7 can be made, because bovine standards and bovine antibodies for each of these three proteins are not available (human antibodies were used for these proteins, and quantities were estimated based on the TGFβ1 standard). The low and high quantity estimates for each of the four proteins over all of the compositions tested is shown in Table 7. For these compositions, the ratio (w/w) of TGFβ1 to all other proteins in the mixture is from about 1:1000 to about 1:100.

Those skilled in the art recognize that bovine and human TGFβ-1 have identical amino acid sequences and, therefore, that bovine TGFβ-1 and rhTGFβ-1 should have identical activities. Those skilled in the art also recognize that high purity TGFβ-1 can be isolated from bovine bone using methods disclosed by Seyedin (Ogawa et al., Meth. Enzymol., 198:317–327 (1991); Seyedin et al., PNAS, 82:2267–71 (1985)).

TABLE 7

| | TGFβ-1 | TGFβ-2 | BMP-3 | BMP-7 |
|---|---|---|---|---|
| Low quantity estimate (ng/μg protein in composition) | 0.9 | 8.4 | 3.8 | 1.5 |
| High quantity estimate (ng/μg protein in composition) | 9.8 | 114.0 | 89.2 | 43.5 |
| Low quantity estimate (% of total proteins) | 0.09 | 0.84 | 0.38 | 0.15 |
| High quantity estimate (% of total proteins) | 0.98 | 11.4 | 8.9 | 4.3 |

Example 10

The following example demonstrates that the cartilage-inductive activity of bone protein (BP) and protein mixtures derived from the complex mixture of proteins in BP is superior to the cartilage-inductive activity of individual recombinant protein components, as determined using a standard in vivo rodent subcutaneous assay.

A. In the following experiment, a rodent subcutaneous assay and grading system developed by Sulzer Biologics, Inc. (Denver, Colo.), was used to evaluate the cartilage- and bone-inductive capabilities of recombinant BMP-2 (provided to Sulzer Biologics, Inc. by Genetics Institute). The results were then compared to data for BP which was generated in the same assay and using the same grading system.

To perform the Sulzer Biologics, Inc. rat subcutaneous assay, a matrix is prepared from a suitable material. When the material was type I collagen, a dispersion of 4% w/w collagen was prepared using bovine type I collagen and 1% glacial acetic acid. Collagen discs/sponges were formed in molds, and then frozen and lyophilized. For the assay, the discs were loaded with the composition (e.g., bone protein, a subset of bone protein, a growth factor) by incubation of the disc with the composition at room temperature for about 30 minutes, followed by freezing and lyophilization of the discs. The discs were implanted into Long-Evans rats in subcutaneous positions. In all of the experiments described in this example and other examples below, 5–10 rats were used per treatment and the composition treated collagen disc/sponge (or other material in Example 14) was implanted for three weeks. At the end of three weeks, the rats were euthanized, and the explants were surgically removed, histologically processed, and graded. The grading scale utilized for bone-inductive activity in the rodent subcutaneous assay, which was developed by Sulzer Biologics, Inc., is shown in Table 8. The grading scale utilized for cartilage-inductive activity in the rodent subcutaneous assay, which was also developed by Sulzer Biologics, Inc., is shown in Table 9.

TABLE 8

| | |
|---|---|
| Zero (0): | No residual implanted sample found.<br>Section shows no silver stained deposits or those deposits are associated with acellular events, (e.g., dystrophic mineralization of collagen fibrils).<br>Explants generally small, soft and avascular. |
| One (1): | Focal areas of silver stained mineralized tissues are of cellular origin. This may include mineralized cartilage as well as mineralized osteoid matrix.<br>Silver stained areas are randomly located throughout the explant, and typically encompass less than 50% of the explant.<br>Generally smaller than original implants. |
| Two (2): | Silver stained areas are mineralized cartilage or very early woven bone.<br>Osteoblasts appear in rows of only about 6 to 10 cells.<br>If osteoid is present, it is generally present on less than 10% of the mineralizing tissue in the section.<br>Small areas of hematopoietic marrow elements may be visible (generally sinusoids containing red blood cells). |
| Three (3): | Sheets of active osteoblasts, (e.g., cells are plump and cuboidal or polygonal) generally consisting of 10 or more cells, appear in less than 50% of the active mineralized portion. They are generally not continuous.<br>Bone associated with osteoblasts is generally woven, containing some osteocytes.<br>Woven bone appears at outer regions of explant and may have breaks of fibrous tissue or mineralized cartilage <10% of surface.<br>Some hematopoietic marrow element may be visible. (Hemopoietic cords and sinusoids containing red blood cells). |
| Four (4): | Mineralized tissue at the periphery is generally not woven, but a mature band containing lamellar bone.<br>Mature bone is associated with continuous osteoblast surfaces in at least 50% of bony area.<br>Osteoid contains active osteoblasts and a visible osteoid matrix.<br>Bone marrow as evidenced by granulocytes, hemopoietic cords and sinusoids is common.<br>Evidence of osteoclastic resorption (presence of osteoclasts and/or Howship's lacunae). |
| Five (5): | Solid rim of mature bone with few breaks around outer edge of explant.<br>Mature bone contains osteocytes in organized patterns.<br>Mature bone contains wide dark staining (in TBO stain) osteoid.<br>Osteoid seams are continuous with few breaks; very tick with osteoblasts that may be flattened.<br>Bone marrow contains hemopoietic cords packed with cells, granulocytes, sinusoids and adipocytes.<br>Trabecular bone in marrow is resorbing and may appear as |

TABLE 8-continued

| |
|---|
| focal areas with little branching.<br>Osteoclastic resorption is occurring on outer edge of mature bone (presence of osteoclasts and/or Howship's lacunae).<br>Explant center may contain mature woven bone or be infarcted and largely acellular.<br>No evidence of chondrocytes. |

TABLE 9

| A | B | C | D | E |
|---|---|---|---|---|
| 0 | No | N/A | N/A | N/A |
| 1 | Yes | No | No | No |
| 2 | Yes | Yes | No | No |
| 3 | Yes | Yes | Yes | No |
| 4 | Yes | Yes | Yes | Yes |

KEY:
A = Score; B = Presence of mineralized tissue; C = some non-mineralized cartilage; D = non-mineralized cartilage area is comparable to bone area; cartilage is in ring >50% of circumference of explant; often heavy cartilage stain; E = non-mineralized cartilage area is greater than bone area; often very little or no mineralization resulting form bone or cartilage.

BP, administered at a dose of 10 μg on a collagen sponge, routinely scores between 1.5 and 2.2 for cartilage, and between 2.0 and 2.5 for bone. In contrast, recombinant human BMP-2 gave the results shown in Table 10, revealing that BMP-2 has both a lower bone and cartilage score as compared to BP.

TABLE 10

| BMP-2 Rat subcutaneous assay | | | |
|---|---|---|---|
| | 1.0 μg | 3.5 μg | 10 μg |
| Bone Score | 1.2 ± 0.1 | 1.3 ± 0.1 | 1.7 ± 0.2 |
| Cartilage Score | 1.0 ± 0.0 | 1.0 ± 0.0 | 1.0 ± 0.0 |

B. TGFβ-1 and -2 were initially identified by the ability to stimulate chondrogenesis in vitro. However, it is known in the art that TGFβ1–5, and growth factors such as FGF and PDGF, do not induce bone or cartilage in the rat subcutaneous assay, such as the in vivo rodent ectopic assay (e.g., both TGFβ-1 and -2 are unable to initiate cartilage or bone formation; only fibrous tissue is observed). This is confirmed by the results shown below with recombinant TGFβ1. The assay was performed using Sulzer Biologics, Inc. rat subcutaneous assay and grading system as described in section (A) above. Table 11 shows that recombinant human TGFβ1 does not induce bone or cartilage in this assay. In contrast, Bone Protein (BP), administered at a dose of 10 μg, routinely scores between 1.5 and 2.2 for cartilage, and between 2.0 and 2.5 for bone (see examples below).

TABLE 11

| TGFβ1 Rat subcutaneous assay | | |
|---|---|---|
| | 10 μg | 35 μg |
| Bone Score | 0.0 ± 0.0 | 0.0 ± 0.0 |
| Cartilage Score | 0.0 ± 0.0 | 0.0 ± 0.0 |

Example 11

The following example demonstrates that another mixture of proteins derived from a modified purification process for BP that contains BMP-2, BMP-3, BMP-7, and TGFβ-1 produces comparable bone, but greater quantities of cartilage as compared to BP.

BP is normally purified using anion exchange (AX), cation exchange (CX) and high performance liquid chromatography (HPLC) steps (PCT Publication No. WO95/13767, incorporated herein by reference in its entirety). Such a method is described in detail above and in U.S. Pat. No. 5,290,763, incorporated herein by reference in its entirety.

Typically, proteins are eluted from the AX column at pH=8.5. For this experiment, proteins were eluted from the AX column at pH 9.0, 9.5, and 10.0. The samples were then purified across the CX and HPLC columns as described previously (PCT Publication No. WO95/13767). Each HPLC fraction that was extracted at the above pHs were assayed by Western blot for the presence of BMP-2, BMP-3, BMP-7, TGFβ-1, and TGFβ-2.

Extraction of the AX column with increasing pH resulted in increased quantity of BMP-2, BMP-3, BMP-7, and TGFβ-1 in BP. At a pH of 9.0, BMP-2 and BMP-7 quantities show the greatest increase, whereas TGFβ-1 and BMP-3 show limited or no increase compared to pH 8.5. Increasing quantities of these factors have no significant effect on the bone score and slightly increase the cartilage score (Table 12). At pH 10, the TGFβ-1 quantity increases much more than the increase for BMP-2, -3, and -7, and the pH 10 fraction shows the greatest cartilage score, indicating a specific role for TGFβ1 in cartilage induction within the mixture of proteins. The HPLC purified fractions (10 μg) were tested in the rat subcutaneous model, the results of which are shown in Table 12.

TABLE 12

| pH | 8.5 | 9.0 | 9.5 | 10.0 |
|---|---|---|---|---|
| Bone Score | 2.0 ± 0.0 | 2.2 ± 0.2 | 2.0 ± 0.0 | 2.1 ± 0.3 |
| Cartilage Score | 1.5 ± 0.2 | 2.0 ± 0.1 | 1.9 ± 0.1 | 2.3 ± 0.1 |

Example 12

The following example demonstrates that a composition purified from BP and including BMP-2, BMP-3, BMP-7 and TGFβ-1, contains components required for cartilage formation.

To obtain specific protein subsets of BP, proteins within BP were separated on a hydroxyapatite column. The void material contained proteins that eluted with <120 mM $KPO_4$ buffer. During the elution, the pH gradient ranged from 6.0–7.4. 10 μg of each fraction was added to collagen sponges and the rodent subcutaneous assay was performed as described in Example 10 above. In addition, an equivalent quantity of each fraction was loaded onto a protein gel and a Western blot was performed with antibodies against BMP-2, BMP-3, BMP-7, and TGFβ-1 (Table 13). A (−) indicates no signal detected and a (+) indicates that a signal was detected.

TABLE 13

| Marker | Void | Peak | Wash | BP |
|---|---|---|---|---|
| BMP-2 | − | + | + | + |
| BMP-3 | − | + | + | + |
| BMP-7 | − | + | + | + |
| TGFβ-1 | − | + | + | + |

The data in Table 14 demonstrates that a BP fraction containing BMP-2, 3, 7 and TGFβ-1, contains proteins which are required components for BP cartilage and bone inductive activity.

TABLE 14

| Measure | Void | Peak | Wash | BP |
|---|---|---|---|---|
| Bone score | 0.2 | 2.4 | 2.4 | 2.2 – 2.5 |
| Cartilage score | 0.0 ± 0.0 | 2.4 ± 0.2 | 2.0 ± 0.0 | 2.2 ± 0.2 |

Example 13

The following example demonstrates that increasing amounts of high levels of a pure source of TGFβ1, when added exogenously to a complex mixture of osteogenic/chondrogenic proteins, leads to the progressive loss of bone and mineralized cartilage formation, and the progressive formation of non-mineralized cartilage in vivo.

Bone Protein (BP) naturally contains TGFβ1, in addition to a variety of other proteins, as described in various examples above. Examples 11–12, however, indicated that TGFβ1 may be particularly important for the chondrogenic abilities of the osteogenic/chondrogenic mixture. Therefore, the present inventors sought to determine whether an exogenous source of substantially pure TGFβ1 (i.e., recombinant or purified), when provided in a high concentration relative to the amount of other osteogenic/chondrogenic proteins in a mixture such as BP, would influence the chondrogenic induction capabilities of the composition as a whole.

In this example, recombinant human TGFβ1 (rhTGFβ1) was added in increasing amounts (0, 1 μg, 3.5 μg, 10 μg) to 10 μg of Bone Protein (BP). The mixture was then placed on collagen sponges and the rodent subcutaneous assay was performed as described above in Example 10. The results of the different ratios of rhTGFβ1 to BP for cartilage and bone induction are shown below in Table 15. It is noted that since the quantity of individual BMP proteins in BP ranges from about 0.01% to about 9% (minimum and maximum quantities), the effective ratio of TGFβ1 to at least one BMP in the mixture ranges from greater than 10:1 to greater than 1000:1.

TABLE 15

| rh TGFβ-1:BP | 0:1 | 1:10 | 1:2.9 | 1:1 |
|---|---|---|---|---|
| Bone Score | 2.0 ± 0.0 | 2.2 ± 0.2 | 1.0 ± 0.0 | 1.0 ± 0.0 |
| Cartilage Score | 1.4 ± 0.2 | 1.8 ± 0.2 | 3.8 ± 0.2 | 3.7 ± 0.2 |

Table 15 shows that the osteogenic and chondrogenic activity previously demonstrated herein for BP can be altered to progressively decrease bone production and increase cartilage production by the addition of increasing amounts of exogenous TGFβ1. Surprisingly, at high concentrations of TGFβ1, the composition is primarily chrondrogenic, with very little osteogenic activity observed.

Example 14

The following example demonstrates that different cartilage repair matrices combined with BP induce cartilage formation in vivo according to the present invention.

A. This example demonstrates the use of a poly lactic acid:polyglycolic acid material that contains BP for bone and cartilage formation.

A 60% (v/v) solution of polylactic acid: polyglycolic acid (PLGA) (50:50) in N-Methyl Pyrrilidone was made. Collagen (6 mg) was pressed in a Delrin mold. The PLGA (140 mg) was added and mixed. BP (100 μg) contained in a 10 mM HCl solution (100 microliters) was added and all components were mixed together to form a solid disc. This mixture was pressed into a mold and incubated at room temperature for one hour and then implanted into rats in the rat subcutaneous assay as described in section 5. Histology was performed after one month of implantation. Table 16 shows that BP combined with the PLGA matrix induces cartilage formation in this in vivo model.

TABLE 16

| | PLGA-collagen-BP |
|---|---|
| Bone score | 2.6 ± 0.7 |
| Cartilage Score | 1.2 ± 0.5 |

B. In this assay, a 3% collagen Type I/1% collagen Type IV (Sigma) composite sponge was made using the normal preparation method as described in Example 4 of the application. This matrix, containing 10 μg BP, was implanted into rats in the rat subcutaneous assay as described in section 5, and histology was performed after three weeks. Table 17 shows that BP combined with the matrix containing both type I and type IV collagen induces cartilage formation in this in vivo model.

TABLE 17

| | Type I/IV |
|---|---|
| Bone Score | 1.2 ± 0.2 |
| Cartilage Score | 1.2 ± 0.2 |

C. This experiment demonstrates the use of an injectable collagen gel containing BP that induces bone and cartilage. A BP solution (1 mg/ml) contained in 10 mM HCL (5 ml) was added to collagen (30 mg/ml). The solutions were mixed until a jelly-like consistency and were incubated at 4° C. overnight. In the absence of an incision, 100 microliters of the gel was injected subcutaneously into the rat. Table 18 demonstrates that BP in a matrix in the form of a gel induces cartilage formation in this in vivo model.

TABLE 18

| | Collagen gel + 100 μg BP |
|---|---|
| Bone score | 3.5 ± 0.5 |
| Cartilage Score | 2.0 ± 1.0 |

D. This experiment demonstrates that cartilage repair matrices containing triethanolamine and collagen in the form of a gel (basic pH), combined with BP, induce cartilage formation in vivo.

For basic collagen preparation, 0.5 gram TEA was added to 99.5 gram dI water to pH 9.9. To make a 2% collagen gel, 2.0 gram collagen was added to pH 8.8. The mixture was incubated at room temperature for one hour and then frozen and lyophilized 48 hours. The mixture was reconstituted in 10 mM HCL (containing 35 micrograms of BP) as 3 and 6% collagen sponges. The gel was delivered through a #18 or #20 needle in a 100 microliter volume. After drying, the resulting sponges were 80% collagen and 20% TEA by weight. Table 19 demonstrates that both 3 and 6% collagen TEA sponges combined with BP induce cartilage in this in vivo system.

TABLE 19

| AED | 6% collagen TEA + 35 μg BP | 3% collagen TEA + 35 μg BP |
|---|---|---|
| Bone Score | 3.0 ± 0.8 | 2.3 ± 1.0 |
| Cartilage Score | 2.3 ± 0.3 | 2.3 ± 0.3 |

E. This experiment demonstrates that cartilage repair matrices containing collagen at acidic pH in the form of a gel, combined with BP, induce cartilage formation in vivo. To prepare the acidic pH collagen gel, to 995 ml dI water, 5.0 ml 1 M $H_3PO_4$ was added, followed by 1.75 ml 1.00 N NaOH (mixture pH=2.49). 10.0 g collagen was added to BP and mixed for 2 hours (final pH=3.61). This makes a 1% collagen gel, which was frozen and lyophilized. A 60 mg collagen disc was loaded with 2 ml dI water and incubated 2 hours at room temperature. The resulting 3% collagen gel had a pH of 3.7. The material was injectable using #18 and #20 gauge needles, but not with #22 or #25 gauge needles. A 100 microliter volume contained 35 μg BP. Table 20 demonstrates that 3% acidic collagen matrices in the form of a gel and combined with BP induce cartilage in this in vivo system.

TABLE 20

| AED | 3% collagen + 35 μg BP |
|---|---|
| Bone score | 3.0 ± 0.0 |
| Cartilage score | 1.8 ± 0.3 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A product for repair of cartilage lesions, comprising:

a. a cartilage repair matrix suitable for conforming to a defect in cartilage; and b. a cartilage-inducing composition contained on or within said matrix comprising a mixture of proteins comprising: transforming growth factor β1 (TGFβ1), bone morphogenetic protein (BMP)-2, BMP-3, and BMP-7;

wherein the quantity of said TGFβ1 in said mixture is greater than 1% of total proteins in said mixture;

wherein the quantity of said BMP-2 in said mixture is from about 0.01% to about 10% of total proteins in said mixture;

wherein the quantity of said BMP-3 in said mixture is from about 0.1% to about 15% of total proteins in said mixture; and, wherein the quantity of said BMP-7 in said mixture is from about 0.01% to about 10% of total proteins in said mixture.

2. The product of claim 1, wherein the quantity of said TGFβ1 in said mixture is at least about 10% of total proteins in said mixture.

3. The product of claim 1, wherein said mixture of proteins further comprises TGFβ2, TGFβ3, BMP-4, BMP-5, BMP-6, cartilage-derived morphogenetic protein (CDMP), FGF-I, osteocalcin, osteonectin, BSP, lysyloxidase, cathepsin L pre, albumin, transferrin, Apo Al LP and Factor XIIIb.

4. A product for repair of cartilage lesions, comprising:

a. a cartilage repair matrix; and b. a cartilage-inducing composition contained on or within said matrix comprising a mixture of proteins comprising:

(i) a bone-derived osteogenic or chondrogenic formulation containing at least one bone morphogenetic protein (BMP); and, (ii) a TGFβ protein that is exogenous to said formulation of (i);

wherein the *weight* ratio of said exogenous TGFβ protein to total BMP in said mixture of proteins is greater than [about] 10:1; and, wherein said exogenous TGFβ protein is present in an amount sufficient to increase cartilage induction by said composition over a level of cartilage induction by said bone-derived osteogenic or chondrogenic protein formulation in the absence of said exogenous TGFβ protein.

5. The product of claim 4, wherein said exogenous TGFβ protein is TGFβ1.

6. The product of any one of claim 1 or 5, wherein the *weight* ratio of TGFβ1 to all other proteins in said mixture of proteins is at least [about] 1:10.

7. The product of any one of claim 1 or 5, wherein the *weight* ratio of TGFβ1 to all other proteins in said mixture of proteins is at least [about] 10:1.

8. The product of claim 4, wherein said mixture of proteins comprises TGFβ superfamily proteins consisting of: TGFβ1, bone morphogenetic protein (BMP)-2, BMP-3, and BMP-7, wherein said TGFβ superfamily proteins comprise from about 0.5% to about 99.99% of said mixture of proteins.

9. The product of claim 4, wherein said bone-derived osteogenic or chondrogenic formulation comprises TGFβ1, TGFβ2, TGFβ3, BMP-2, BMP-3, BMP-4, BMP-5, BMP-6, BMP-7, CDMP, FGF-I, osteocalcin, osteonectin, BSP, lysyloxidase, cathepsin L pre, albumin, transferrin, Apo Al LP and Factor XIIIb.

10. A product for repair of cartilage lesions, comprising:

a. a cartilage repair matrix; and b. a cartilage-inducing composition contained on or within said matrix comprising a mixture of proteins comprising:

(i) a TGFβ protein; and, (ii) at least one bone morphogenetic protein (BMP);

wherein the *weight* ratio of said TGFβ protein to total BMP in said mixture of proteins is greater than [about] 10:1.

11. The product of any one of claim 1, 4 or 10, wherein said mixture of proteins comprises Bone Protein (BP).

12. The product of any one of claim 1, 4 or 10, wherein said cartilage-inducing composition is at a concentration of from about 0.5% to about 33% by weight of said product.

13. The product of any one of claim 1, 4 or 10, wherein said cartilage repair matrix is bioresorbable.

14. The product of claim 1, 4 or 10, wherein said cartilage repair matrix comprises collagen from bovine tendon.

15. The product of claim 10, wherein said mixture of proteins comprises TGFβ superfamily proteins consisting of: TGFβ1, bone morphogenetic protein (BMP)-2, BMP-3, and BMP-7, wherein said TGFβ superfamily proteins comprise from about 0.5% to about 99.99% of said mixture of proteins.

16. The product of any one of claim 8 or 15, wherein said TGFβ superfamily proteins comprise from about 0.5% to about 25% of said mixture of proteins.

17. The product of any one of claim 8 or 15, wherein the quantity of said TGFβ1 in said mixture is from about 0.01% to about 75% of total proteins in said mixture.

18. The product of any one of claim 1, 8 or 15, wherein the quantity of said TGFβ1 in said mixture is from about 33% to about 99.99% of total proteins in said mixture.

19. The product of any one of claim 1, 8 or 15, wherein said mixture of proteins further comprises at least one bone matrix protein selected from the group consisting of osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and fibronectin; wherein said bone matrix protein comprises from about 20% to about 98% of said mixture of proteins.

20. The product of any one of claim 1, 8 or 15, wherein said mixture of proteins further comprises at least one growth factor protein selected from the group consisting of fibroblast growth factor-I (FGF-I), FGF-II, FGF-9, leukocyte inhibitory factor (LIF), insulin, insulin-like growth factor I (IGF-I), IGF-II, platelet-derived growth factor AA (PDGF-AA), PDGF-BB, PDGF-AB, stromal derived factor-2 (SDF-2), pituitary thyroid hormone (PTH), growth hormone, hepatocyte growth factor (HGF), epithelial growth factor (EGF), transforming growth factor-α (TGFα) and hedgehog proteins; wherein said growth factor protein comprises from about 0.01% to about 50% of said mixture of proteins.

21. The product of any one of claim 1, 8 or 15, wherein said composition further comprises one or more serum proteins.

22. The product of any one of claim 4 or 10, wherein the *weight* ratio of said TGFβ protein to total BMP in said mixture of proteins is greater than about 100:1.

23. A product for repair of cartilage lesions, comprising:

a. a cartilage repair matrix suitable for conforming to a defect in cartilage; and b. a cartilage-inducing composition contained on or within said matrix comprising a mixture of proteins comprising: transforming growth factor β1 (TGFβ1), bone morphogenetic protein (BMP)-2, BMP-3, and BMP-7;

wherein the quantity of said TGFβ1 in said mixture is greater than 1% of total proteins in said mixture;

wherein the quantity of said BMP-2 in said mixture is from about 0.01% to about 10% of total proteins in said mixture;

wherein the quantity of said BMP-3 in said mixture is at least about 0.38% of total proteins in said mixture; and, wherein the quantity of said BMP-7 in said mixture is from about 0.01% to about 10% of total proteins in said mixture.

24. The product of claim 10, wherein said BMP protein is selected from the group consisting of BMP-2, BMP-3, BMP-4, BMP-5, BMP-6, BMP-7, BMP-8, BMP-9 and cartilage-derived morphogenetic protein (CDMP).

25. The product of claim 10, wherein said mixture of proteins comprises TGFβ1, TGFβ2, TGFβ3, BMP-2, BMP-3, BMP-4, BMP-5, BMP-6, BMP-7, cartilage-derived morphogenetic protein (CDMP), FGF-I, osteocalcin, osteonectin, BSP, lysyloxidase, cathepsin L pre, albumin, transferrin, Apo Al LP and Factor XIIIb.

26. A method for repair of cartilage lesions, comprising implanting and fixing into a cartilage lesion a product comprising:

a. a cartilage repair matrix suitable for conforming to a defect in cartilage; and b. a cartilage-inducing composition contained on or within said matrix comprising a mixture of proteins comprising: transforming growth factor β1 (TGFβ1), bone morphogenetic protein (BMP)-2, BMP-3, and BMP-7;

wherein the quantity of said TGFβ1 in said mixture is greater than 1% of total proteins in said mixture;

wherein the quantity of said BMP-2 in said mixture is from about 0.01% to about 10% of total proteins in said mixture;

wherein the quantity of said BMP-3 in said mixture is from about 0.1% to about 15% of total proteins in said mixture; and, wherein the quantity of said BMP-7 in said mixture is from about 0.01% to about 10% of total proteins in said mixture;

whereby implanting and fixing said product into said cartilage lesion enhances repair of said defect in cartilage as compared to in the absence of said product.

27. A method for repair of cartilage lesions, comprising implanting and fixing into a cartilage lesion a product comprising:

a. a cartilage repair matrix; and, b. a cartilage-inducing composition contained on or within said matrix comprising a mixture of proteins comprising:

(i) a bone-derived osteogenic or chondrogenic formulation of proteins containing at least one bone morphogenetic protein (BMP); and, (ii) a TGFβ protein that is exogenous to said formulation of (i);

wherein the *weight* ratio of said exogenous TGFβ protein to total BMP in said mixture of proteins is greater than [about] 10:1; and, wherein said exogenous TGFβ protein is present in an amount sufficient to increase cartilage induction by said composition over a level of cartilage induction by said bone-derived osteogenic or chondrogenic protein formulation in the absence of said exogenous TGFβ protein;

whereby implanting and fixing said product into said cartilage lesion enhances repair of said defect in cartilage as compared to in the absence of said product.

28. The method of claim 27, wherein said TGFβ protein is TGFβ1.

29. The method of any one of claim 26 or 28, wherein the *weight* ratio of TGFβ1 to all other proteins in said mixture of proteins is at least about 1:10.

30. The method of any one of claim 26 or 28, wherein the *weight* ratio of TGFβ1 to all other proteins in said mixture of proteins is at least about 10:1.

31. A method for repair of cartilage lesions, comprising implanting and fixing into a cartilage lesion a product comprising:

a. a cartilage repair matrix; and, b. a cartilage-inducing composition contained on or within said matrix comprising a mixture of proteins comprising:

(i) a TGFβ protein; and, (ii) at least one bone morphogenetic protein (BMP);

wherein the *weight* ratio of said TGFβ protein to total BMP in said mixture of proteins is greater than [about] 10:1;

whereby implanting and fixing said product into said cartilage lesion enhances repair of said defect in cartilage as compared to in the absence of said product.

32. The method of claim 31, wherein said TGFβ protein is TGFβ1.

33. The method of any one of claim 26, 27 or 31, wherein said cartilage lesion is an articular cartilage lesion.

34. The method of any one of claim 26, 27 or 31, wherein said cartilage lesion is a meniscal cartilage lesion.

35. The method of claim 34, wherein said lesion is a vascular meniscus lesion.

36. The method of claim 34, wherein said lesion is an avascular meniscus lesion.

37. The method of any one of claim 27 or 31, wherein the *weight* ratio of said TGFβ protein to total BMP in said mixture of proteins is greater than about 100:1.

38. The product of claim 10, wherein said TGFβ protein is TGFβ1.

39. A method for repair of segmental cartilage lesions, comprising implanting and fixing into a segmental cartilage lesion:

a. a first product comprising:

(i) a cartilage repair matrix configured as a sheet; and (ii) a cartilage-inducing composition contained on or within said matrix comprising a mixture of proteins comprising: transforming growth factor β1 (TGFβ1), bone morphogenetic protein (BMP)-2, BMP-3, and BMP-7;

wherein the quantity of said TGFβ1 in said mixture is greater than 1% of total proteins in said mixture;

wherein the quantity of said BMP-2 in said mixture is from about 0.01% to about 10% of total proteins in said mixture;

wherein the quantity of said BMP-3 in said mixture is from about 0.1% to about 15% of total proteins in said mixture; and, wherein the quantity of said BMP-7 in said mixture is from about 0.01% to about 10% of total proteins in said mixture; and, b. a second product comprising a cartilage repair matrix configured to replace cartilage removed from a segmental lesion;

wherein said second product is implanted into said lesion and wherein said first product is implanted between an edge of said lesion and said second product to provide an interface between said lesion and said second product.

40. The method of claim 39, wherein said second product further comprises a cartilage-inducing composition contained on or within said matrix comprising a mixture of proteins comprising: transforming growth factor β1 (TGFβ1), bone morphogenetic protein (BMP)-2, BMP-3, and BMP-7;

wherein the quantity of said TGFβ1 in said mixture is greater than 1% of total proteins in said mixture;

wherein the quantity of said BMP-2 in said mixture is from about 0.01% to about 10% of total proteins in said mixture;

wherein the quantity of said BMP-3 in said mixture is from about 0.1% to about 15% of total proteins in said mixture; and, wherein the quantity of said BMP-7 in said mixture is from about 0.01% to about 10% of total proteins in said mixture.

41. The method of any one of claim 26, 27 or 31, wherein said lesion is a tear and wherein said matrix is configured as a sheet, wherein said step of implanting comprises inserting said product directly into said tear.

*42. A composition comprising:*

*at least one TGFβ protein; and*

*at least one bone morphogenetic protein (BMP);*

*wherein the weight ratio of said at least one TGFβ protein to said at least one BMP is a chondrogenesis inducing ratio greater than 10:1.*

*43. The composition of claim 42, wherein the at least one TGFβ protein is TGFβ1, TGFβ2, TGFβ3, TGFβ4, TGFβ5, or a mixture thereof.*

*44. The composition of claim 43, wherein the at least one TGFβ protein is TGFβ1.*

*45. The composition of claim 42, wherein the at least one TGFβ protein is exogenous.*

*46. The composition of claim 42, wherein the weight ratio of the at least one TGFβ protein to the at least one bone morphogenetic protein is greater than about 100:1.*

*47. The composition of claim 46, wherein the weight ratio of the at least one TGFβ protein to the at least one bone morphogenetic protein is greater than about 1,000:1.*

*48. The composition of claim 47, wherein the weight ratio of the at least one TGFβ protein to the at least one bone morphogenetic protein is greater than about 10,000:1.*

*49. The composition of claim 42, wherein the at least one bone morphogenetic protein is BMP-2, BMP-3, BMP-4, BMP-5, BMP-6, BMP-7, BMP-8, BMP-9, CDMP, or a mixture thereof.*

*50. The composition of claim 49, wherein the at least one bone morphogenetic protein is BMP-2, BMP-3, BMP-7, or a mixture of two or more thereof.*

*51. The composition of claim 49, wherein the at least one bone morphogenetic protein is BMP-2.*

*52. The composition of claim 49, wherein the at least one bone morphogenetic protein is BMP-3.*

*53. The composition of claim 49, wherein the at least one bone morphogenetic protein is BMP-7.*

*54. The composition of claim 49, wherein the at least one bone morphogenetic protein comprises BMP-2, BMP-3, and BMP-7.*

*55. The composition of claim 54, wherein the at least one TGFβ protein is TGFβ1.*

*56. The composition of claim 42, wherein the at least one TGFβ protein or the at least one bone morphogenetic protein are constituents of a bone-derived protein mixture.*

*57. The composition of claim 56, wherein the at least one TGFβ protein and the at least one bone morphogenetic protein are constituents of a bone-derived protein mixture.*

*58. The composition of claim 57, wherein the protein mixture is Bone Protein (BP).*

*59. The composition of claim 56, wherein the protein mixture comprises the TGFβ superfamily proteins TGFβ1, BMP-2, BMP-3, and BMP-7, and wherein said TGFβ superfamily proteins comprise from about 0.5% to about 99.99% of said protein mixture.*

*60. The composition of claim 59, wherein said TGFβ superfamily proteins comprise from about 0.5% to about 25% of said protein mixture.*

*61. The composition of claim 59, wherein the quantity of said TGFβ1 in said mixture is from about 0.01% to about 75% of total proteins in said mixture.*

*62. The composition of claim 56, wherein the TGFβ protein is exogenous to the protein mixture.*

*63. The composition of claim 62, wherein said exogenous TGFβ protein is TGFβ1.*

*64. The composition of claim 63, wherein the quantity of TGFβ1 is from about 0.1% to about 1% of total proteins in the mixture.*

*65. The composition of claim 56, wherein the protein mixture comprises a quantity of TGFβ1 that is at least about 10% of the total proteins in said protein mixture.*

*66. The composition of claim 65, wherein the weight ratio of TGFβ1 to all other proteins in said protein mixture is at least about 10:1.*

*67. The composition of claim 56, wherein the mixture of proteins comprises TGFβ superfamily proteins including TGFβ-1, BMP-2, BMP-3 and BMP-7 and wherein the TGFβ superfamily proteins comprise from about 0.5% to about 99.99% of the mixture of proteins.*

*68. The composition of claim 67, wherein the quantity of TGFβ1 in the protein mixture is from about 33% to about 99.99% of total proteins in said mixture.*

*69. The composition of claim 56, wherein said mixture of proteins further comprises at least one bone matrix protein selected from the group consisting of osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and fibronectin; wherein said bone matrix protein comprises from about 20% to about 98% of said mixture of proteins.*

*70. The composition of claim 56, wherein said mixture of proteins further comprises at least one growth factor protein selected from the group consisting of fibroblast growth factor-I (FGF-I), FGF-II, FGF-9, leukocyte inhibitory factor (LIF), insulin, insulin-like growth factor I (IGF-I), IGF-II, platelet-derived growth factor AA (PDGF-AA), PDGF-BB, PDGF-AB, stromal derived factor-2 (SDF-2), pituitary thyroid hormone (PTH), growth hormone, hepatocyte growth factor (HGF), epithelial growth factor (EGF), transforming growth factor-α (TGFα) and hedgehog proteins; wherein said growth factor protein comprises from about 0.01% to about 50% of said mixture of proteins.*

*71. The composition of claim 56, wherein said composition further comprises one or more serum proteins.*

*72. The composition of claim 42, further comprising a matrix including collagen.*

*73. The composition of claim 42, further comprising a matrix including a gel.*

*74. The composition of claim 42, further comprising a matrix including a polymer.*

*75. The composition of claim 42, further comprising an injectable matrix.*

*76. The composition of claim 42, further comprising a matrix having an acidic pH.*

*77. The composition of claim 42, wherein the composition is adapted to repair cartilage lesions selected from articular lesions, vascular meniscal lesions, and avascular meniscal lesions.*

*78. The composition of claim 77, wherein the composition is adapted to repair articular cartilage lesions.*

*79. The composition of claim 42, further comprising a matrix configured as a sheet.*

*80. The composition of claim 42, further comprising a bioresorbale matrix and wherein the at least one TGFβ protein and the at least one bone morphogenetic protein are about 0.5% to about 33% by weight of the composition.*

* * * * *